US007365200B2

(12) United States Patent
Sircar et al.

(10) Patent No.: US 7,365,200 B2
(45) Date of Patent: Apr. 29, 2008

(54) THIENOPYRIDINONE DERIVATIVES AS MACROPHAGE MIGRATION INHIBITORY FACTOR INHIBITORS

(75) Inventors: Jagadish Sircar, San Diego, CA (US); Sunil Kumar K. C., San Diego, CA (US); Timothy James Davis, San Diego, CA (US); Wenbin Ying, San Diego, CA (US)

(73) Assignee: Avanir Pharmaceuticals, Aliso Viejo, CA (US)

( * ) Notice: Subject to any disclaimer, the term of this patent is extended or adjusted under 35 U.S.C. 154(b) by 0 days.

(21) Appl. No.: 11/687,598

(22) Filed: Mar. 16, 2007

(65) Prior Publication Data
US 2007/0179149 A1 Aug. 2, 2007

Related U.S. Application Data

(63) Continuation of application No. 11/385,630, filed on Mar. 20, 2006.

(60) Provisional application No. 60/665,236, filed on Mar. 24, 2005, provisional application No. 60/733,657, filed on Nov. 4, 2005.

(51) Int. Cl.
C07D 495/04 (2006.01)
A61K 31/496 (2006.01)
(52) U.S. Cl. .................. 544/362; 514/253.04
(58) Field of Classification Search .............. None
See application file for complete search history.

(56) References Cited

U.S. PATENT DOCUMENTS 4,284,768 A 8/1981 Santilli
4,299,814 A 11/1981 Brandt et al.

(Continued)

FOREIGN PATENT DOCUMENTS

AU 592753 A 11/1985
EP 0020090 A1 12/1980

(Continued)

OTHER PUBLICATIONS

Vippagunta et al Advanced Drug Delivery Reviews, vol. 48, pp. 3-26 (2001).*
Abe et al. 1993. "Induction of Vascular Endothelial Tublar Morphogenesis by Human Glioma Cells." *J. Clin. Invest.* 92:54.

(Continued)

*Primary Examiner*—Emily Bernhardt
(74) *Attorney, Agent, or Firm*—Knobbe Martens Olson & Bear LLP

(57) ABSTRACT

Inhibitors of macrophage migration inhibitory factor having a thienopyridinone backbone are provided which have utility in the treatment of a variety of disorders, including the treatment of pathological conditions associated with macrophage migration inhibitory factor activity. The inhibitors of macrophage migration inhibitory factor have the following structures:

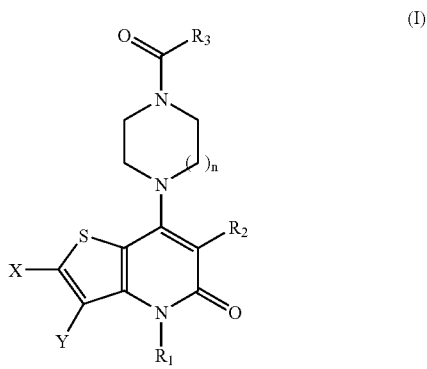

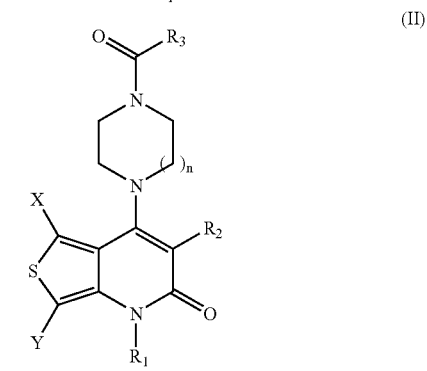

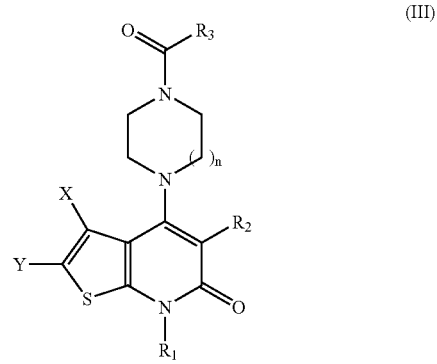

including forms such as stereoisomers, free forms, pharmaceutically acceptable salts or esters thereof, solvates, or combinations of such forms, wherein n, $R_1$, $R_2$, $R_3$, X, and Y are as defined herein. Compositions comprising an inhibitor of macrophage migration inhibitory factor in combination with a pharmaceutically acceptable carrier are also provided, as well as methods for use of the same.

22 Claims, No Drawings

U.S. PATENT DOCUMENTS

| | | | |
|---|---|---|---|
| 4,683,202 A | 7/1987 | Mullis | |
| 4,708,937 A | 11/1987 | Remold | |
| 5,246,869 A | 9/1993 | Potter et al. | |
| 5,328,990 A | 7/1994 | Wistow | |
| 5,350,687 A | 9/1994 | Odink et al. | |
| 5,352,660 A | 10/1994 | Pawson | |
| 5,411,882 A | 5/1995 | Odink et al. | |
| 5,530,101 A | 6/1996 | Queen et al. | |
| 5,597,708 A | 1/1997 | Holder et al. | |
| 5,650,295 A | 7/1997 | Li et al. | |
| 5,656,596 A | 8/1997 | Monard et al. | |
| 5,656,737 A | 8/1997 | Wistow | |
| 5,683,887 A | 11/1997 | Bucala et al. | |
| 5,700,447 A | 12/1997 | Bucala et al. | |
| 5,702,920 A | 12/1997 | Odink et al. | |
| 5,733,524 A | 3/1998 | Bucala et al. | |
| 5,733,546 A | 3/1998 | Bucala et al. | |
| 5,733,933 A | 3/1998 | Bucala et al. | |
| 5,780,615 A | 7/1998 | Bucala et al. | |
| 5,801,200 A | 9/1998 | Bucala et al. | |
| 5,821,336 A | 10/1998 | Odink et al. | |
| 5,869,534 A | 2/1999 | Bucala et al. | |
| 5,883,224 A | 3/1999 | Kirkpatrick et al. | |
| 5,919,815 A | 7/1999 | Bradley et al. | |
| 5,986,060 A | 11/1999 | Li et al. | |
| 6,028,081 A | 2/2000 | Sada et al. | |
| 6,030,615 A | 2/2000 | Bucala et al. | |
| 6,080,407 A | 6/2000 | Bucala et al. | |
| 6,214,343 B1 | 4/2001 | Kink et al. | |
| 6,238,874 B1 | 5/2001 | Jarnagin et al. | |
| 6,413,939 B1 | 7/2002 | Bucala et al. | |
| 6,420,188 B1 | 7/2002 | Bucala et al. | |
| 7,084,141 B2 | 8/2006 | Gaeta et al. | |
| 7,105,519 B2 | 9/2006 | Gaeta et al. | |
| 2003/0195194 A1 | 10/2003 | Gaeta et al. | |
| 2004/0019921 A1 | 1/2004 | Fingerle-Rowson et al. | |
| 2004/0204586 A1 | 10/2004 | Sircar et al. | |
| 2005/0124604 A1 | 6/2005 | Sircar et al. | |
| 2006/0094727 A1 | 5/2006 | Gaeta et al. | |

FOREIGN PATENT DOCUMENTS

| | | |
|---|---|---|
| EP | 0162812 A1 | 5/1985 |
| EP | 0154454 A1 | 9/1985 |
| EP | 0263072 A2 | 4/1988 |
| EP | 0412050 B1 | 2/1991 |
| EP | 0900789 A1 | 10/1999 |
| EP | 1424336 A1 | 6/2004 |
| EP | 1500402 A1 | 1/2005 |
| WO | WO 80/02287 A | 10/1980 |
| WO | WO 90/11301 A | 10/1990 |
| WO | WO 94/20083 A | 9/1994 |
| WO | WO 94/26307 A | 11/1994 |
| WO | WO 96/09389 A2 | 3/1996 |
| WO | WO 96/15242 A2 | 5/1996 |
| WO | WO 97/29635 A1 | 8/1997 |
| WO | WO 97/39326 A2 | 10/1997 |
| WO | WO 97/40159 A | 10/1997 |
| WO | WO 98/17314 A1 | 4/1998 |
| WO | WO 99/29894 A1 | 6/1999 |
| WO | WO 01/32606 A | 5/2001 |
| WO | WO 02/07720 A1 | 1/2002 |
| WO | WO 02/067862 A2 | 9/2002 |
| WO | WO 02/079517 A1 | 10/2002 |
| WO | WO 03/065979 A2 | 8/2003 |
| WO | WO 03/104178 A1 | 12/2003 |
| WO | WO 03/104203 A1 | 12/2003 |
| WO | WO 2004/060881 A | 7/2004 |
| WO | WO 2004/076679 A | 9/2004 |

OTHER PUBLICATIONS

Abe et al. 2001. "Regulation of the CTL Response by Macrophage Migration Inhibitory Factor." *J. Immunol.* 166:747-753.

Archer et al. 1983. "Electrophilic Aromatic Substitution. Part 34. Partial Rate Factors for Detritiation of Dithieno [1,2-b:4,3-b'] benzene, Dithieno[1,2-b:3,4-b'] benzene, and Dithieno [2,1-b:3,4-b']benzene." *J. Chem. Soc. Perkin Trans. II.* 813-819.

Aroca et al. 1991. "Specificity of dopachrome tautomerase and inhibition by carboxylated indoles." *Biochem. J.* 277:393-397.

Ausubel et al. 1987. *Current Protocols in Molecular Biology.* Ausubel et al.(ed.) John Wiley & Sons, Inc.

Bacher et al. 1998. "MIF Expression in the Rat Brain: Implications for Neuronal Function." *Mol. Med.* 4(4):217-230.

Baugh et al. 2002. "Macrophage migration inhibitory factor." *Crit. Care Med.* 30(1 Suppl.):S27-S35.

Bernhagen et al. 1995. "The emerging role of MIF in septic shock and infection." *Biotherapy* 8(2):123-7.

Bernhager et al. 1993. "MIF is a pituitary-derived cytokine that potentiates lethal endotoxaemia." *Nature* 365:756-759.

Bernhagen et al. 1994. "Macrophage migration inhibitory factor is a neuroendocrine mediator of endotoxaemia." *Trends Microbiol.* 2:198-201.

Bernhagen et al. 1998. "Regulation of the immune response by macrophage migration inhibitory factor: biological and structural features." *J. Mol. Med.* 76(3-4):151-161.

Bianchi et al. 1999. "Conformational Changes in Human Hepatitis C Virus NS3 Protease upon Binding of Product-Based Inhibitors." *Biochem.* 38(42): 13844-13852.

Blocki et al. 1992. "Rat liver protein linking chemical and immunological detoxification systems." *Nature* 360:269-270.

Blocki et al. 1993. "MIF proteins are theta-class glutathione S-transferase homologs." *Protein Science* 2:2095-2102.

Bone et al. 1987. "A controlled clinical trial of high-dose methylprednisolone in the treatment of severe sepsis and septic shock." N. Eng. J. Med. 317: 653-658.

Bucala. 1994. "MIF, a Previously Unrecognized Pituitary Hormone and Macrophage Cytokine, Is a Pivotal Mediator in Endotoxic Shock." *Circulatory Shock* 44(1):35-39.

Bucala. 1996. "MIF rediscovered: cytokine, pituitary hormone, and glucocorticoid-induced regulator of the immune response." *FASEB J.* 10(14):1607-1613.

Bucala. 1998. "Neuroimmunomodulation by Macrophage Migration Inhibitory Factor (MIF)." *Ann. N. Y. Acad. Sci.* 840:74-82.

Bucala. 2000. "A most interesting factor." *Nature* 408:146-147.

Calandra et al. 1996. "Macrophage Migration Inhibitory Factor: A Counter-Regulator of Glucocorticoid Action and Critical Mediator of Septic Shock." *J. Inflammation* 47:39-51.

Calandra et al. 1997. "Macrophage Migration Inhibitory Factor (MIF): A Glucocorticoid Counter-Regulator within the Immune System." *Crit. Rev. Immunol.* 17(1):77-88.

Calandra et al. 1994. "The Macrophage Is an Important and Previously Unrecognized Source of Macrophage Migration Inhibitory Factor." *J. Exp. Med.* 179:1895-1902.

Calandra et al. 1995. "MIF as a glucocorticoid-induced modulator of cytokine production." *Nature* 377:68-71.

Calandra et al. 2000. "Protection from septic shock by neutralization of macrophage migration inhibitory factor." *Nature Medicine* 6(2):164-170.

Carceller et al. 1993. "Synthesis and Structure-Activity Relationships of 1-Acyl-4((2-methyl-3-pyridyl)cyanomethyl)piperaines as PAF Antagonists." *J. Med. Chem.* 36:2984-2997.

Carvajal et al. 1982. "Cell-Mediated Immunity Against Connective Tissue in Experimental Pulmonary Fibrosis." *Lung* 160(3): 131-40.

Chesney et al. 1999. "An Essential Role for Macrophage Migration Inhibitory Factor (MIF) in Angiogenesis and the Growth of a Murine Lymphoma." *Mol. Med.* 5: 181-191.

Coppola, et al.; Transformation in the 2-Quinolone Series, Journal of Heterocyclic Chemistry, August 1981, vol. 18, No. 5, pp. 917-920.

Dandliker et al. 1970. "Fluorescence polarization in Immunochemistry." *Immunochem.* 7:799-828.

Donnelly et al. 1997. "Macrophage migration inhibitory factor: a regulator of glucocorticoid activity with a critical role in inflammatory disease," *Mol. Med. Today* 3(11):502-507.

Donnelly et al. 1997. "Regulatory role for macrophage migration inhibitory factor in acute respiratory distress syndrome." *Nat. Med.* 3(3):320-323.

Durand et al. 1998. "Interaction of methyl green with an oligonucleotide in intramolecular duplex and triplex conformations." *Eur. Biophys. J.* 27(2):147-151.

Ferro et al. 1991. "Antigen induced inhibition of autoimmune response to rat male accessory glands: role of thymocytes on the efferent phase of the suppression." *Autoimmunity* 9(3):193-200.

Florkiewicz et al. 1991a. "Basic Fibroblast Growth Factor Gene Expression." *Ann. N.Y. Acad. Sci.* 638:109-126.

Florkiewicz et al. 1991b. "Multiple forms of bFGF: differential nuclear and cell surface localization." *Growth Factors* 4:265-275.

Galat et al. 1993. "Purification of macrophage migration inhibitory factor (MIF) from bovine brain cytosol." *Fed. Eur. Biochem Soc.* 319:233-236.

Garner et al. 2003. "Macrophage Migration Inhibitory Factor (MIF) is a cardiac-derived myocardial depressant factor." *Amer. Jour. Physiol. Heart Circ Physiol.* 285(6):H2500-9. (E-pub Aug. 28, 2003).

Goto et al. 1993. "Synergistic Effects of Vascular Endothelial Growth Factor and Basic Fibroblast Growth Factor on the Proliferation and Cord Formation of Bovine Capillary Endothelial Cells Within Collagen Gels." *Lab. Invest.* 69:508-517.

Harrington et al. 1973. "Macrophage migration from an agarose droplet: development of a micromethod for assay of delayed hypersensitivity." *J. Immunol.* 110:752-759, 1973.

Haugland. 1989. *Handbook of Flourescent Probes and Research Chemicals- Seventh Ed.*, Molecular Probes, Eugene, OR. Not included, substantially cumulative with Ninth Ed. below.

Hermanowski-Vosatka et al. 1999. "Enzymatically Inactive Macrophage Migration Inhibitory Factor Monoyte Chemotaxis and Random Migration." *Biochemistry* 38:12841-12849.

Huang et al. 2001. "Macrophage Migration Inhibitory Factor Is an Important Mediator in the Pathogenesis of Gastric Inflammation in Rats." *Gastroenterology* 121:619-630.

Huse et al. 1989. "Generation of Large Combinatorial Library of the Immunoglobin Repertoire in Phage Lambda." *Science* 246:1275-1281.

Johnson et al. 1999. "A kinetic and stereochemical investigation of the role of lysine-32 in the phenylpyruvate tautomerase activity catalyzed by macrophage migration inhibitory factor." *Biochemistry* 38:16024-16033.

Kleifeld et al. 2000. "Spectroscopic Studies of Inhibited Alcohol Dehydrogenase from *Thermoanaerobacter brockii*: Proposed Structure for the Catalytic Intermediate State." *Biochem* 39(26):7702-7711.

Larsen et al. 1974. "Synthesis and Properties of 3-(3-Carboxyphenyl)pyruvic Acid and 3-(3-Carboxy-4-hydroxyphenyl)pyruvic Acid." *Acta Chem. Scand. B.* 28:92-96.

Leech et al. 1998. "Involvement of macrophage migration inhibitory factor in the evolution of rat adjuvant arthritis." *Arthritis and rheumatism* 41(5):910-917.

Lukes et al. 1954. "Synthese von α-methylfural." *Collection Czechoslov. Chem. Commun.* 19:609-610.

Lundblad et al. 1996. "Fluorescence Polarization Analysis of Protein-DNA and Protein-Protein Interactions." *Molec. Endocrinol.* 10:607-612.

Meanwell et al. 1993. "Inhibitors of Blood Platelet cAMP Phosphodiesterase. 4. Structural Variation of the Side-Chain Terminus of Water-Soluble 1,3-Dihydro-2*H*-imidazo[4,5-b]quinolin-2-one Derivatives." *J. Med. Chem.* 36:3251-3264.

Metz et al. 1997. "Role of Macrophage Migration Inhibitory Factor in Regulation of the Immune Response." *Advances in Immunology* 66:197-223.

Mitchell et al. 1999. "Sustained Mitogen-activated Protein Kinase (MAPK) and Cytoplasmic Phospholipase A2 Activation by Macrophage Migration Inhibitory Factor (MIF)." *J. Biol. Chem.* 274(25):18100-18106.

Natanson et al. 1994. "Selected Treatment Strategies for Septic Shock Based on Proposed Mechanisms of Pathogenesis." *Annals of Internal Medicine* 120(9):771-783.

Nishihira. 1998. "Novel pathophysiological aspects of macrophage migration inhibitory factor (Review)." *Int. J. Mol. Med* 2(1):17-28.

Ogawa et al. 2000. "An antibody for macrophage migration inhibitory factor suppresses tumour growth and inhibits tumour-associated angiogenesis." *Cytokine* 12(4):309-314.

Okamura et al. 1992. "Model system for tumor angiogenesis—involvement of transforming growth factor-α in tube formation of human microvascular endothelial cells induced by esophageal cancer cells." *Biochem. Biophys. Res. Comm.* 186:1471-1479.

Onodera et al. 2000. "Macrophage Migration Inhibitory Factor Up-regulates Expression of Matrix Metalloproteinases in Synovial Fibroblasts or Rheumatoid Arthritis." *J. Biol. Chem.* 275:444-450.

Pan et al. 2004. "Macrophage migration inhibitory factor deficiency impairs atherosclerosis in low-density lipoprotein receptor-deficient mice." *Circulation—Jour. Amer. Heart Assoc.* 3149-3153.

Perrin. 1926. "Polarisation de la lumiere de fluorescence vie moyenne des molecules dans l'etat excite." J. Phys. Rad. 1:390-401. (English Abstract included).

Petrovsky et al. 2002. "Macrophage Migration Inhibitory Factor: A Critical Neurohumoral Mediator." *Front Horm Res. Basel, Karger* 29:83-90.

Rice, et al. 1998. "Macrophage migration inhibitory factor (MIF): a critical upstream regulator of acute and chronic inflammatory responses." *Ann. Rep. Medicinal Chem.* 243-252.

Rosengren et al. 1996. "The Immunoregulatory Mediator Macrophage Migration Inhibitory Factor (MIF) Catalyzes a Tautomerization Reaction." *Mol. Med.* 2:143-149.

Rupreht, et al., Murine monoclonal antibodies directed against human recombinant Macrophage Migration Inhibitory Factor, *Pflügers Arch.—Eur. J. Physiol.* (2000) 440 [Suppl]:R78-R80.

Sakaue et al. 1999. "Regulation of Macrophage Migration Inhibitory Factor (MIF) Expression by Glucose and Insulin in Adipocytes In Vitro." *Mol. Med.* 5:361-371.

Sarver et al. 1999. "Thermodynamic and circular dichroism studies differentiate inhibitor interactions with the stromelysin $S_1$-$S_3$ and $S3_1$-$S3_3$ subsites." *Biochim Biophys Acta* 1434(2):304-316.

Scatchard et al. 1949. "The Attractions of Proteins for Small Molecules and Ions." *Ann. N.Y. Acad. Sci.* 51:660-672.

Scopes. 1987. *Protein Purification: Principles and Practice, Second Edition.* Springer-Verlag. N.Y.

Sprung et al. 1984. "The effects of high-dose corticosteroids in patients with septic shock." *N. Engl. J. Med.* 311: 1137-1143.

Swope et al. 1999. "Macrophage Migration Inhibitory Factor: Cytokine, Hormone, or Enzyme?" *Rev. Physiol. Biochem. Pharmacol.* 139:1-32.

Swope et al. 1998. "Direct link between cytokine activity and catalytic site for macrophage migration inhibitory factor." *EMBO J.* 17(13):3534-3541.

Takahashi et al. 1998. "Involvement of Macrophage Migration Inhibitory Factor (MIF) in the Mechanism of Tumor Cell Growth." *Mol. Med.* 4:707-714.

Takahashi et al. 1999 "Antisense Macrophage Migration Inhibitory Factor (MIF) Prevents Anti-IgM Mediated Growth Arrest and Apoptosis of a Mature B Cell Line by Regulating Cell Cycle Progression." *Microbiol. Immunol.* 43(1)61-67.

Urry. 1969. "Optical Rotation and Biomolecular Conformation." *Spectroscopic Approaches to Biomolecular Conformation.* American Medical Association Press, Chicago, IL, pp. 33-121.

Waeber et al. 1999. "A Role for the Endocrine and Pro-inflammatory Mediator MIF in the Control of Insulin Secretion During Stress." *Diabetes Met. Res. Rev.* 15(1):47-54.

Ward et al. 1989. "Binding activities of a repertoire of single immunogloblin variable domains secreted from *Escherichia coli.*" *Nature* 341:544-546.

Warren et al. 1995. "Regulation by Vascular Endothelial Growth Factor of Human Colon Cancer Tumorgenesis in a Mouse Model of Experimental Liver Metastasis." *J. Clin. Invest.* 95:1789-1797.

Weir. 1986. *Handbook of Experimental Immunology, Cellular Immunology.* Backwell Scientific, Boston, MA.

Weiser et al. 1985. "Generation of human hybridomas producing migration inhibitory factor (MIF) and of murine hybridomas secreting monoclonal antibodies to human MIF." *Cellular Immunol.* 90:167-178.

Weiser et al. 1989. "Molecular cloning of a cDNA encoding a human macrophage migration inhibitory factor." *Proc. Natl. Acad. Sci. USA.* 86:7522-7526.

Weiser et al. 1991. "Human recombinant migration inhibitory factor activates human macrophages to kill *Leishmania donovani*." *J. Immunol.* 147:2006-2011.

Winder et al. 1993. "The mouse brown (b) locus protein has dopachrome tautomerase activity and is located in lysosomes in transfected fibroblasts." *J. Cell Sci.* 106:153-166.

Winter et al. 1993. "Humanized antibodies." *Immunol. Today* 14(6):243-246.

Wistow et al. 1993. "A macrophage migration inhibitory factor is expressed in the differentiating cells of the eye lens." *Proc. Natl. Acad. Sci.* USA 90:1272-1275.

Wu et al. 1994. "Resonance Energy Transfer: Methods and Applications." *Analytical Biochem.* 218:1-13.

Yang et al. 1998. "Reversal of Established Rat Crescentic Glomerulonephritis by Blockade of Macrophage Migration Inhibitory Factor (MIF): Potential Role of MIF in Regulating Glucocorticoid Production." *Mol. Med* 4(6):413-424.

Zuckerman et al. 1989. "Differential regulation of lipopolysaccharide-induced interleukin 1 and tumour necrosis factor synthesis: effects on endogenous and exogenous glucocorticoids and the role of the pituitary-adrenal axis." *Eur. J. Immunol.* 19:310-305.

Morand et al., Expert Opin. Ther. Patents, vol. 13, pp. 1189-1212 (2003).

Riedemann et al., J. Clin. Invest., vol. 112, pp. 460-467 (2003).

Patent Abstracts of Japan, vol. 2000, No. 21—abstract for JP 2001 097979 A.

PCT International Search Report and Written Opinion for PCT/US2006/009932 mailed Jul. 24, 2006.

Wolff, Manfred E., Burgers Medicinal Chemistry, $5_{th}$ Ed. Part 1, pp. 975-977 (1995).

Office Action mailed Jul. 16, 2007 in co-pending U.S. Appl. No. 11/385,630.

\* cited by examiner

THIENOPYRIDINONE DERIVATIVES AS MACROPHAGE MIGRATION INHIBITORY FACTOR INHIBITORS

RELATED APPLICATIONS

This application is a continuation of U.S. patent application Ser. No. 11/385,630, filed Mar. 20, 2006, which claims the benefit of U.S. Provisional Application No. 60/665,236, filed Mar. 24, 2005, and U.S. Provisional Application No. 60/733,657, filed Nov. 4, 2005. All above-referenced prior applications are incorporated by reference herein in their entirety and are hereby made a portion of this specification.

FIELD OF THE INVENTION

The present invention relates to organic compounds, e.g., thienopyridinone derivatives, that are macrophage migration inhibitory factor (MIF) inhibitors.

BACKGROUND OF THE INVENTION

The lymphokine, macrophage migration inhibitory factor (MIF), has been identified as a mediator of the function of macrophages in host defense and its expression correlates with delayed hypersensitivity, immunoregulation, inflammation, and cellular immunity. Although MIF was first characterized as being able to block macrophage migration, MIF also appears to effect macrophage adherence; induce macrophage to express interleukin-1-beta, interleukin-6, and tumor necrosis factor alpha; up-regulate HLA-DR; increase nitric oxide synthase and nitric oxide concentrations; and activate macrophage to kill *Leishmania donovani* tumor cells and inhibit *Mycoplasma avium* growth, by a mechanism different from that effected by interferon-gamma.

In addition to its potential role as an immunoevasive molecule, MIF can act as an immunoadjuvant when given with bovine serum albumin or HIV gp120 in incomplete Freunds or liposomes, eliciting antigen induced proliferation comparable to that of complete Freunds. Also, MIF has been described as a glucocorticoid counter regulator and angiogenic factor. As one of the few proteins that is induced and not inhibited by glucocorticoids, it serves to attenuate the immunosuppressive effects of glucocorticoids. As such, it is viewed as a powerful element that regulates the immunosuppressive effects of glucocorticoids. Hence, when its activities/gene expression are overinduced by the administration of excess exogenous glucocorticoids (for example when clinical indicated to suppress inflammation, immunity and the like), there is significant toxicity because MIF itself exacerbates the inflammatory/immune response. See Bucala et al., *Ann. Rep. Med. Chem.* 33:243-252, 1998.

The interest in developing MIF inhibitors derives from the observation that MIF is known for its cytokine activity concentrating macrophages at sites of infection, and cell-mediated immunity. Moreover, MIF is known as a mediator of macrophage adherence, phagocytosis, and tumoricidal activity. Hence, the inhibition of MIF results in the indirect inhibition of cytokines, growth factors, chemokines, and lymphokines that the macrophage may otherwise bring to a site of inflammation.

SUMMARY OF THE INVENTION

As MIF has been identified in a variety of tissues and has been associated with numerous pathological events, there exists a need for pharmaceutical compositions comprising MIF inhibitors, as well as methods relating to the use thereof to treat, for example, immune related disorders or other MIF induced pathological events, such as tumor associated angiogenesis. The preferred embodiments fulfill these needs, and provide other advantages as well.

In preferred embodiments, MIF inhibitors are provided that have the following general structures (I), (II), or (III), including forms such as stereoisomers, free forms, pharmaceutically acceptable salts or esters thereof, solvates, or combinations of such forms, wherein n, $R_1$, $R_2$, $R_3$, X, and Y are as defined below:

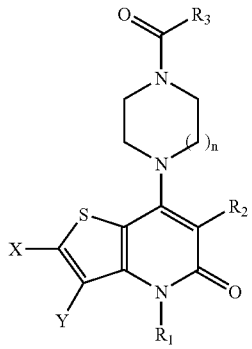

(I)

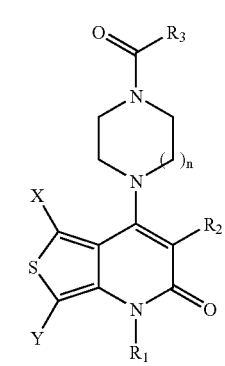

(II)

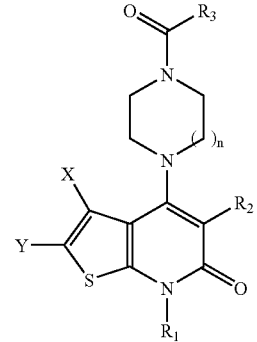

(III)

The MIF inhibitors of preferred embodiments have utility over a wide range of therapeutic applications, and may be employed to treat a variety of disorders, illnesses, or pathological conditions including, but not limited to, a variety of immune related responses, tumor growth (e.g., prostate cancer, etc.), glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, otitis media, Crohn's disease, acute respiratory distress syndrome, delayed-type hypersensitivity, and others.

Therapeutic methods include administering an effective amount of one or more MIF inhibitors as provided by the preferred embodiments, preferably in the form of a pharmaceutical composition, to patient in need thereof Pharmaceutical compositions are provided containing one or more MIF inhibitors of preferred embodiments in combination with pharmaceutically acceptable carrier(s) and/or diluent(s).

Accordingly, in a first aspect a compound is provided having structure (I), structure (II), or structure (III):

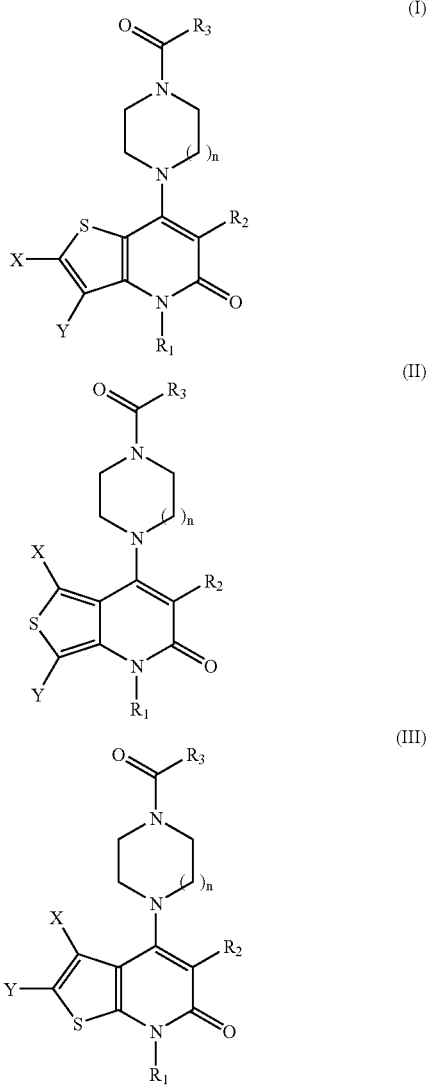

or a stereoisomer, or a pharmaceutically acceptable salt, ester, or solvate thereof, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl) amino; X is hydrogen, halogen, $C_{1-6}$ alkyl, $C_{1-6}$ alkoxy, $C_{1-6}$ alkylamino, or di-($C_{1-6}$ alkyl)amino; Y is hydrogen, halogen, $C_{1-6}$ alkyl, $C_{1-6}$ alkoxy, $C_{1-6}$ alkylamino, or di-($C_{1-6}$ alkyl) amino; and n is 0, 1, or 2.

In an embodiment of the first aspect, $R_3$ is thiophenyl, furanyl, 4-hydroxyphenyl, 4-methoxyphenyl, or 5-F-thiophenyl. In an embodiment of the first aspect, $R_2$ is —CN, —C(=O)OCH$_2$CH$_3$, or —C(=O)OCH(CH$_3$)$_2$. In an embodiment of the first aspect, X is hydrogen, and/or Y is hydrogen. In an embodiment of the first aspect, n is 1. In an embodiment of the first aspect, the compound is in a form of a salt. In an embodiment of the first aspect, the compound is for use as a pharmaceutical composition.

In an embodiment of the first aspect, a pharmaceutical composition is provided comprising a compound of the first aspect in association with at least one pharmaceutically acceptable excipient. In an embodiment of the first aspect, a pharmaceutical composition is provided comprising a compound of the first aspect and at least one additional pharmaceutically active agent.

In an embodiment of the first aspect, use of a compound of the first aspect for the manufacture of a medicament for the treatment of a disease or disorder mediated by macrophage migration inhibitory factor is provided.

In an embodiment of the first aspect, a method is provided for treating a disease or disorder such as inflammation, septic shock, arthritis, cancer, acute respiratory distress syndrome, inflammatory disease, rheumatoid arthritis, osteoarthritis, inflammatory bowel disease, asthma, autoimmune disorder, Lyme disease, Lupus, Acquired Immune Deficiency Syndrome, diabetes, multiple sclerosis, congestive heart failure, cardiovascular disease restenosis, and atherosclerosis, the method comprising administering to a patient in need thereof an effective amount of the compound of the first aspect. The method can also comprise administering a compound of the first aspect in combination with another pharmaceutically active agent, either simultaneously or in sequence.

In a second aspect, a pharmaceutical composition is provided comprising a compound having structure (I), structure (II), or structure (III):

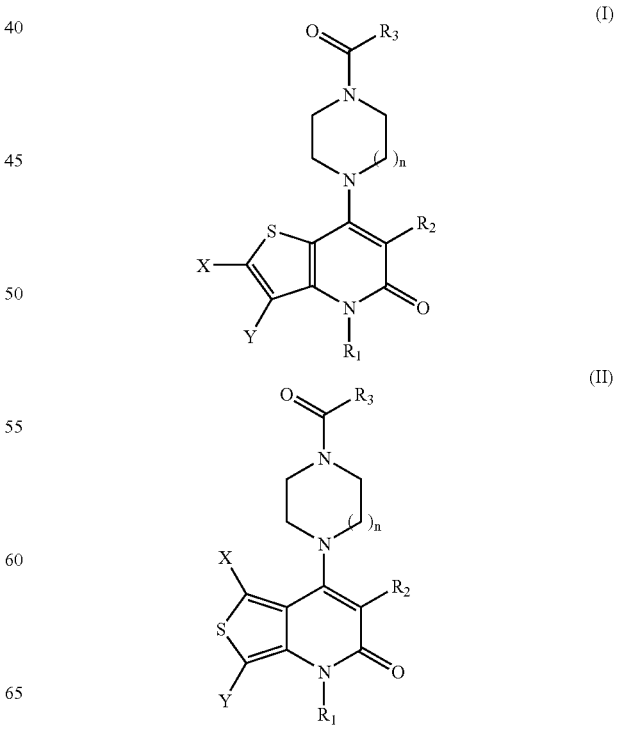

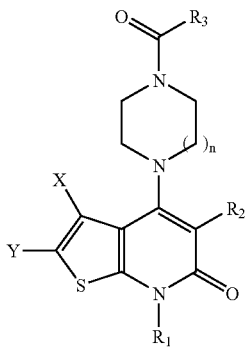

(III)

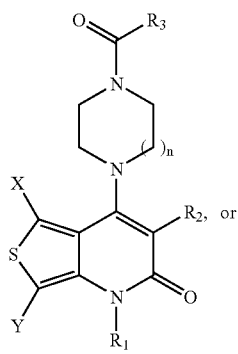

(II)

or a stereoisomer, or a pharmaceutically acceptable salt, ester, or solvate thereof, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); $R_3$ is $C_{1-8}$ alkyl, —$(CH_2)_y$—($C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; X is hydrogen, halogen, $C_{1-6}$ alkyl, $C_{1-6}$ alkoxy, $C_{1-6}$ alkylamino, or di-($C_{1-6}$ alkyl)amino; Y is hydrogen, halogen, $C_{1-6}$ alkyl, $C_{1-6}$ alkoxy, $C_{1-6}$ alkylamino, or di-($C_{1-6}$ alkyl)amino; and n is 0, 1, or 2; in combination with a pharmaceutically acceptable carrier or diluent.

In a third aspect, a method for reducing macrophage migration inhibitory factor activity in a patient in need thereof is provided, comprising administering to the patient an effective amount of a compound having the structure:

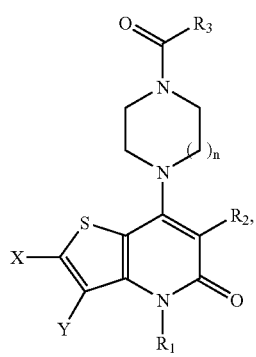

(I)

or a stereoisomer, or a pharmaceutically acceptable salt, ester, or solvate thereof, wherein $R_1$ is hydrogen, $C_{1-8}$ alkyl, —$(CH_2)_x$—($C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); $R_3$ is $C_{1-8}$ alkyl, —$(CH_2)_y$—($C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; X is hydrogen, halogen, $C_{1-6}$ alkyl, $C_{1-6}$ alkoxy, $C_{1-6}$ alkylamino, or di-($C_{1-6}$ alkyl)amino; Y is hydrogen, halogen, $C_{1-6}$ alkyl, $C_{1-6}$ alkoxy, $C_{1-6}$ alkylamino, or di-($C_{1-6}$ alkyl)amino; and n is 0, 1, or 2.

In a fourth aspect, a method for treating a disease or a disorder in an animal is provided, the method comprising administering to the animal an effective amount of a compound having the structure:

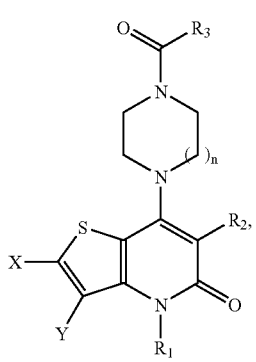

(I)

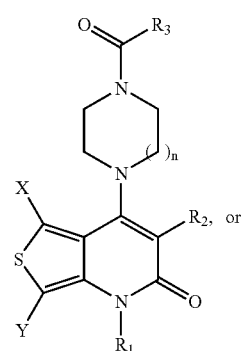

(II)

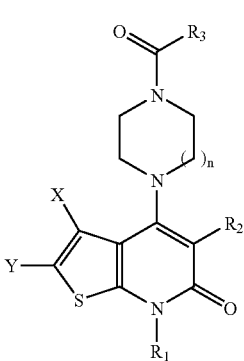

(III)

or a stereoisomer, or a pharmaceutically acceptable salt, ester, or solvate thereof, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl) amino; X is hydrogen, halogen, $C_{1-6}$ alkyl, $C_{1-6}$ alkoxy, $C_{1-6}$ alkylamino, or di-($C_{1-6}$ alkyl)amino; Y is hydrogen, halogen, $C_{1-6}$ alkyl, $C_{1-6}$ alkoxy, $C_{1-6}$ alkylamino, or di-($C_{1-6}$ alkyl) amino; and n is 0, 1, or 2.

In an embodiment of the fourth aspect, the disease or disorder is inflammation, septic shock, arthritis, cancer, acute respiratory distress syndrome, an inflammatory disease, rheumatoid arthritis, osteoarthritis, inflammatory bowel disease, asthma, an autoimmune disorder, diabetes, or multiple sclerosis.

In an embodiment of the fourth aspect, an immune response is suppressed.

In an embodiment of the fourth aspect, angiogenesis is decreased.

In an embodiment of the fourth aspect, the disease is associated with excess glucocorticoid levels, for example, Cushing's disease.

In a fifth aspect, a pharmaceutical composition is provided for treating a disease or disorder wherein macrophage migration inhibitory factor is pathogenic, the pharmaceutical composition comprising a compound of structure (I), (II), or (III):

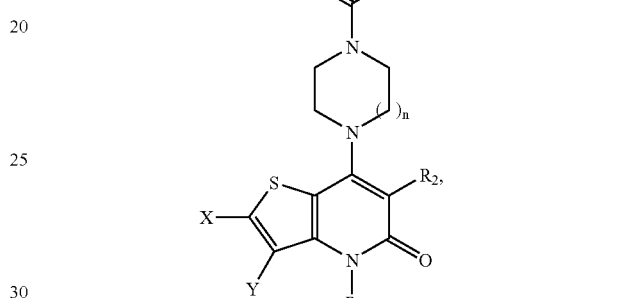

(I)

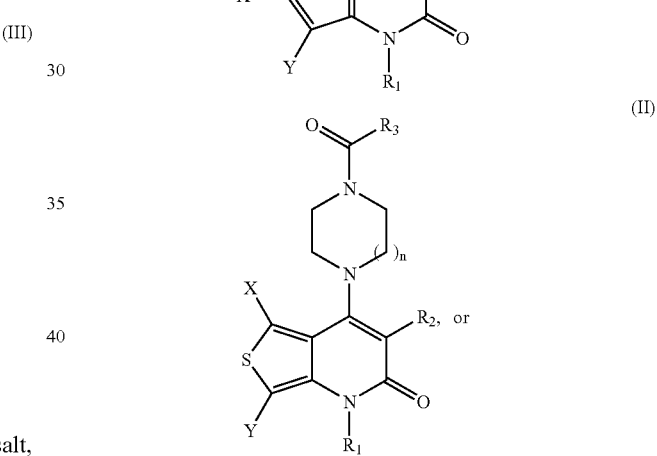

(II)

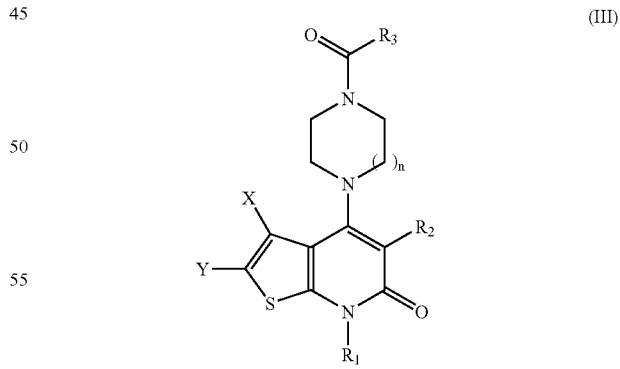

(III)

or a stereoisomer, or a pharmaceutically acceptable salt, ester, or solvate thereof, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; $R_2$ is —NO, —$NO_2$, —$CONH_2$, —C(=O)—NH($C_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; X is hydrogen, halogen, C$_{1-6}$ alkyl, C$_{1-6}$ alkoxy, C$_{1-6}$ alkylamino, or di-(C$_{1-6}$ alkyl)amino; Y is hydrogen, halogen, C$_{1-6}$ alkyl, C$_{1-6}$ alkoxy, C$_{1-6}$ alkylamino, or di-(C$_{1-6}$ alkyl)amino; and n is 0, 1, or 2.

In a sixth aspect, a pharmaceutical composition is provided for treating a disease or disorder wherein macrophage migration inhibitory factor is pathogenic, the pharmaceutical composition comprising a compound of structure (I), (II), or (III) in combination with a drug for treating the disease or disorder, wherein the drug has no measurable MIF inhibiting activity, and wherein structures (I), (II), and (III) are as follows:

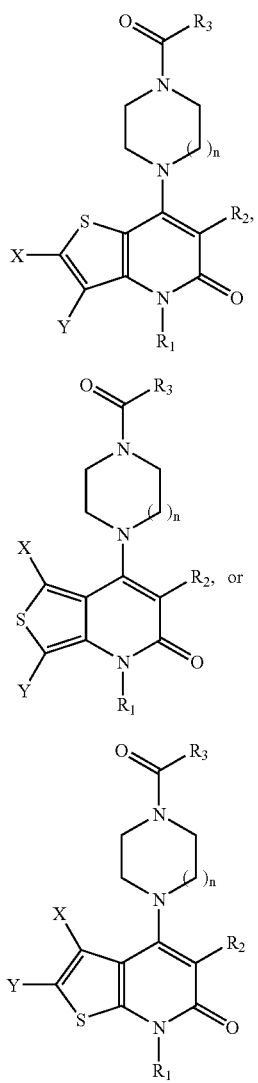

or a stereoisomer, or a pharmaceutically acceptable salt, ester, or solvate thereof, wherein R$_1$ is hydrogen, C$_{1-8}$ alkyl, —(CH$_2$)$_x$—(C$_{6-18}$ aryl), or —(CH$_2$)$_x$-(5-7 membered heterocycle), wherein x is 0 to 4, and wherein R$_1$ is unsubstituted or substituted with at least one of halogen, keto, C$_{1-6}$ alkyl, C$_{1-6}$ alkoxy, C$_{1-6}$ alkylamino, or di-(C$_{1-6}$ alkyl)amino; R$_2$ is —NO, —NO$_2$, —CONH$_2$, —C(=O)—NH(C$_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; X is hydrogen, halogen, C$_{1-6}$ alkyl, C$_{1-6}$ alkoxy, C$_{1-6}$ alkylamino, or di-(C$_{1-6}$ alkyl)amino; Y is hydrogen, halogen, C$_{1-6}$ alkyl, C$_{1-6}$ alkoxy, C$_{1-6}$ alkylamino, or di-(C$_{1-6}$ alkyl)amino; and n is 0, 1, or 2.

In an embodiment of the sixth aspect, the disease or disorder is inflammation, septic shock, or rheumatoid arthritis and the drug is a steroid.

In an embodiment of the sixth aspect, the disease or disorder is asthma or acute respiratory distress, and the drug is a corticosteroid, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, or dexamethasone.

In an embodiment of the sixth aspect, the disease or disorder is asthma or acute respiratory distress, and the drug is beclomethasone, fluticasone, triamcinolone, mometasone, prednisone, prednisolone, methylprednisolone, an azatadine, carbinoxamine/pseudoephedrine, cetirizine, cyproheptadine, dexclorpheniramine, fexofenadine, loratadine, promethazine, tripelenmamine, brompheniramine, cholopheniramine, clemastine, diphenhydramine, or epinephrine.

In an embodiment of the sixth aspect, the disease or disorder is irritable bowel disease, and the drug is azathioprine or a corticosteroid.

In an embodiment of the sixth aspect, the disease or disorder is cancer, and the drug is paclitaxel.

In an embodiment of the sixth aspect, the disease or disorder is an immune disorder and the drug is an immunosuppressive compound. The immune disorder can be Lyme disease, Lupus, or Acquired Immune Deficiency Syndrome. The drug can be a protease inhibitor, a nucleoside reverse transcriptase inhibitor, a nucleotide reverse transcriptase inhibitor, a non-nucleoside reverse transcriptase inhibitor, a biological response modifier, a compound that inhibits or interferes with tumor necrosing factor, or an antiviral. Examples of drugs include indinavir, amprenavir, saquinavir, lopinavir, ritonavir, nelfinavir zidovudine, abacavir, lamivudine, idanosine, zalcitabine, stavudine, tenofovir disoproxil fumarate delavirdine, efavirenz, nevirapine, etanercept, infliximab, amivudine, or zidovudine.

In a seventh aspect, a pharmaceutical composition is provided for treating a disease or disorder wherein macrophage migration inhibitory factor is pathogenic, the pharmaceutical composition comprising a compound of structure (I), (II), or (III) and a drug such as a nonsteroidal anti-inflammatory drug, an anti-infective drug, a beta stimulant, a steroid, an antihistamnine, an anticancer drug, an asthma drug, a sepsis drug, an arthritis drug, or an immunosuppressive drug, and wherein structures (I), (II), and (III) are as follows:

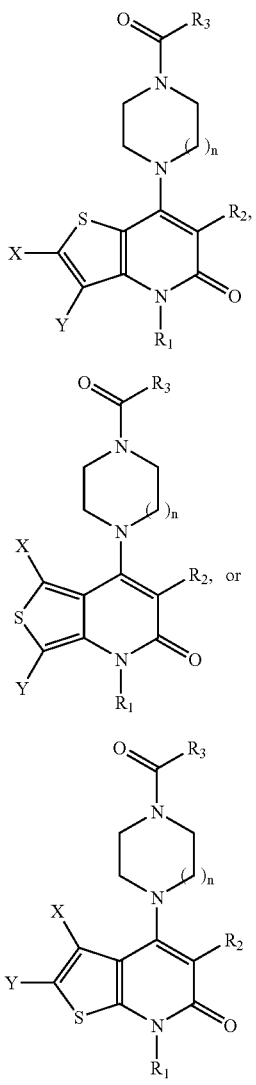

or a stereoisomer, or a pharmaceutically acceptable salt, ester, or solvate thereof, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl) amino; X is hydrogen, halogen, $C_{1-6}$ alkyl, $C_{1-6}$ alkoxy, $C_{1-6}$ alkylamino, or di-($C_{1-6}$ alkyl)amino; Y is hydrogen, halogen, $C_{1-6}$ alkyl, $C_{1-6}$ alkoxy, $C_{1-6}$ alkylamino, or di-($C_{1-6}$ alkyl) amino; and n is 0, 1, or 2. The beta stimulant can be a bronchodilator, an inhalation corticosteroid, or a hormone. The inhalation corticosteroid can be beclomethasone, fluticasone, triamcinolone, mometasone, prednisone, prednisolone, or methylprednisolone. The antihistamine can be azatadine, carbinoxamine/pseudoephedrine, cetirizine, cyproheptadine, dexchlorpheniramine, fexofenadine, loratadine, promethazine, tripelermamine, brompheniramine, cholopheniramine, clemastine, diphenhydramine, or epinephrine. The steroid can be cortisone, hydrocortisone, methylprednisolone, prednisone, prednisolone, betamethasone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, or dexamethasone. The anti-infective drug can be an anthelmintic, an aminoclycoside, an antifungal antibiotic, a cephalosporin, a beta-lactam antibiotic, chloramphenicol, a macrolide, a penicillin, a tetracycline, bacitracin, clindamycin, colistimethate sodium, polymyxin b sulfate, vancomycin, antivirals, acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, a quinolone, a sulfonamide, furazolidone, metronidazole, pentamidine, sulfanilamidum crystallinum, gatifloxacin, sulfamethoxazole/trimethoprim, mebendazole, gentamicin, neomycin, tobramycin, amphotericin b, fluconazole, griseofulvin, itraconazole, ketoconazole, nystatin, micatin, tolnaftate, cefaclor, cefazolin, cefotaxime, ceftazidime, ceftriaxone, cefuroxime, cephalexin, cefotetan, meropenem, azithromycin, clarithromycin, erythromycin, penicillin G sodium salt, amoxicillin, ampicillin, dicloxacillin, nafcillin, piperacillin, ticarcillin, doxycycline, minocycline, tetracycline, ciprofloxacin, levofloxacin, sulfadiazine, sulfisoxazole, or dapsone. The nonsteroidal anti-inflammatory drug can be celecoxib, rofecoxib, aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, or tolmetin.

In an eighth aspect, a process for preparing a compound of Formula (I-7) for use as a macrophage migration inhibitory factor inhibitor is provided, the process comprising the steps of reacting $POCl_3$ with a compound of Formula (I-3)

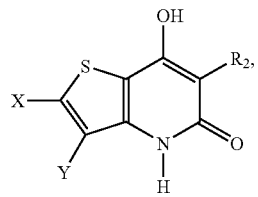

Formula (I-3)

wherein $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; thereby yielding a compound of Formula (I-4):

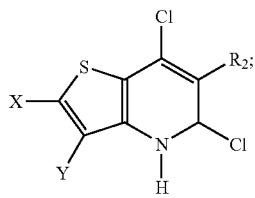

Formula (I-4)

reacting the compound of Formula (I-4) with NH₄OAc, thereby yielding a compound of Formula (I-5):

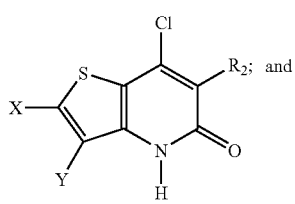

Formula (I-5)

reacting the compound of Formula (I-5) with a compound of Formula (I-6):

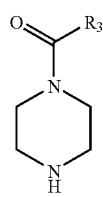

Formula (I-6)

wherein $R_3$ is $C_{1-8}$ alkyl, —$(CH_2)_x$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl) amino; thereby yielding a compound of Formula (I-7):

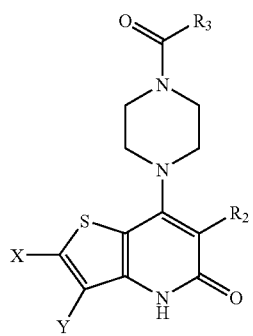

Formula (I-7)

wherein the compound of Formula (I-7) is suitable for use as a macrophage migration inhibitory factor inhibitor.

In a ninth aspect, a process for preparing a compound of Formula (I-8) suitable for use as a macrophage migration inhibitory factor inhibitor is provided, the process comprising the steps of reacting a compound of Formula (I-7):

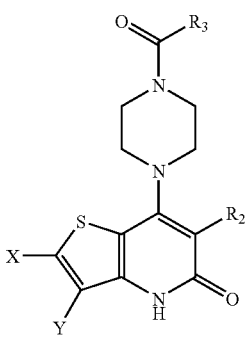

Formula (I-7)

wherein $R_2$ is —NO, —NO₂, —CONH₂, —C(=O)—NH($C_{1-6}$ alkyl), —C(=O)—N($C_{1-6}$ alkyl)₂, —C(=O)—NH-(5-7 membered heterocycle), —C(=O)-(5-7 membered heterocycle), —C(=O)—N[(CH₂)₂]₂N—CH₃, —C(=O)—($C_{1-6}$ alkyl), —CN, —C(=O)O—($C_{1-6}$ alkyl), or —OC(=O)—($C_{1-6}$ alkyl); wherein $R_3$ is $C_{1-8}$ alkyl, —$(CH_2)_x$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; thereby yielding a compound of Formula (I-8):

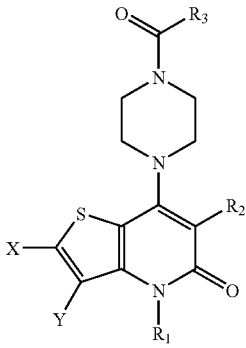

Formula (I-8)

wherein the compound of Formula (I-8) is suitable for use as a macrophage migration inhibitory factor inhibitor.

In an embodiment of the ninth aspect, $R_1$ is

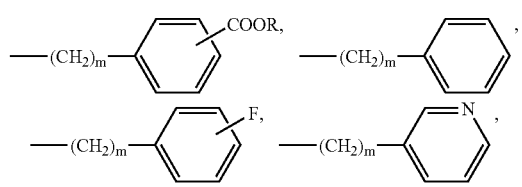

-continued

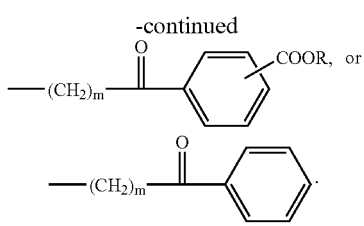

In an embodiment of the ninth aspect, $R_2$ is —C(=O)OCH$_2$CH$_3$ or —CN.

In an embodiment of the ninth aspect, $R_3$ is

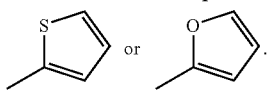

In a tenth aspect, process is provided for preparing a compound of Formula (I-7) suitable for use as a macrophage migration inhibitory factor inhibitor, the process comprising the steps of reacting a compound of Formula (I-5):

Formula (I-5)

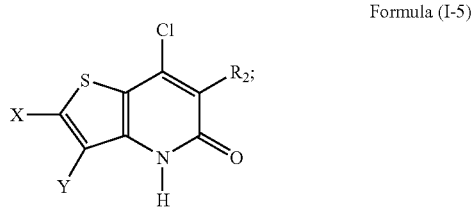

wherein $R_2$ is —NO, —NO$_2$, —CONH$_2$, —C(=O)—NH(C$_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; with a compound of Formula (I-9):

Formula (I-9)

wherein boc is t-butyloxycarbonyl, thereby yielding a compound of Formula (I-10):

Formula (I-10)

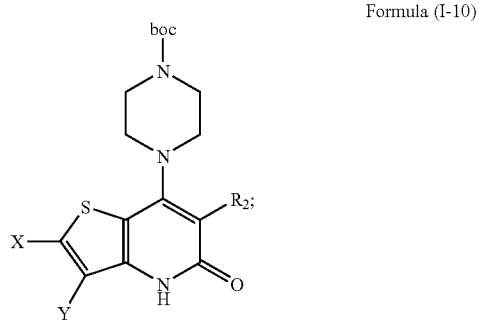

reacting the compound of Formula (I-10) with a compound having the formula $R_1$-Z, wherein $R_1$ is hydrogen, C$_{1-8}$ alkyl, —(CH$_2$)$_x$—(C$_{6-18}$ aryl), or —(CH$_2$)$_x$-(5-7 membered heterocycle), wherein x is 0 to 4, and wherein $R_1$ is unsubstituted or substituted with at least one of halogen, keto, C$_{1-6}$ alkyl, C$_{1-6}$ alkoxy, C$_{1-6}$ alkylamino, or di-(C$_{1-6}$ alkyl)amino; and wherein Z is Cl, Br, I, or B(OH)$_2$, thereby yielding a compound of Formula (I-11):

Formula (I-11)

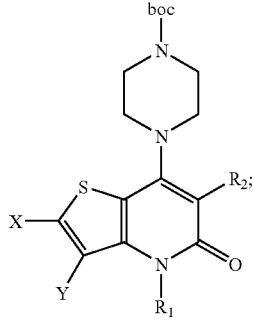

reacting the compound of Formula (I-11) with trifluoroacetic acid to yield a compound of Formula (I-12):

Formula (I-12)

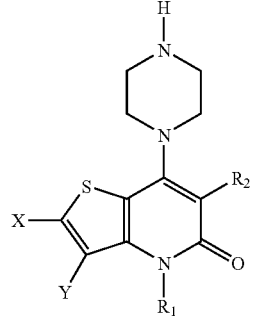

reacting the compound of Formula (I-12) with $R_3$—C(=O)-Z, wherein Z is Cl, Br, or I, or wherein $R_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein $R_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; whereby a compound of Formula (I-8) is obtained:

Formula (I-8)

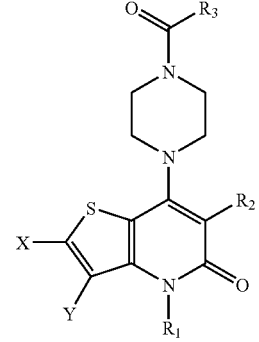

wherein the compound of Formula (I-8) is suitable for use as a macrophage migration inhibitory factor inhibitor.

In an eleventh aspect, a process is provided for preparing a compound of Formula (I-7a) suitable for use as a macrophage migration inhibitory factor inhibitor, the process comprising the steps of reacting methylcyanoacetate with a compound of Formula (I-13):

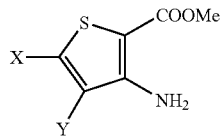

Formula (I-13)

wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; to yield a compound of Formula (I-14):

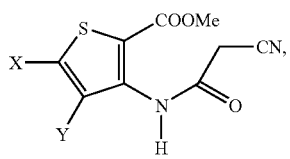

Formula (I-14)

reacting NaOEt with the compound of Formula (I-14) to yield a compound of Formula (I-3a):

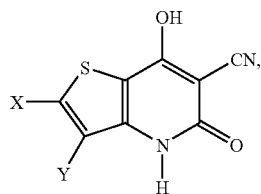

Formula (I-3a)

reacting the compound of Formula (I-3a) with POCl$_3$, thereby yielding a compound of Formula (I-5a):

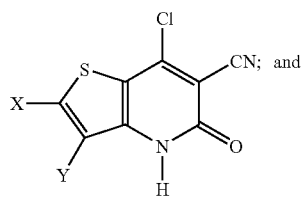

Formula (I-5a)

reacting the compound of Formula (I-5a) with a compound of Formula (I-6):

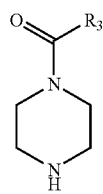

Formula (I-6)

wherein R$_3$ is $C_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, $C_{1-6}$ alkyl, $C_{1-6}$ alkoxy, $C_{1-6}$ alkylamino, or di-($C_{1-6}$ alkyl) amino, thereby yielding a compound of Formula (I-7a):

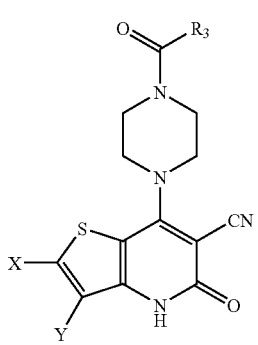

Formula (I-7a)

wherein the compound of Formula (I-7a) is suitable for use as a macrophage migration inhibitory factor inhibitor.

In a twelfth aspect, a process is provided for preparing a compound of Formula (I-8a) suitable for use as a macrophage migration inhibitory factor inhibitor, the process comprising the steps of reacting a compound of Formula (I-7a):

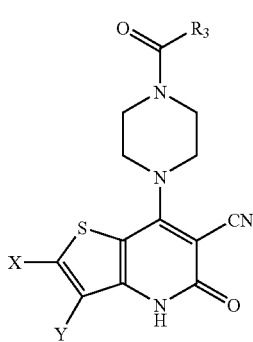

Formula (I-7a)

wherein R$_3$ is $C_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, $C_{1-6}$ alkyl, $C_{1-6}$ alkoxy, $C_{1-6}$ alkylamino, or di-($C_{1-6}$ alkyl) amino; with a compound having the formula R$_1$-Z, wherein R$_1$ is hydrogen, $C_{1-8}$ alkyl, —(CH$_2$)$_x$—(C$_{6-18}$ aryl), or —(CH$_2$)$_x$-(5-7 membered heterocycle), wherein x is 0 to 4, and wherein R$_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; thereby yielding a compound of Formula (I-8a):

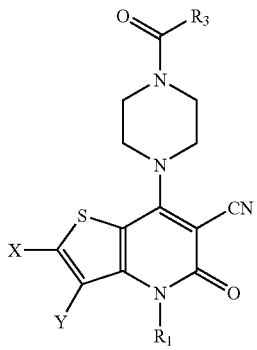

Formula (I-8a)

wherein the compound of Formula (8a) is suitable for use as a macrophage migration inhibitory factor inhibitor.

In an embodiment of the twelfth aspect, $R_1$ is

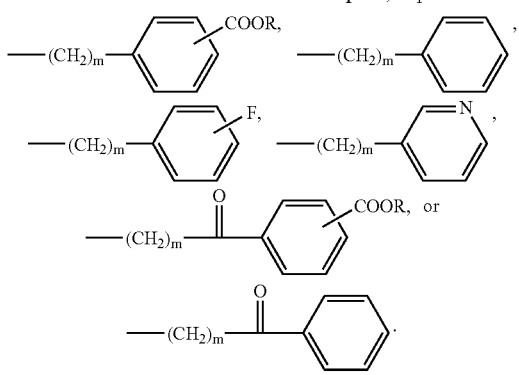

In an embodiment of the twelfth aspect, $R_3$ is

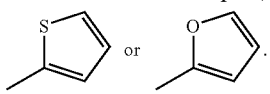

In a thirteenth aspect, a process is provided for preparing a compound of Formula (I-8a) suitable for use as a macrophage migration inhibitory factor inhibitor, the process comprising the steps of reacting a compound of Formula (I-5a):

Formula (I-5a)

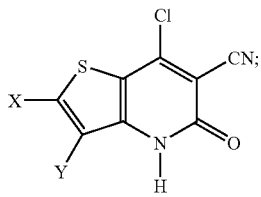

wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; with a compound of Formula (I-9):

Formula (I-9)

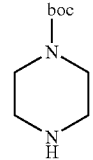

wherein boc is t-butyloxycarbonyl, thereby yielding a compound of Formula (I-10):

Formula (I-10a)

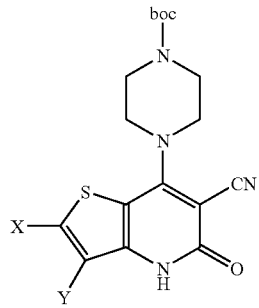

reacting the compound of Formula (I-10) with a compound having the formula $R_1$-Z, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; and wherein Z is Cl, Br, I, or B(OH)$_2$, thereby yielding a compound of Formula (I-11a):

Formula (I-11a)

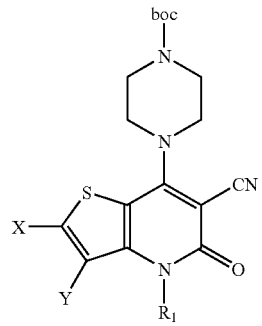

reacting the compound of Formula (I-11a) with trifluoroacetic acid to yield a compound of Formula (I-12a):

Formula (I-12a)

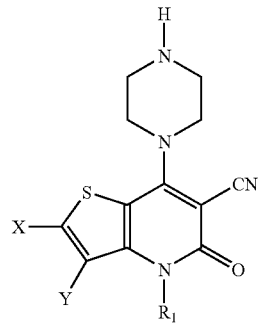

reacting the compound of Formula (I-12a) with $R_3$—C(=O)-Z, wherein Z is Cl, Br, or I, and wherein $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; whereby a compound of Formula (I-8a) is obtained:

Formula (I-8a)

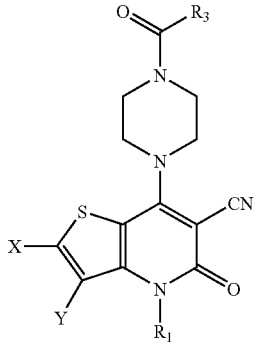

wherein the compound of Formula (I-8) is suitable for use as a macrophage migration inhibitory factor inhibitor.

A process for preparing a compound of Formula (I-7) suitable for use as a macrophage migration inhibitory factor inhibitor, the process comprising the steps of reacting POCl$_3$ with a compound of Formula (II-3):

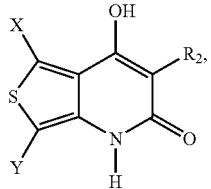

Formula (II-3)

wherein R$_2$ is —NO, —NO$_2$, —CONH$_2$, —C(=O)—NH(C$_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; thereby yielding a compound of Formula (II-4):

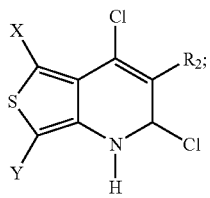

Formula (II-4)

reacting the compound of Formula (II-4) with NH$_4$OAc, thereby yielding a compound of Formula (II-5):

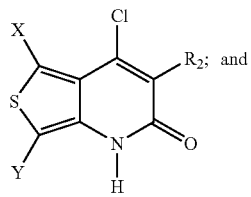

Formula (II-5)

reacting the compound of Formula (II-5) with a compound of Formula (I-6):

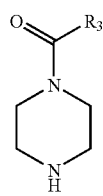

Formula (I-6)

wherein R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; thereby yielding a compound of Formula (II-7):

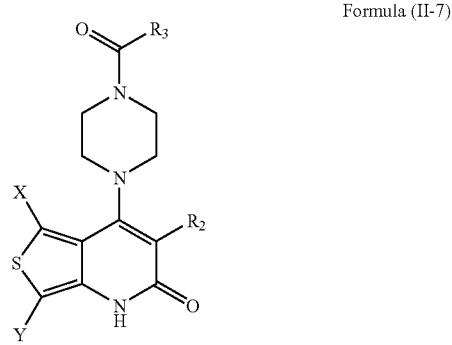

Formula (II-7)

wherein the compound of Formula (II-7) is suitable for use as a macrophage migration inhibitory factor inhibitor.

In a fourteenth aspect, a process is provided for preparing a compound of Formula (II-8) suitable for use as a macrophage migration inhibitory factor inhibitor, the process comprising the steps of reacting a compound of Formula (II-7):

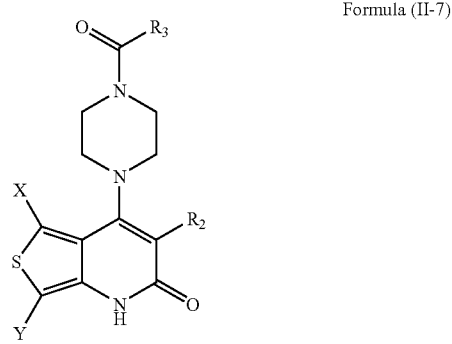

Formula (II-7)

wherein R$_2$ is —NO, —NO$_2$, —CONH$_2$, —C(=O)—NH(C$_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); wherein R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; with a compound having the formula R$_1$-Z, wherein R$_1$ is hydrogen, C$_{1-8}$ alkyl, —(CH$_2$)$_x$—(C$_{6-18}$ aryl), or —(CH$_2$)$_x$-(5-7 membered heterocycle), wherein x is 0 to 4, and wherein R$_1$ is unsubstituted or substituted with at least one of halogen, keto, C$_{1-6}$ alkyl, C$_{1-6}$ alkoxy, C$_{1-6}$ alkylamino, or di-(C$_{1-6}$ alkyl)amino, and wherein Z is Cl, Br, I, or B(OH)$_2$, thereby yielding a compound of Formula (II-8):

Formula (II-8)

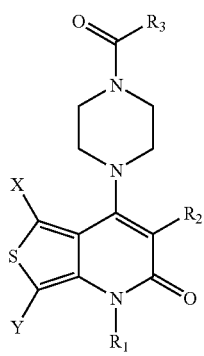

wherein the compound of Formula (II-8) is suitable for use as a macrophage migration inhibitory factor inhibitor.

In a fifteenth aspect, a process is provided for preparing a compound of Formula (II-7) suitable for use as a macrophage migration inhibitory factor inhibitor, the process comprising the steps of reacting a compound of Formula (II-5):

Formula (II-5)

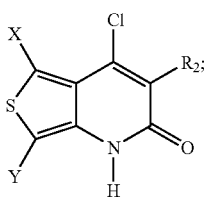

wherein $R_2$ is —NO, —NO$_2$, —CONH$_2$, —C(=O)—NH(C$_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; with a compound of Formula (I-9):

Formula (I-9)

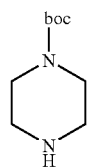

wherein boc is t-butyloxycarbonyl, thereby yielding a compound of Formula (II-10):

Formula (II-10)

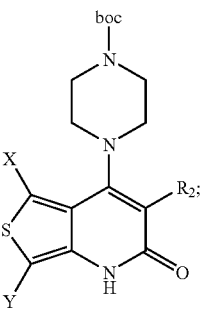

reacting the compound of Formula (II-10) with a compound having the formula R$_1$-Z, wherein R$_1$ is hydrogen, C$_{1-8}$ alkyl, —(CH$_2$)$_x$—(C$_{6-18}$ aryl), or —(CH$_2$)$_x$-(5-7 membered heterocycle), wherein x is 0 to 4, and wherein R$_1$ is unsubstituted or substituted with at least one of halogen, keto, C$_{1-6}$ alkyl, C$_{1-6}$ alkoxy, C$_{1-6}$ alkylamino, or di-(C$_{1-6}$ alkyl)amino, and wherein Z is Cl, Br, I, or B(OH)$_2$, thereby yielding a compound of Formula (II-11):

Formula (II-11)

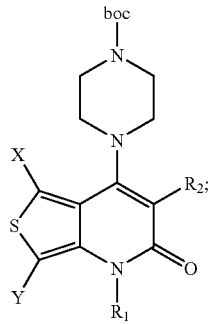

reacting the compound of Formula (II-11) with trifluoroacetic acid to yield a compound of Formula (II-12):

Formula (II-12)

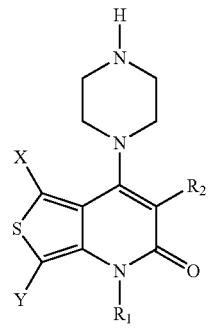

reacting the compound of Formula (II-12) with R$_3$—C(=O)-Z, wherein Z is Cl, Br, or I, or wherein R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; whereby a compound of Formula (II-8) is obtained:

Formula (II-8)

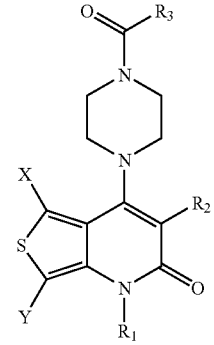

wherein the compound of Formula (II-8) is suitable for use as a macrophage migration inhibitory factor inhibitor.

In a sixteenth aspect, a process is provided for preparing a compound of Formula (II-7a) suitable for use as a macrophage migration inhibitory factor inhibitor, the process comprising the steps of reacting methylcyanoacetate with a compound of Formula (II-13):

Formula (II-13)

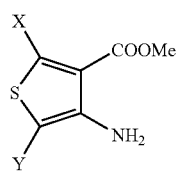

wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; to yield a compound of Formula (II-14):

Formula (II-14)

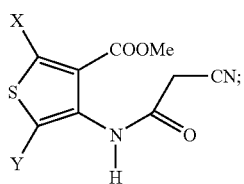

reacting NaOEt with the compound of Formula (II-14) to yield a compound of Formula (II-3a):

Formula (II-3a)

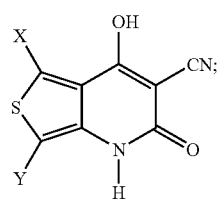

reacting the compound of Formula (II-3a) with $POCl_3$, thereby yielding a compound of Formula (II-5a):

Formula (II-5a)

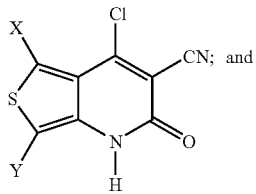

reacting the compound of Formula (II-5a) with a compound of Formula (I-6):

Formula (I-6)

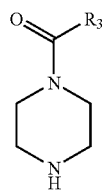

wherein $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl) amino; thereby yielding a compound of Formula (II-7a):

Formula (II-7a)

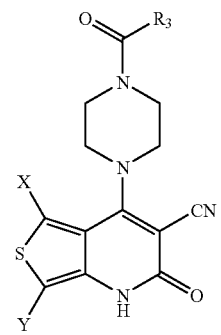

wherein the compound of Formula (II-7a) is suitable for use as a macrophage migration inhibitory factor inhibitor.

In a seventeenth aspect, a process is provided for preparing a compound of Formula (II-8a) suitable for use as a macrophage migration inhibitory factor inhibitor, the process comprising the steps of reacting a compound of Formula (II-7a):

Formula (II-7a)

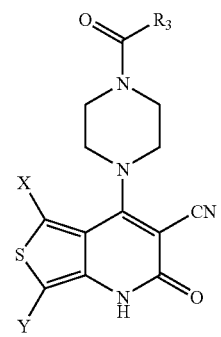

wherein $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl) amino; wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; with a compound having the formula $R_1$-Z, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; and Z is Cl, Br, I, or $B(OH)_2$, thereby yielding a compound of Formula (II-8a):

Formula (II-8a)

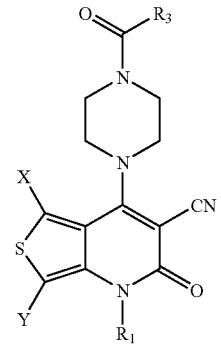

wherein the compound of Formula (II-8a) is suitable for use as a macrophage migration inhibitory factor inhibitor.

In a eighteenth aspect, a process is provided for preparing a compound of Formula (II-8a) suitable for use as a macrophage migration inhibitory factor inhibitor, the process comprising the steps of reacting a compound of Formula (II-5a):

Formula (II-5a)

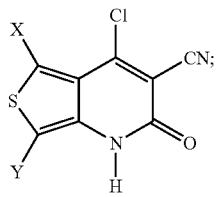

wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; with a compound of Formula (I-9):

Formula (I-9)

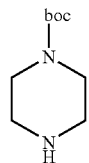

wherein boc is t-butyloxycarbonyl, thereby yielding a compound of Formula (II-10):

Formula (II-10a)

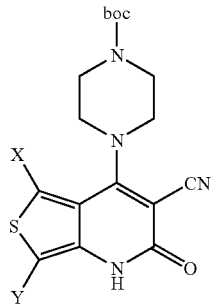

reacting the compound of Formula (II-10) with a compound having the formula $R_1$-Z, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; and wherein Z is Cl, Br, I, or $B(OH)_2$, thereby yielding a compound of Formula (II-11a):

Formula (II-11a)

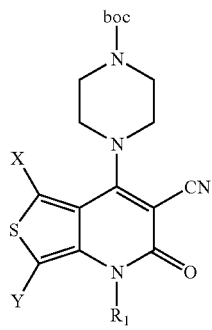

reacting the compound of Formula (II-11a) with trifluoroacetic acid to yield a compound of Formula (II-12a):

Formula (II-12a)

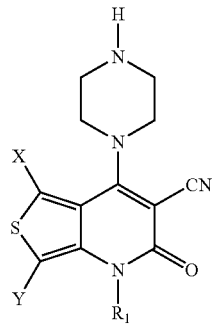

reacting the compound of Formula (II-12a) with $R_3$—C(=O)-Z, wherein Z is Cl, Br, or I, or wherein $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—$(C_{1-6}$ alkyl), —CN, —C(=O)O—$(C_{1-6}$ alkyl), —OC(=O)—$(C_{1-6}$ alkyl), keto, $C_{1-6}$ alkyl, $C_{1-6}$ alkoxy, $C_{1-6}$ alkylamino, or di-($C_{1-6}$ alkyl)amino, whereby a compound of Formula (II-8a) is obtained:

Formula (II-8a)

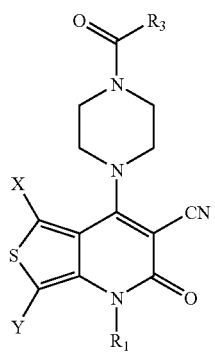

wherein the compound of Formula (II-8) is suitable for use as a macrophage migration inhibitory factor inhibitor.

In a nineteenth aspect, a process is provided for preparing a compound of Formula (III-7) suitable for use as a macrophage migration inhibitory factor inhibitor, the process comprising the steps of reacting $POCl_3$ with a compound of Formula (III-3):

Formula (III-3)

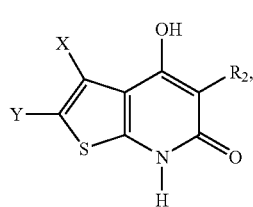

wherein $R_2$ is —NO, —$NO_2$, —$CONH_2$, —C(=O)—NH($C_{1-6}$ alkyl), —C(=O)—N($C_{1-6}$ alkyl)$_2$, —C(=O)—NH-(5-7 membered heterocycle), —C(=O)-(5-7 membered heterocycle), —C(=O)—N[$(CH_2)_2$]$_2$N—$CH_3$, —C(=O)—($C_{1-6}$ alkyl), —CN, —C(=O)O—($C_{1-6}$ alkyl), or —OC(=O)—($C_{1-6}$ alkyl); wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; thereby yielding a compound of Formula (III-4):

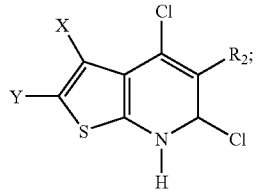

Formula (III-4)

reacting the compound of Formula (III-4) with NH₄OAc, thereby yielding a compound of Formula (III-5):

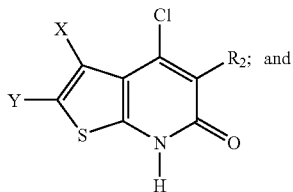

Formula (III-5)

reacting the compound of Formula (III-5) with a compound of Formula (I-6):

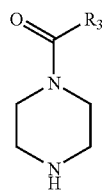

Formula (I-6)

wherein $R_3$ is $C_{1-8}$ alkyl, —$(CH_2)_y$—$(C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; thereby yielding a compound of Formula (III-7):

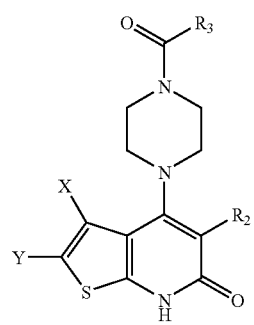

Formula (III-7)

wherein the compound of Formula (III-7) is suitable for use as a macrophage migration inhibitory factor inhibitor.

In a twentieth aspect, a process is provided for preparing a compound of Formula (III-8) suitable for use as a macrophage migration inhibitory factor inhibitor, the process comprising the steps of reacting a compound of Formula (III-7):

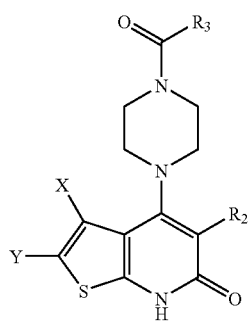

Formula (III-7)

wherein $R_2$ is —NO, —NO₂, —CONH₂, —C(=O)—NH($C_{1-6}$ alkyl), —C(=O)—N($C_{1-6}$ alkyl)₂, —C(=O)—NH-(5-7 membered heterocycle), —C(=O)-(5-7 membered heterocycle), —C(=O)—N[(CH₂)₂]₂N—CH₃, —C(=O)—($C_{1-6}$ alkyl), —CN, —C(=O)O—($C_{1-6}$ alkyl), or —OC(=O)—($C_{1-6}$ alkyl); wherein $R_3$ is $C_{1-8}$ alkyl, —$(CH_2)_y$—($C_{6-18}$ aryl), or —$(CH_2)_y$-(5-7 membered heterocycle), wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; with a compound having the formula $R_1$-Z, wherein $R_1$ is hydrogen, $C_{1-8}$ alkyl, —$(CH_2)_x$—($C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; and wherein Z is Cl, Br, I, or B(OH)₂, thereby yielding a compound of Formula (III-8):

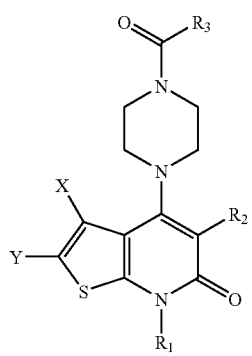

Formula (III-8)

wherein the compound of Formula (III-8) is suitable for use as a macrophage migration inhibitory factor inhibitor.

In a twenty-first aspect, a process is provided for preparing a compound of Formula (III-7) suitable for use as a macrophage migration inhibitory factor inhibitor, the process comprising the steps of reacting a compound of Formula (III-5):

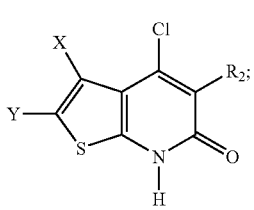

Formula (III-5)

wherein $R_2$ is —NO, —NO$_2$, —CONH$_2$, —C(=O)—NH(C$_{1-6}$ alkyl), —C(=O)—N(C$_{1-6}$ alkyl)$_2$, —C(=O)—NH-(5-7 membered heterocycle), —C(=O)-(5-7 membered heterocycle), —C(=O)—N[(CH$_2$)$_2$]$_2$N—CH$_3$, —C(=O)—(C$_{1-6}$ alkyl), —CN, —C(=O)O—(C$_{1-6}$ alkyl), or —OC(=O)—(C$_{1-6}$ alkyl); wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; with a compound of Formula (I-9):

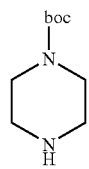

(Formula I-9)

wherein boc is t-butyloxycarbonyl, thereby yielding a compound of Formula (III-10):

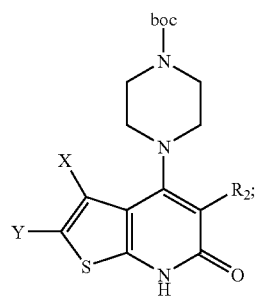

Formula (III-10)

reacting the compound of Formula (III-10) with a compound having the formula $R_1$-Z, wherein $R_1$ is hydrogen, C$_{1-8}$ alkyl, —(CH$_2$)$_x$—(C$_{6-18}$ aryl), or —(CH$_2$)$_x$-(5-7 membered heterocycle), wherein x is 0 to 4, and wherein $R_1$ is unsubstituted or substituted with at least one of halogen, keto, C$_{1-6}$ alkyl, C$_{1-6}$ alkoxy, C$_{1-6}$ alkylamino, or di-(C$_{1-6}$ alkyl)amino; and wherein Z is Cl, Br, I, or B(OH)$_2$, thereby yielding a compound of Formula (III-11):

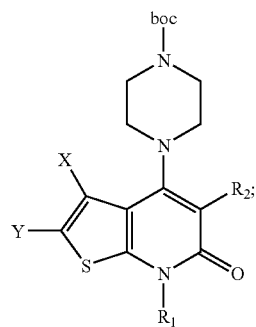

Formula (III-11)

reacting the compound of Formula (III-11) with trifluoroacetic acid to yield a compound of Formula (III-12):

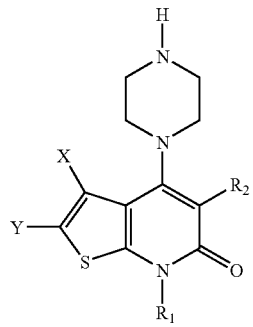

Formula (III-12)

reacting the compound of Formula (III-12) with $R_3$—C(=O)-Z, wherein Z is Cl, Br, or I, or wherein $R_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein $R_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl)amino; whereby a compound of Formula (III-8) is obtained:

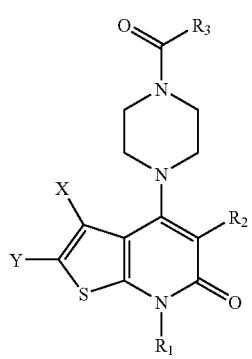

Formula (III-8)

wherein the compound of Formula (III-8) is suitable for use as a macrophage migration inhibitory factor inhibitor.

In a twenty-second aspect, a process is provided for preparing a compound of Formula (III-7a) suitable for use as a macrophage migration inhibitory factor inhibitor, the process comprising the steps of:

reacting methylcyanoacetate with a compound of Formula (III-13):

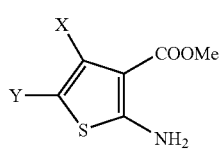

Formula (III-13)

wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; to yield a compound of Formula (III-14):

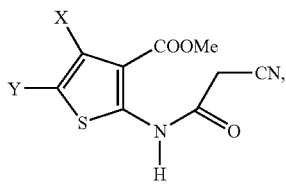

Formula (III-14)

reacting NaOEt with the compound of Formula (III-14) to yield a compound of Formula (III-3a):

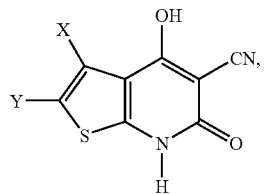

Formula (III-3a)

reacting the compound of Formula (III-3a) with POCl$_3$, thereby yielding a compound of Formula (III-5a):

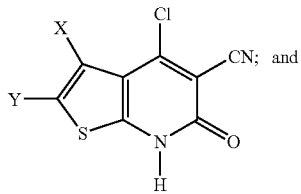

Formula (III-5a); and reacting the compound of Formula (III-5a) with a compound of Formula (I-6):

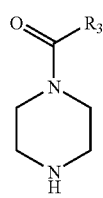

Formula (I-6)

wherein R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl) amino; thereby yielding a compound of Formula (III-7a):

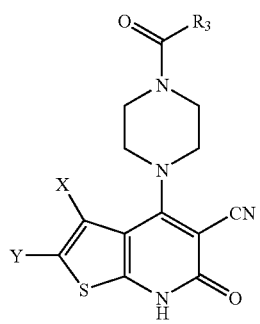

Formula (III-7a)

wherein the compound of Formula (III-7a) is suitable for use as a macrophage migration inhibitory factor inhibitor.

In a twenty-third aspect, a process is provided for preparing a compound of Formula (III-8a) suitable for use as a macrophage migration inhibitory factor inhibitor, the process comprising the steps of reacting a compound of Formula (III-7a):

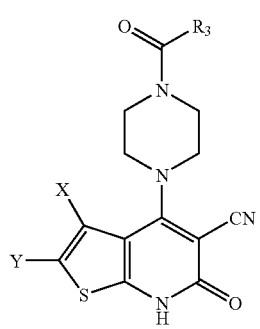

Formula (III-7a)

wherein R$_3$ is C$_{1-8}$ alkyl, —(CH$_2$)$_y$—(C$_{6-18}$ aryl), or —(CH$_2$)$_y$-(5-7 membered heterocycle), wherein y is 0 to 4, and wherein R$_3$ is unsubstituted or substituted with at least one of halogen, hydroxy, —C(=O)—(C$_{1-6}$ alkyl), —CN, —C(=O)O—(C$_{1-6}$ alkyl), —OC(=O)—(C$_{1-6}$ alkyl), keto, C$_{1-6}$ alkyl, C$_{1-6}$ alkoxy, C$_{1-6}$ alkylamino, or di-(C$_{1-6}$ alkyl) amino; wherein X is hydrogen, halogen, C$_{1-6}$ alkyl, C$_{1-6}$ alkoxy, C$_{1-6}$ alkylamino, or di-(C$_{1-6}$ alkyl)amino; and wherein Y is hydrogen, halogen, C$_{1-6}$ alkyl, C$_{1-6}$ alkoxy, C$_{1-6}$ alkylamino, or di-(C$_{1-6}$ alkyl)amino; with a compound having the formula R$_1$-Z, wherein R$_1$ is hydrogen, C$_{1-8}$ alkyl, —(CH$_2$)$_x$—(C$_{6-18}$ aryl), or —(CH$_2$)$_x$-(5-7 membered heterocycle), wherein x is 0 to 4, and wherein R$_1$ is unsubstituted or substituted with at least one of halogen, keto, C$_{1-6}$ alkyl, C$_{1-6}$ alkoxy, C$_{1-6}$ alkylamino, or di-(C$_{1-6}$ alkyl)amino; and Z is Cl, Br, I, or B(OH)$_2$, thereby yielding a compound of Formula (III-8a):

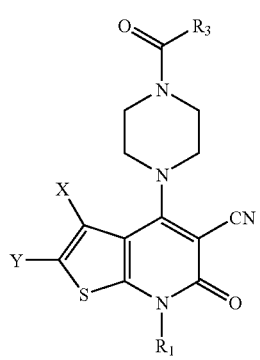

Formula (III-8a)

wherein the compound of Formula (III-8a) is suitable for use as a macrophage migration inhibitory factor inhibitor.

In a twenty-fourth aspect, a process is provided for preparing a compound of Formula (III-8a) suitable for use as a macrophage migration inhibitory factor inhibitor, the process comprising the steps of reacting a compound of Formula (III-5a):

Formula (III-5a)

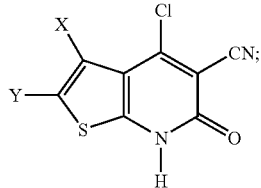

wherein X is hydrogen, halogen, $C_{1-6}$ alkyl, $C_{1-6}$ alkoxy, $C_{1-6}$ alkylamino, or di-($C_{1-6}$ alkyl)amino; and wherein Y is hydrogen, halogen, $C_{1-6}$ alkyl, $C_{1-6}$ alkoxy, $C_{1-6}$ alkylamino, or di-($C_{1-6}$ alkyl)amino; with a compound of Formula (I-9):

Formula (I-9)

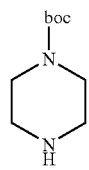

wherein boc is t-butyloxycarbonyl, thereby yielding a compound of Formula (III-10):

Formula (III-10a)

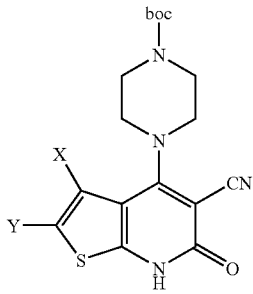

reacting the compound of Formula (III-10) with a compound having the formula $R_1$-Z, wherein $R_1$ is hydrogen, $C_{1-8}$ alkyl, —$(CH_2)_x$—$(C_{6-18}$ aryl), or —$(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-($C_{1-6}$ alkyl)amino; and wherein Z is Cl, Br, I, or B(OH)$_2$, thereby yielding a compound of Formula (III-11a):

Formula (III-11a)

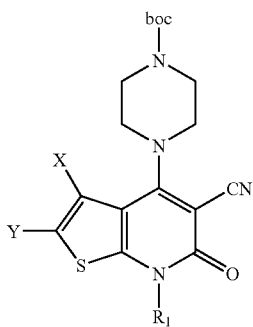

reacting the compound of Formula (III-11a) with trifluoroacetic acid to yield a compound of Formula (III-12a):

Formula (III-12a)

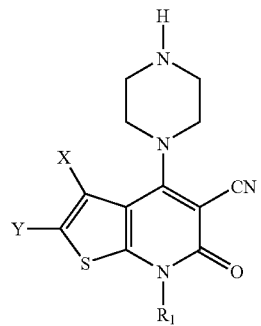

reacting the compound of Formula (III-12a) with $R_3$—C(=O)-Z, wherein Z is Cl, Br, or I, and wherein $R_3$ is $C_{1-8}$ alkyl, —$(CH_2)_y$-$(C_{6-18}$ aryl), or —$(CH_2)_y$-(5-7 membered heterocycle) wherein y is 0 to 4, and wherein $R_3$ is unsubstituted or substituted with at least one of halogen, hydroxy, —C(=O)—($C_{1-6}$ alkyl), —CN, —C(=O)O—($C_{1-6}$ alkyl), —OC(=O)—($C_{1-6}$ alkyl), keto, $C_{1-6}$ alkyl, $C_{1-6}$ alkoxy, $C_{1-6}$ alkylamino, or di-($C_{1-6}$ alkyl)amino; whereby a compound of Formula (III-8a) is obtained:

Formula (III-8a)

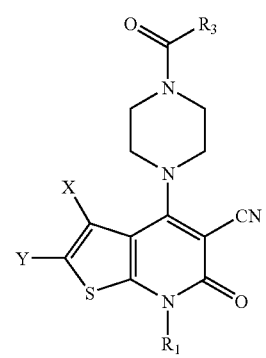

wherein the compound of Formula (III-8) is suitable for use as a macrophage migration inhibitory factor inhibitor.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

As an aid to understanding the preferred embodiments, certain definitions are provided herein.

The terms "macrophage migration inhibitory activity" "MIF activity" as used herein is a broad term, and is to be given its ordinary and customary meaning to a person of ordinary skill in the art (and is not to be limited to a special or customized meaning), and refers without limitation to an activity or effect mediated at least in part by macrophage migration inhibitory factor. Accordingly, MIF activity includes, but is not limited to, inhibition of macrophage migration, tautomerase activity (e.g., using phenylpyruvate or dopachrome), endotoxin induced shock, inflammation, glucocorticoid counter regulation, induction of thymidine incorporation into 3T3 fibroblasts, induction of erk phosphorylation and MAP kinase activity.

The term "inhibitor" as used herein is a broad term, and is to be given its ordinary and customary meaning to a person of ordinary skill in the art (and is not to be limited to a special or customized meaning), and refers without limitation to a molecule (e.g., natural or synthetic compound) that can alter the conformation of MIF and/or compete with a monoclonal antibody to MIF and decrease at least one activity of MIF or its export from a cell as compared to activity or export in the absence of the inhibitor. In other words, an "inhibitor" alters conformation and/or activity and/or export if there is a statistically significant change in the amount of MIF measured, MIF activity, or in MIF protein detected extracellularly and/or intracellularly in an assay performed with an inhibitor, compared to the assay performed without the inhibitor.

In general, MIF inhibitors inhibit the physiological function of MIF, and thus are useful in the treatment of diseases where MIF may be pathogenic.

In certain of the preferred embodiments, MIF inhibitors are provided that are thienopyridinone derivatives having the following structures (I), (II), and (III):

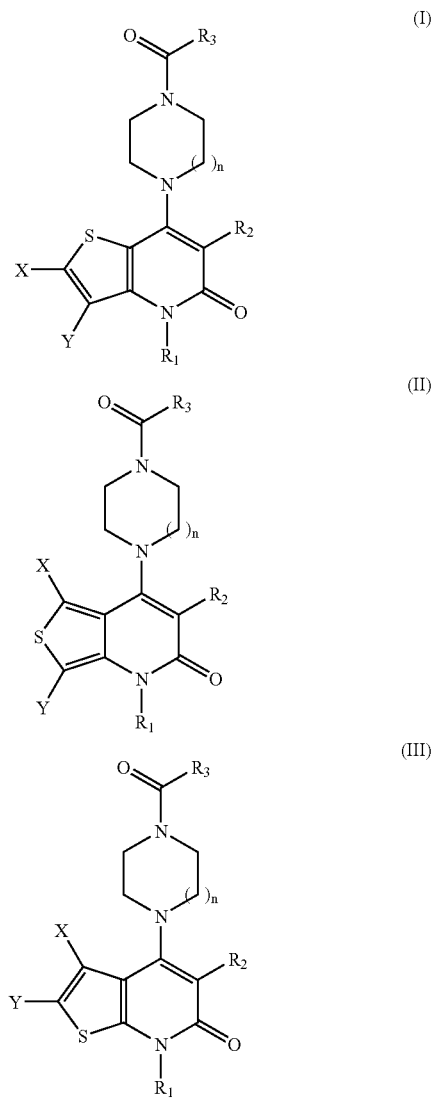

including forms such as stereoisomers, free forms, pharmaceutically acceptable salts or esters thereof, solvates, and combinations of such forms; wherein $R_1$ is hydrogen, $C_{1-8}$ alkyl, $-(CH_2)_x-(C_{6-18}$ aryl), or $-(CH_2)_x$-(5-7 membered heterocycle), wherein x is 0 to 4, and wherein $R_1$ is unsubstituted or substituted with at least one of halogen, keto, $C_{1-6}$ alkyl, $C_{1-6}$ alkoxy, $C_{1-6}$ alkylamino, or di-$(C_{1-6}$ alkyl)amino; $R_2$ is $-CN$, $-NO$, $-NO_2$, $-CONH_2$, $-C(=O)-NH$ $(C_{1-6}$ alkyl), $-C(=O)-N(C_{1-6}$ alkyl$)_2$, $-C(=O)-NH$-(5-7 membered heterocycle), $-C(=O)$-(5-7 membered heterocycle), $-C(=O)-N[(CH_2)_2]_2N-CH_3$, $-C(=O)-$ $(C_{1-6}$ alkyl), $-C(=O)O-(C_{1-6}$ alkyl), or $-OC(=O)-$ $(C_{1-6}$ alkyl); $R_3$ is $C_{1-8}$ alkyl, $-(CH_2)_y-(C_{6-18}$ aryl), or $-(CH_2)_y$-(5-7 membered heterocycle), wherein y is 0 to 4, and wherein $R_3$ is unsubstituted or substituted with at least one of halogen, hydroxy, $-C(=O)-(C_{1-6}$ alkyl), $-CN$, $-C(=O)O-(C_{1-6}$ alkyl), $-OC(=O)-(C_{1-6}$ alkyl), keto, $C_{1-6}$ alkyl, $C_{1-6}$ alkoxy, $C_{1-6}$ alkylamino, or di-$(C_{1-6}$ alkyl)amino; X is hydrogen, halogen, $C_{1-6}$ alkyl, $C_{1-6}$ alkoxy, $C_{1-6}$ alkylamino, or di-$(C_{1-6}$ alkyl)amino; Y is hydrogen, halogen, $C_{1-6}$ alkyl, $C_{1-6}$ alkoxy, $C_{1-6}$ alkylamino, or di-$(C_{1-6}$ alkyl) amino; and n is 0, 1, or 2.

In a preferred embodiment, methods are provided for reducing MIF activity in a patient in need thereof by administering to the patient an effective amount of a compound having the following structures (I), (II), and (III):

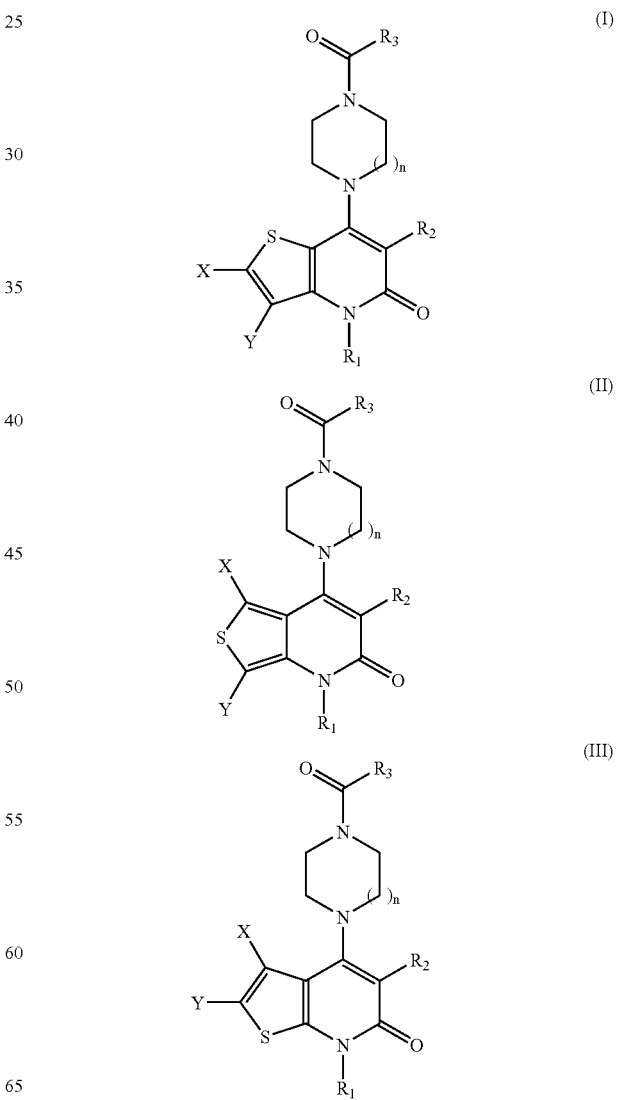

including forms such as stereoisomers, free forms, pharmaceutically acceptable salts, or esters thereof, solvates, and combinations of such forms; wherein n, $R_1$, $R_2$, $R_3$, X, and Y are as defined above.

As used herein, the above terms have the following meanings. The term "alkl," as used herein is a broad term and is used in its ordinary sense, including, without limitation, to refer to a straight chain or branched, acyclic or cyclic, unsaturated or saturated aliphatic hydrocarbon containing 1, 2, 3, 4, 5, 6, 7, or 8 or more carbon atoms (e.g, $C_{1-8}$ alkyl), while the term "lower alkyl" has the same meaning as alkyl but contains 1, 2, 3, 4, 5, or 6 carbon atoms (e.g., $C_{1-6}$ alkyl). Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl," respectively).

The term "cycloalkyl," as used herein is a broad term and is used in its ordinary sense, including, without limitation, to refer to alkyls that include mono-, di-, or poly-homocyclic alkyl ring systems. Cycloalkyls are also referred to as "cyclic alkyls" or "homocyclic rings." Representative cycloalkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, cyclopentenyl, cyclohexenyl, decalin, and adamantane.

The term "aryl," as used herein is a broad term and is used in its ordinary sense, including, without limitation, to refer to an aromatic carbocyclic moiety such as phenyl or naphthyl, including mono-, di-, and poly-homocyclic aromatic ring systems (e.g., $C_{6-18}$ aryl).

The term "arylalkyl," as used herein is a broad term and is used in its ordinary sense, including, without limitation, to refer to an alkyl having at least one alkyl hydrogen atom replaced with an aryl moiety, such as benzyl or naphthyl. Representative arylalkyls include —$CH_2$-(1-naphthyl), —$CH_2$-(2-naphthyl), —$CH_2$-(phenyl), —$(CH_2)_2$-(phenyl), —$(CH_2)_3$-(phenyl), and —$CH$-(phenyl)$_2$.

The terms "heterocycle" and "heterocyclic ring," as used herein, are broad terms and are used in their ordinary sense, including, without limitation, to refer to a 5, 6, or 7 membered monocyclic heterocyclic ring, or a 7, 8, 9, 10, 11, 12, 13, or 14 or more membered polycyclic heterocyclic ring. The ring can be saturated, unsaturated, aromatic (e.g., a heteroaryl), or nonaromatic, and can contain 1, 2, 3, or 4 or more heteroatoms independently selected from nitrogen, oxygen, and sulfur. The nitrogen and sulfur heteroatoms can be optionally oxidized, and the nitrogen heteroatom can be optionally quaternized, including bicyclic rings in which any of the above heterocycles are fused to (or anellated with, spiro-linked to, or bridged to) a phenyl or naphthyl ring as well as tricyclic (and higher) homocyclic or heterocyclic ring systems. The heterocycle can be attached to the remainder of the molecule via any heteroatom or carbon atom of the ring or rings. Representative heteroaryls include furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Representative heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Also included are heterocycles of the following structures:

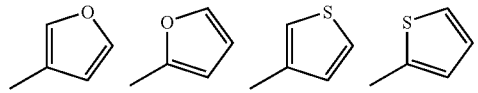

The term "heterocyclealkyl," as used herein is a broad term and is used in its ordinary sense, including, without limitation, to refer to an alkyl having at least one alkyl hydrogen atom replaced with a heterocycle, such as —$CH_2$-morpholinyl, and the like.

The term "substituted," as used herein is a broad term and is used in its ordinary sense, including, without limitation, to refer to any of the above groups (e.g, alkyl, aryl, arylalkyl, heterocycle, or heterocyclealkyl) wherein at least one hydrogen atom is replaced with a substituent. In the case of a keto substituent (i.e., —C(=O)—) two hydrogen atoms are replaced. Representative substituents within the context of preferred embodiments include halogen, hydroxy, cyano, nitro, amino, alkylamino, dialkylamino, alkyl, alkoxy, alkylthio, aryl, and heterocycle. Particularly preferred substituents include halogen, $C_{1-6}$ alkyl, $C_{1-6}$ alkoxy, $C_{1-6}$ alkylamino, and di-($C_{1-6}$ alkyl)amino.

The term "halogen," as used herein is a broad term and is used in its ordinary sense, including, without limitation, to refer to fluoro (F), chloro (Cl), bromo (Br), and iodo (I).

The term "alkoxy," as used herein is a broad term and is used in its ordinary sense, including, without limitation, to refer to an alkyl moiety attached through an oxygen bridge (i.e., —O-alkyl) such as methoxy, ethoxy, and the like.

The terms "alkylamino" and "dialkylamino" as used herein, are broad terms and are used in their ordinary sense, including, without limitation, to refer to one alkyl moiety or two alkyl moieties, respectively, attached through a nitrogen bridge (e.g, —N-(alkyl)$_2$ or —N-alkyl). Representative alkylamino and dialkylamino groups include methylamino, ethylamino, dimethylamino, diethylamino, and the like.

The cyclic systems referred to herein include fused ring, bridged ring, and spiro ring moieties, in addition to isolated monocyclic moieties.

MIF as a Drug Target

Macrophage migration inhibitory factor (MIF) is well suited for analysis as a drug target as its activity has been implicated in a variety of pathophysiological conditions. For instance, MIF has been shown to be a significant mediator in both inflammatory responses and cellular proliferation. In this regard, MIF has been shown to play roles as a cytokine, a pituitary hormone, as glucocorticoid-induced immunomodulator, and as a neuroimmunomodulator and in neuronal function. Takahashi et al., *Mol. Med.* 4:707-714, 1998; Bucala, *Ann. N.Y. Acad. Sci.* 840:74-82, 1998; Bacher et al., *Mol. Med.* 4(4):217-230, 1998. Further, it has been recently demonstrated that anti-MIF antibodies have a variety of uses, notably decreased tumor growth, along with an observed reduction in angiogenesis. Ogawa et al., *Cytokine* 12(4):309-314, 2000; Metz and Bucala (supra). Accordingly, small molecules that can inhibit MIF have significant value in the treatment of inflammatory responses, reduction of angiogenesis, viral infection, bacterial infection, treatment of cancer (specifically tumorigenesis and apoptosis), treatment of graft versus host disease and associated tissue rejection. A MIF inhibitor may be particularly useful in a variety of immune related responses, tumor growth, glomerulonephritis, inflammation, malarial anemia, septic shock, tumor associated angiogenesis, vitreoretinopathy, psoriasis, graft versus host disease (tissue rejection), atopic dermatitis, rheumatoid arthritis, inflammatory bowel disease, inflammatory lung disorders, otitis media, Crohn's disease, acute respiratory distress syndrome, delayed-type hypersensitivity. A MIF inhibitor may also be useful in the treatment of stress and glucocorticoid function disorders, e.g., counter regulation of glucocorticoid action; or overriding of glucocorticoid mediated suppression of arachidonate release (Cys-60 based catalytic MIF oxidoreductase activity or JAB1/CSNS-MIF-interaction based mechanism). MIF inhibitors may also be useful in the treatment of systemic lupus erythematosus (SLE). MIF mRNA expression in peripheral blood mononuclear cells (PBMC) and serum MIF concentration is significantly increased in patients with SLE and correlates with SLE disease activity. See Chen et al., Zhonghua Nei Ke Za Zhi. 2004 August; 43(8):572-5.

While not wishing to be limited to any particular theory of operation, MIF may likely be produced by activated T-cells and macrophages during the proinflammatory stage of endotoxin-induced shock, e.g., as part of the localized response to infection. Once released by a pro-inflammatory stimulus, e.g., low concentrations of LPS, or by TNF-α and IFN-γ, macrophage-derived MIF may be the probable source of MIF produced during the acute phase of endotoxic shock. Both the pituitary, which releases MIF in response to LPS, and macrophages are the probable source of MIF in the post-acute phase of endotoxic shock, when the infection is no longer confined to a localized site. See, e.g., U.S. Pat. No. 6,080,407, incorporated herein by reference in its entirety and describing these results with anti-MIF antibodies.

A variety of inflammatory conditions may be amenable to treatment with a MIF inhibitor. In this regard, among other advantages, the inhibition of MIF activity and/or release may be employed to treat inflammatory response and shock. Beneficial effects may be achieved by intervention at both early and late stages of the shock response. In this respect, while not limited to any theory or mechanism responsible for the protective effect of MIF inhibition, anti-MIF studies have demonstrated that introduction of anti-MIF antibodies is associated with an appreciable (up to 35-40%) reduction in circulating serum TNF-α levels. This reduction is consistent with the TNF-α-inducing activity of MIF on macrophages in vitro, and suggests that MIF may be responsible, in part, for the extremely high peak in serum TNF-α level that occurs 1-2 hours after endotoxin administration despite the fact that MIF cannot be detected in the circulation at this time. Thus, MIF inhibition therapy may be beneficial at the early stages of the inflammatory response.

MIF also plays a role during the post-acute stage of the shock response, and therefore, offers an opportunity to intervene at late stages where other treatments, such as anti-TNF-α therapy, are ineffective. Inhibition of MIF can protect against lethal shock in animals challenged with high concentrations of endotoxin (i.e., concentrations that induce release of pituitary MIF into the circulation), and in animals challenged with TNF-α. Accordingly, the ability to inhibit MIF and protect animals challenged with TNF indicates that neutralization of MIF during the later, post-acute phase of septic shock may be efficacious.

As evidenced herein, TNF-α and IL-1β levels are correlated at least in some instances to MIF levels. Accordingly, an anti-MIF small molecule may be useful in a variety of TNF-α and/or IL-1β associated disease states including transplant rejection, immune-mediated and inflammatory elements of CNS disease (e.g., Alzheimer's, Parkinson's, multiple sclerosis, and the like), muscular dystrophy, diseases of hemostasis (e.g, coagulopathy, veno occlusive diseases, and the like), allergic neuritis, granuloma, diabetes, graft versus host disease, chronic renal damage, alopecia (hair loss), acute pancreatitis, joint disease, congestive heart failure, cardiovascular disease (restenosis, atherosclerosis), joint disease, and osteoarthritis. See also Colby-Germinario, et al., J. Neurological Sci., 1977, 33:111-129; Sheremata, et al., J. Neurological Sci., 1978, 36:165-170; Wettinger, et al., Blood. 2005 Mar. 1; 105(5):2000-6. Epub 2004 Nov. 02; and "Chemists say they have identified a gene that appears to play a key role in the development of type 1 diabetes," Medical Research News, Published: Monday, 21 Mar. 2005, www.news-medical.net.htm.

Further, additional evidence in the art has indicated that steroids, while potent inhibitors of cytokine production, actually increase MIF expression. Yang et al., Mol. Med. 4(6):413-424, 1998; Mitchell et al., J. Biol. Chem. 274(25): 18100-18106, 1999; Calandra and Bucala, Crit. Rev. Immunol. 17(1):77-88, 1997; Bucala, FASEB J. 10(14):1607-1613, 1996. Accordingly, it may be of particular utility to utilize MIF inhibitors in combination with steroidal therapy for the treatment of cytokine mediated pathophysiological conditions, such as inflammation, shock, and other cytokine-mediated pathological states, particularly in chronic inflammatory states such as arthritis, particularly rheumatoid arthritis. Such combination therapy may be beneficial even subsequent to the onset of pathogenic or other inflammatory responses. For example, in the clinical setting, the administration of steroids subsequent to the onset of septic shock symptoms has proven of little benefit. See Bone et al., N. Engl. J. Med. 317: 653-658, 1987; Spring et al., N. Engl. J. Med. 311: 1137-1141, 1984. Combination steroid/MIF inhibition therapy may be employed to overcome this obstacle. Further, one of skill in the art may understand that such therapies may be tailored to inhibit MIF release and/or activity locally and/or systemically.

Applications and Methods Utilizing MIF Inhibitors

MIF inhibitors have a variety of applicable uses, as noted above. Candidate MIF inhibitors may be isolated or procured from a variety of sources, such as bacteria, fungi, plants, parasites, libraries of chemicals (small molecules), peptides or peptide derivatives and the like. Further, one of skill in the art will recognize that inhibition has occurred when a statistically significant variation from control levels is observed.

Given the various roles of MIF in pathology and homeostasis, inhibition of MIF activity or MIF extracellular localization may have a therapeutic effect. For example, recent studies have demonstrated that MIF is a mediator of endotoxemia, where anti-MIF antibodies fully protected mice from LPS-induced lethality. See Bernhagen et al., Nature 365:756-759, 1993; Calandra et al., J. Exp. Med. 179:1895-1902, 1994; Bernhagen et al., Trends Microbiol. 2:198-201, 1994. Further, anti-MIF antibodies have markedly increased survival in mice challenged with gram-positive bacteria that induces septic shock. Bernhagen et al., J. Mol. Med. 76:151-161, 1998. Other studies have demonstrated the role of MIF in tumor cell growth and that anti-sense inhibition of MIF leads to resistance to apoptotic stimuli. Takahashi et al., Mol. Med. 4:707-714, 1998; Takahashi et al., Microbiol. Immunol. 43(1):61-67, 1999. In addition, the finding that MIF is a counterregulator of glucocorticoid action indicates that methods of inhibiting MIF extracellular localization may allow for treatment of a variety of pathological conditions, including autoimmunity, inflammation, endotoxemia, and adult respiratory distress syndrome, inflammatory bowel disease, otitis media, inflammatory joint disease and Crohn's disease. Bernhagen et al., *J. Mol. Med.* 76:151-161, 1998; Calandra et al., *Nature* 377:68-71, 1995; Donnelly et al., *Nat. Med.* 3:320-323, 1997. Because MIF is also recognized to be angiogenic, the inhibition of this cytokine may have anti-angiogenic activity and particular utility in angiogenic diseases that include, but are not limited to, cancer, diabetic retinopathy, psoriasis, inflammation of the skin, angiopathies, fertility, obesity and genetic diseases of glucocorticoid dysfunction like Cushing's and Addison's disease. MIF inhibitors may also be useful in treating conditions such as metabolic syndrome.

The compounds of the preferred embodiments can be used for the treatment of a patient that has, or is at risk for having, diabetes mellitus (e.g., type 1 diabetes, type 2 diabetes, gestational diabetes), abnormal glucose tolerance, stress hyperglycemia, metabolic syndrome, and/or insulin resistance. The compounds of preferred embodiments are especially preferred for treating a patient having or at risk for type 1 diabetes.

Type 1 diabetes mellitus is a multifactorial syndrome caused by the lack of endogenous insulin, thought to be due to an immune attack mediated by autoreactive T cells and macrophages against pancreatic p-cells. Extensive research efforts have greatly expanded understanding of disease pathogenesis, and have revealed a critical role for several pro-inflammatory mediators. However, no effective anti-inflammatory therapeutic has been approved for the clinical management of type 1 diabetes. Several animal models of the disease have enhanced understanding of the molecular events that underlie the pathogenesis of diabetes. Multiple low doses of streptozotocin to susceptible strains of mice induce a diabetic condition with many of the hallmarks of human type 1 diabetes. Clinical and histoimmunological similarities include the development of hyperglycemia associated with infiltration of the pancreatic islets by T lymphocytes and macrophages (insulitis) (Like et al., *Science* 193: 415-417, 1976; Kolb, *Diabetes Rev.* 1:116-126, 1993). Proinflammatory cytokines, including interleukin (IL)-1β, interferon (IFN)-γ, tumor necrosis factor (TNF)-α and IL-18 play important roles in the development of streptozotocin-induced diabetes (Sandberg et al., *Biochem. Biophys. Res. Comm.* 202:543-548, 1994; Herold et al., *J. Immunol.* 156: 3521-3527, 1996; Holdstad et al., *J. Autoimmun.* 16:441-447, 2001; Nicoletti et al., *Eur. J. Immunol.* 33:2278-2286, 2003). However, administration of either recombinant IL-1β, IFN-γ, or TNF-α, or specific inhibitors of their activity, have complex and often contradictory effects on disease development and/or course, depending on animal model used, as well as on timing of administration (Rabinovitch et al., *Biochem. Pharmacol.* 55: 1139-1149, 1998; Campbell et al., *J. Clin. Invest.* 87:739-740, 1991; Nicoletti et al., *Diabetes* 47:32-38, 1998; Yang et al., *J. Exp. Med.* 180:995-1004, 1994).

The key pathogenic role played by the immune system in the pathogenesis of type 1 diabetes has recently focused on identifying immunotherapeutical approaches that may allow halting or delaying β-cell destruction in prediabetic individuals or in those patients with newly diagnosed disease (Winter et al., *Biodrugs* 17:39 64, 2003). Macrophage migration inhibitory factor (MIF) is a critical cytokine in local and systemic inflammation, but its role in diabetes has not been explored thoroughly. MIF is a pleiotropic cytokine produced during immune responses by activated T cells, macrophages and a variety of nonimmune cells (Bucala, *FASEB J.* 10:1607-1613, 1996; Metz et al., *Adv. Immunol.* 66: 197-223, 1997). It acts as a critical mediator of host defense, and is being explored as a therapeutic target in septic shock as well as chronic inflammatory and autoimmune diseases (Calandra et al., *Nat. Med.* 6:164-170, 2000; De Yong et al., *Nat. Immunol.* 2:1061-1066, 2001; Denkinger et al., *J. Immunol.* 170:1274-1282, 2003). Elevated MIF gene expression has been detected in spontaneously non-obese diabetic (NOD) mice (Bojunga et al., *Cytokine* 91:179-186, 2003), but its importance in the pathogenesis of type 1 diabetes is unclear. The role of MIF in type 2 diabetes has also been investigated (Yabunaka N, et al., *Diabetes Care* 23(2):256-, 2000), as has the role of MIF in the pathogenesis of proliferative diabetic retinopathy (Mitamura Y, et al., *Br. J. Opthalmol.* 84:636-639, 2000)

A potential role for MIF in the development and pathogenesis of autoimmune mediated diabetes has been implicated in spontaneously diabetic NOD mice, because expression of MIF mRNA is significantly increased during disease development, and exogenous MIF administration increases disease incidence in these animals (Bojunga et al., *Cytokine* 91:179-186, 2003). MIF is constitutively expressed and secreted together with insulin from pancreatic p-cells, and acts as an autocrine factor to stimulate insulin release (Waeber et al., *Proc. Natl. Acad. Sci. USA* 94:4782-4787, 1997). Because induction of insulin secretion is thought to contribute to immunoinflammatory diabetogenic pathways by favoring the expression on the β-cells and the presentation to the immune cells of antigens that are up-regulated when the functional activity is augmented (Winter et al., *Biodrugs* 17:39 64, 2003), this hormonal property could represent an additional important factor involving endogenous MIF in the initial events of β-cell dysfunction and destruction. Targeting endogenous MIF may therefore be a suitable approach for unraveling the role of this cytokine in the pathogenesis of type 1 diabetes and for therapeutic and/or prophylactic treatment of the condition.

Endogenous MIF has been reported to play a role in the development of murine autoimmune diabetes (PCT International Publ. No. WO-2005/094338-A1), where progression of MLD-STZ-induced diabetes was accompanied by up-regulated MIF protein expression both in pancreatic islets and peripheral cells, and immunoneutralization of MIF by anti-MIF IgG, or pharmacological inhibition of MIF activity with ISO-1, attenuated the clinical and histological manifestations of the disease.

The MIF inhibitors activity or export may be employed therapeutically and also utilized in conjunction with a targeting moiety that binds a cell surface receptor specific to particular cells. Compositions of preferred embodiments may be formulated for administration by any conventional route, including enterally (e.g., buccal, oral, nasal, rectal), parenterally (e.g., intravenous, intracranial, intraperitoneal, subcutaneous, or intramuscular), or topically (e.g., epicutaneous, intranasal, or intratracheal). Within other embodiments, the compositions described herein may be administered as part of a sustained release implant.

Within yet other embodiments, compositions of preferred embodiments may be formulized as a lyophilizate, utilizing appropriate excipients that provide stability as a lyophilizate, and subsequent to rehydration.

Pharmaceutical compositions containing the MIF inhibitors of preferred embodiments can be manufactured according to conventional methods, e.g., by mixing, granulating, coating, dissolving or lyophilizing processes.

In another embodiment, pharmaceutical compositions containing one or more MIF inhibitors are provided. For the purposes of administration, the compounds of preferred embodiments may be formulated as pharmaceutical compositions. Pharmaceutical compositions of preferred embodiments comprise one or more MIF inhibitors of preferred embodiments and a pharmaceutically acceptable carrier and/or diluent. The inhibitor of MIF is present in the composition in an amount which is effective to treat a particular disorder, that is, in an amount sufficient to achieve decreased MIF levels or activity, symptoms, and/or preferably with acceptable toxicity to the patient. Preferably, the pharmaceutical compositions of preferred embodiments can include MIF inhibitor(s) in an amount from less than about 0.5 mg to more than about 1000 mg per dosage depending upon the route of administration, preferably from about 0.6, 0.7, 0.8, or 0.9 mg to about 150, 200, 250, 300, 350, 400, 450, 500, 600, 700, 800, or 900 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, tablets (coated or uncoated), (injectable) solutions, solid solutions, suspensions, dispersions, solid dispersions (e.g., in the form of ampoules, vials, creams, gels, pastes, inhaler powder, foams, tinctures, lipsticks, drops, sprays, or suppositories). The formulation can contain (in addition to one or more MIF inhibitors and other optional active ingredients) fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art. One skilled in this art may further formulate the inhibitor of MIF in an appropriate manner, and in accordance with accepted practices, such as those described in *Remington's Pharmaceutical Sciences*, Gennaro, Ed., Mack Publishing Co., Easton, Pa. 1990.

The compounds of structures (I), (II), and (III) may occur as isomers, racemates, optical isomers, enantiomers, diastereomers, tautomers, and cis/trans conformers. All such isomeric forms are included within preferred embodiments, including mixtures thereof The compounds of structures (I), (II), and (III) may have chiral centers, for example, they may contain asymmetric carbon atoms and may thus exist in the form of enantiomers or diastereoisomers and mixtures thereof, e.g. racemates. Any asymmetric carbon atom may be present in the (R)-, (S)- or (R,S)-configuration, preferably in the (R)- or (S)-configuration. Isomeric mixtures can be separated, as desired, according to conventional methods to obtain pure isomers.

Furthermore, some of the crystalline forms of the compounds of structures (I), (II), and (III) may exist as polymorphs, which are included in preferred embodiments. In addition, some of the compounds of structures (I), (II), and (III) may also form solvates with water or other organic solvents. Such solvates are similarly included within the scope of the preferred embodiments.

In another embodiment, a method is provided for treating a variety of disorders or illnesses, including inflammatory diseases, arthritis, immune-related disorders, and the like. Such methods include administering of a compound of preferred embodiments to a warm-blooded animal in an amount sufficient to treat the disorder or illness. Such methods include systemic administration of an inhibitor of MIF of preferred embodiments, preferably in the form of a pharmaceutical composition. As used herein, systemic administration includes oral and parenteral methods of administration. For oral administration, suitable pharmaceutical compositions of an inhibitor of MIF include powders, granules, pills, tablets, and capsules as well as liquids, syrups, suspensions, and emulsions. These compositions may also include flavorants, preservatives, suspending, thickening, and emulsifying agents, and other pharmaceutically acceptable additives. For parental administration, the compounds of preferred embodiments can be prepared in aqueous injection solutions that may contain, in addition to the inhibitor of MIF activity and/or export, buffers, antioxidants, bacteriostats, and other additives commonly employed in such solutions.

As mentioned above, administration of a compound of preferred embodiments can be employed to treat a wide variety of disorders or illnesses. In particular, the compounds of preferred embodiments may be administered to a warm-blooded animal for the treatment of inflammation, cancer, immune disorders, and the like.

MIF inhibiting compounds may be used in combination therapies with other pharmaceutical compounds. In preferred embodiments, the MIF inhibiting compound is present in combination with conventional drugs used to treat diseases or conditions wherein MIF is pathogenic or wherein MIF plays a pivotal or other role in the disease process. In particularly preferred embodiments, pharmaceutical compositions are provided comprising one or more MIF inhibiting compounds, including, but not limited to compounds of structures (I), (II), or (III), in combination with one or more additional pharmaceutical compounds, including, but not limited to drugs for the treatment of various cancers, asthma or other respiratory diseases, sepsis, arthritis, inflammatory bowel disease (IBD), or other inflammatory diseases, immune disorders, or other diseases or disorders wherein MIF is pathogenic.

The MIF inhibitors of preferred embodiments can be used for pharmaceutical treatment alone or in combination with one or more other pharmaceutically active agents, e.g., such as agents useful in treating inflammation, tumor growth, or associated diseases. Such other pharmaceutically active agents include, e.g., steroids, glucocorticoids, inhibitors of other inflammatory cytokines (e.g, anti-TNFα antibodies, anti-IL-1 antibodies, anti-IFN-γ antibodies), and other cytokines such as IL-1RA or IL-10, and other MIF inhibitors.

Combination therapies can include fixed combinations, in which two or more pharmaceutically active agents are in the same formulation; kits, in which two or more pharmaceutically active agents in separate formulations are sold in the same package, e.g, with instructions for co-administration; and free combinations in which the pharmaceutically active agents are packaged separately, but instruction for simultaneous or sequential administration are provided. Other kit components can include diagnostics, assays, multiple dosage forms for sequential or simultaneous administration, instructions and materials for reconstituting a lyophilized or concentrated form of the pharmaceutical composition, apparatus for administering the pharmaceutically active agents, and the like.

In particularly preferred embodiments, one or more MIF inhibiting compounds are present in combination with one or more nonsteroidal anti-inflammatory drugs (NSAIDs) or other pharmaceutical compounds for treating arthritis or other inflammatory diseases. Preferred compounds include, but are not limited to, celecoxib; rofecoxib; NSAIDS, for example, aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In particularly preferred embodiments, one or more MIF inhibiting compounds are present in combination with one or more beta stimulants, inhalation corticosteroids, antihistamines, hormones, or other pharmaceutical compounds for treating asthma, acute respiratory distress, or other respiratory diseases. Preferred compounds include, but are not limited to, beta stimulants, for example, commonly prescribed bronchodilators; inhalation corticosteroids, for example, beclomethasone, fluticasone, triamcinolone, mometasone, and forms of prednisone such as prednisone, prednisolone, and methylprednisolone; antihistamines, for example, azatadine, carbinoxamine/pseudoephedrine, cetirizine, cyproheptadine, dexchlorpheniramine, fexofenadine, loratadine, promethazine, tripelennamine, brompheniramine, cholopheniramine, clemastine, diphenhydramine; and hormones, for example, epinephrine.

In particularly preferred embodiments, one or more MIF inhibiting compounds are present in combination with pharmaceutical compounds for treating IBD, such as azathioprine or corticosteroids, in a pharmaceutical composition.

In particularly preferred embodiments, one or more MIF inhibiting compounds are present in combination with pharmaceutical compounds for treating cancer, such as paclitaxel, in a pharmaceutical composition.

In particularly preferred embodiments, one or more MIF inhibiting compounds are present in combination with immunosuppresive compounds in a pharmaceutical composition. In particularly preferred embodiments, one or more MIF inhibiting compounds are present in combination with one or more drugs for treating an autoimmune disorder, for example, Lyme disease, Lupus (e.g., Systemic Lupus Erythematosus (SLE)), or Acquired Immune Deficiency Syndrome (AIDS). Such drugs may include protease inhibitors, for example, indinavir, amprenavir, saquinavir, lopinavir, ritonavir, and nelfinavir; nucleoside reverse transcriptase inhibitors, for example, zidovudine, abacavir, lamivudine, idanosine, zalcitabine, and stavudine; nucleotide reverse transcriptase inhibitors, for example, tenofovir disoproxil fumarate; non nucleoside reverse transcriptase inhibitors, for example, delavirdine, efavirenz, and nevirapine; biological response modifiers, for example, etanercept, infliximab, and other compounds that inhibit or interfere with tumor necrosing factor; antivirals, for example, amivudine and zidovudine.

In particularly preferred embodiments, one or more MIF inhibiting compounds are present in combination with pharmaceutical compounds for treating sepsis, such as steroids or anti-infective agents. Examples of steroids include corticosteroids, for example, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone. Examples of anti-infective agents include anthelmintics (mebendazole), antibiotics including aninoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

In the treatment of certain diseases, it may be beneficial to treat the patient with a MIF inhibitor in combination with an anesthetic, for example, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

The compounds of preferred embodiments can generally be employed as the free acid or the free base. Alternatively, the compounds of preferred embodiments can preferably be in the form of acid or base addition salts. The term "pharmaceutically acceptable salt" of structures (I), (II), and (III) is intended to encompass any and all acceptable salt forms. While salt forms of the preferred embodiments are preferably pharmaceutically acceptable salts, in certain embodiments pharmaceutically unacceptable salts can be employed (e.g., for preparation, isolation, and/or purification purposes).

The compounds of structure (I), (II), and (III) can be made according to the organic synthesis techniques known to those skilled in this field, as well as by the representative methods set forth in the following examples.

Preparation of Compounds of Structure I)

A preferred intermediate in the preparation of compound of structure (I) is 7-chloro-5-oxo-4,5-dihydro-thieno[3,2-b]pyridine-6-carboxylic acid ethyl ester, depicted by formula (4) below. To prepare this intermediate, methyl-3-aminothiophene-2-carboxylate was reacted with ethylmalonyl chloride to yield intermediate 3-(2-ethoxycarbonyl-acetylamino)-thiophene-2-carboxylic acid methyl ester, depicted by formula (1). This intermediate was converted to 7-hydroxy-5-oxo-4,5-dihydro-thieno[3,2-b]pyridine-6-carboxylic acid ethyl ester, depicted by formula (2), by reacting with sodium ethoxide, and was then converted into 5,7-dihloro-thieno[3,2-b]pyridine-6-carboxylic acid ethyl ester, depicted by formula (3). Hydrolysis of 5,7-dihloro-thieno[3,2-b]pyridine-6-carboxylic acid ethyl ester, depicted by formula (3), yielded 7-chloro-5-oxo-4,5-dihydro-thieno[3,2-b]pyrdine-6-carboxylic acid ethyl ester, depicted by formula (4) as shown in Scheme 1.

Scheme 1

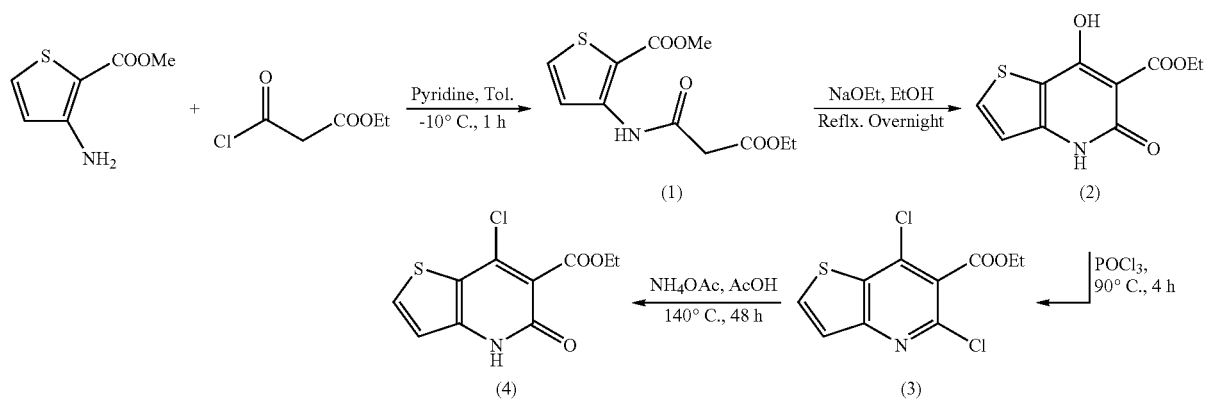

In one method, intermediate 7-chloro-5-oxo-4,5-dihydro-thieno[3,2-b]pyridine-6-carboxylic acid ethyl ester, depicted by formula (4), was reacted with piperazin-1-yl-thiophene-2-yl-methanone to yield 5-oxo-7-[4-(thiophene-2-carbonyl)-piperazin-1-yl]-4,5-dihydro-thieno[2,3-b]-pyridine-6-carboxylic acid ethyl ester, depicted by formula (5). This intermediate was either reacted with an appropriate halide ($R_1$—X) or boronic acid ($R_1$—$B(OH)_2$) to yield the target compounds of structure (I) with $R_2$ as ethyl carboxylate, $R_3$ as thiophene and $R_1$ as defined above, as shown in Scheme 2.

Scheme 2

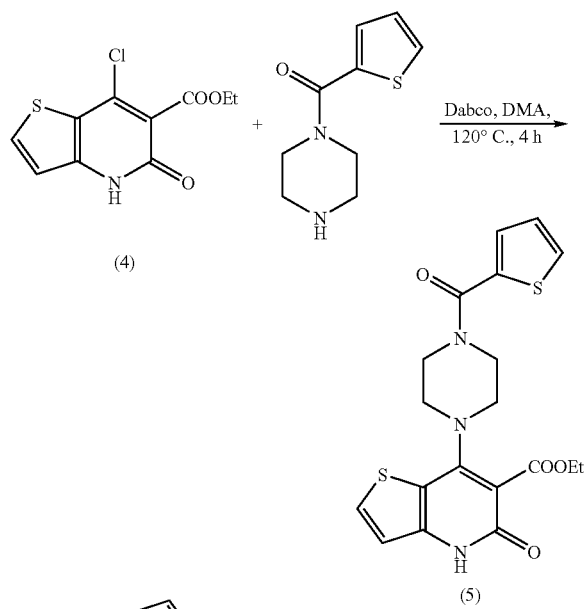

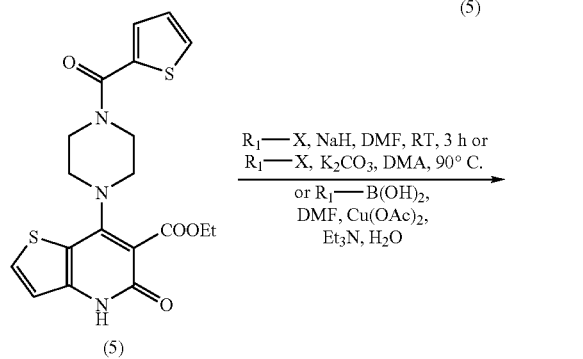

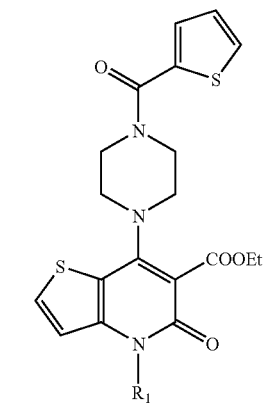

To yield compounds of structure (I) wherein $R_2$ is ethyl carboxylate, $R_3$ is furan and $R_1$ is as defined above, intermediate 7-chloro-5-oxo-4,5-dihydro-thieno[3,2-b]pyridine-6-carboxylic acid ethyl ester, depicted by formula (4), was reacted with 1-(2-furyl)-piperazine to yield 5-oxo-7-[4-(furan-2-carbonyl)-piperazin-1-yl]-4,5-dihydro-thieno[2,3-b]-pyrdine-6-carboxylic acid ethyl ester, depicted by formula (6). This intermediate was either reacted with an appropriate halide ($R_1$—X) or with boronic acid ($R_1$—$B(OH)_2$) to yield the target compounds of structure (I), with $R_3$ as furan and $R_1$ as defined above, as shown in Scheme 3.

Scheme 3

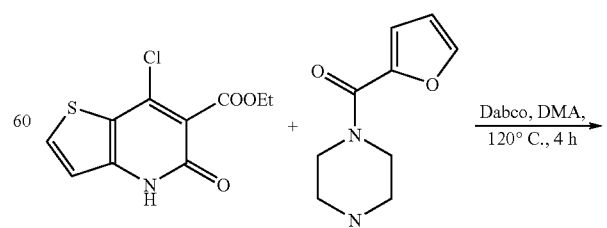

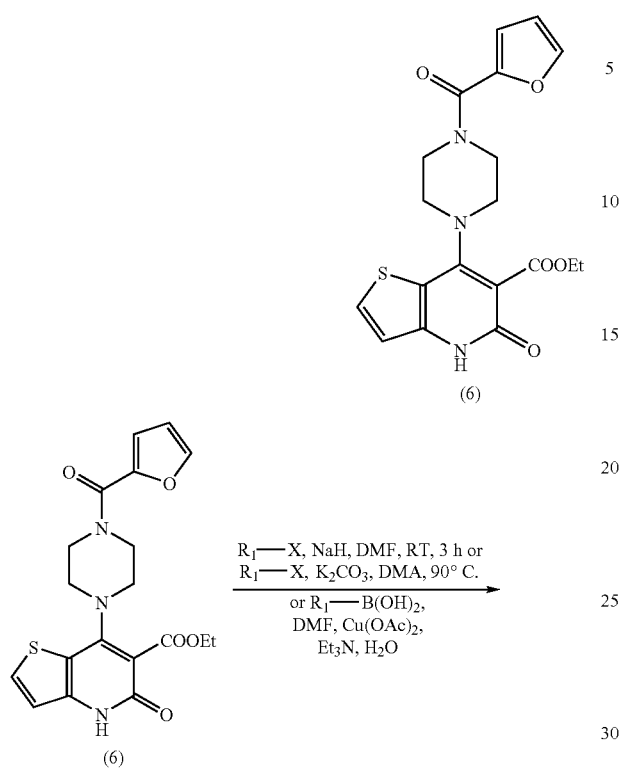

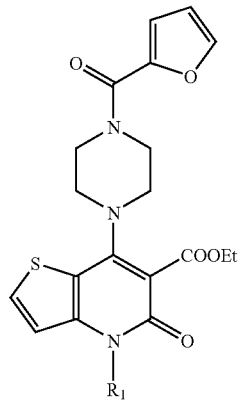

In another method, intermediate 7-chloro-5-oxo-4,5-dihydro-thieno[3,2-b]pyrdine-6-carboxylic acid ethyl ester, depicted by formula (4), was reacted with tert-butyl-1-piperazine carboxylate to yield 7-(4-tert-butoxycarbonyl-piperazin-1-yl)-5-oxo-4,5-dihydro-thieno[2,3-b]-pyrdine-6-carboxylic acid ethyl ester, depicted by formula (7). This intermediate was either reacted with an appropriate halide ($R_1$—X) or boronic acid ($R_1$—B(OH)$_2$) to yield the intermediate of structure (8), which was deprotected and reacted with an appropriate acid chloride ($R_3$—COCl) or acid ($R_3$—COOH) to yield target compounds of structure (I) with $R_2$ as ethyl carboxylate, and $R_1$ and $R_3$ as defined above, as shown in Scheme 4.

Scheme 4

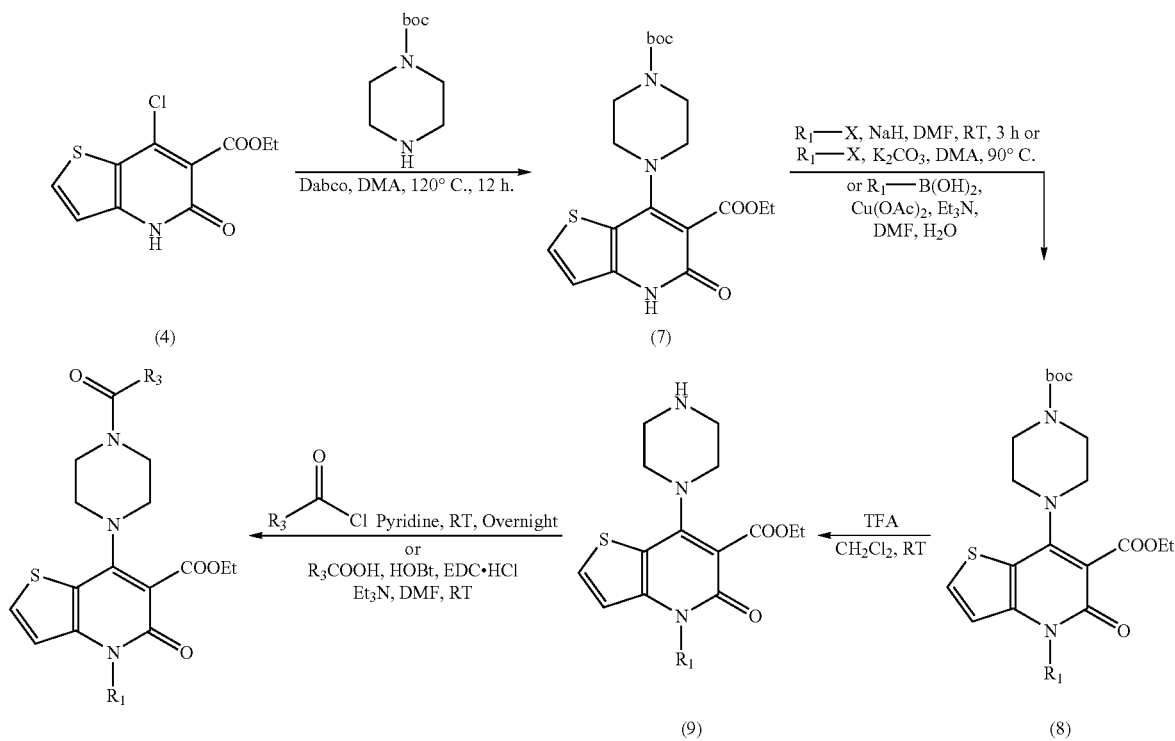

To prepare compounds of structure (I) with $R_2$ as carbonitrile, and $R_1$ and $R_3$ as defined above, 7-chloro-5-oxo-4,5-dihydro-thieno[3,2-b]pyridine-6-carbonitrile, depicted by formula (12), was used as a key intermediate. To prepare this intermediate, methyl-3-amino-thiophene-2-carboxylate was reacted with methylcyanoacetate to yield intermediate 3-(2-cyano-acetylamino)-thiophene-2-carboxylic acid methyl ester, depicted by formula (10). This intermediate was converted to 7-hydroxy-5-oxo-4,5-dihydro-thieno[3,2-b]pyridine-6-carbonitrile, depicted by formula (11), by reacting with sodium ethoxide, and was then converted into 7-chloro-5-oxo-4,5-dihydro-thieno[3,2-b]pyridine-6-carbonitrile, depicted by formula (12), as shown in Scheme 5.

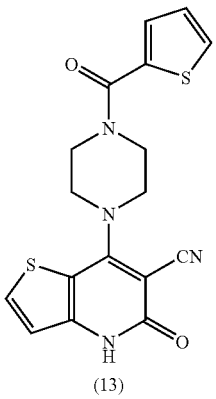

Scheme 5

To yield a compound of structure (I) with $R_2$ as carbonitrile, $R_3$ as thiophene and $R_1$ as defined above, the intermediate 7-chloro-5-oxo-4,5-dihydro-thieno[3,2-b]pyridine-6-carbonitrile depicted by formula (12) was reacted with piperazin-1-yl-thiophene-2-yl-methanone to yield 5-oxo-7-[4-(thiophene-2-carbonyl)-piperazin-1-yl]-4,5-dihydro-thieno[2,3-b]-pyridine-6-carbonitrile, depicted by formula (13), which was either reacted with an appropriate halide ($R_1$—X) or boronic acid ($R_1$—B(OH)$_2$) to yield the target compounds of structure (I) with $R_2$ as carbonitrile, $R_3$ as thiophene, and $R_1$ as defined above as shown in Scheme 6.

Scheme 6

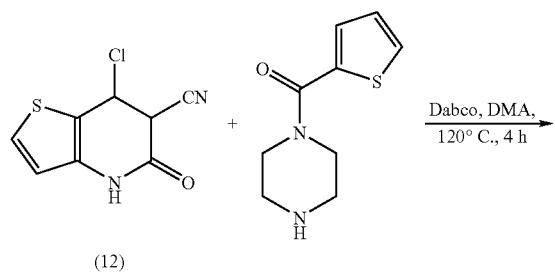

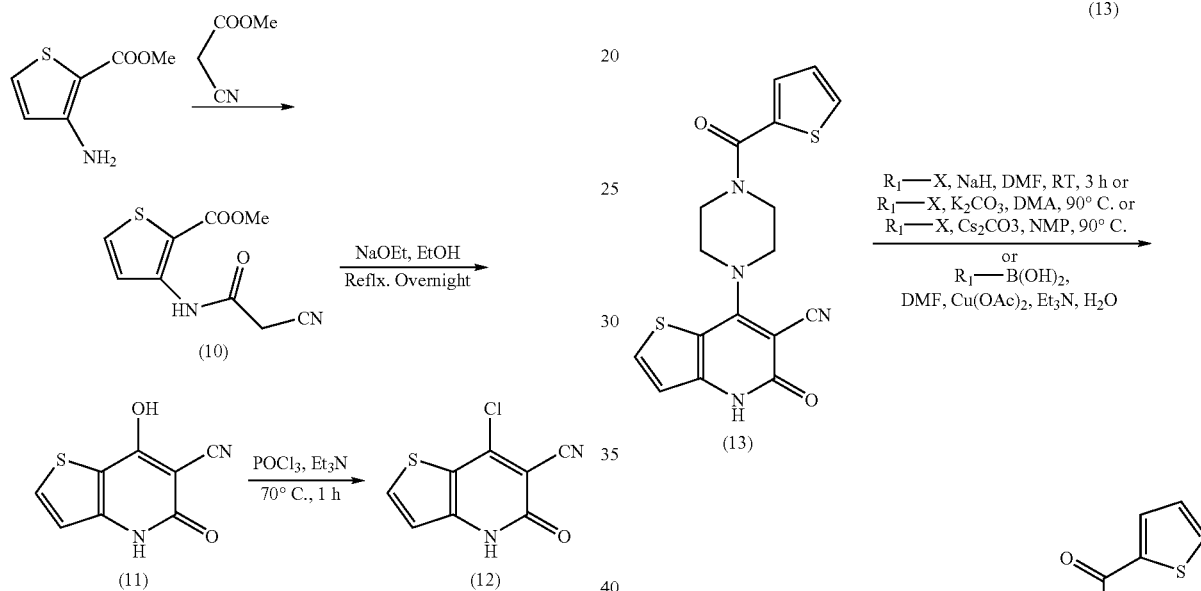

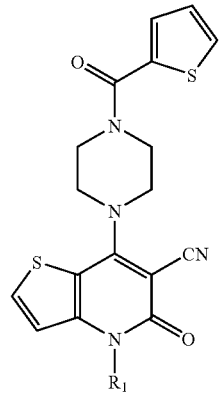

To yield compounds of structure (I), wherein $R_2$ is carbonitrile, $R_3$ is furan, and $R_1$ is as defined above, intermediate 7-chloro-5-oxo-4,5-dihydro-thieno[3,2-b]pyridine-6-carboxylic acid ethyl ester, depicted by formula (12), was reacted with 1-(2-furyl)-piperazine to yield 5-oxo-7-[4-(furan-2-carbonyl)-piperazin-1-yl]-4,5-dihydro-thieno[2,3-b]-pyrdine-6-carbonitrile, depicted by formula (14). This intermediate was either reacted with an appropriate halide ($R_1$—X) or boronic acid ($R_1$—B(OH)$_2$) to yield target compounds of structure (I) with $R_2$ as carbonitrile, $R_3$ as furan, and $R_1$ as defined above, as shown in Scheme 7.

Scheme 7

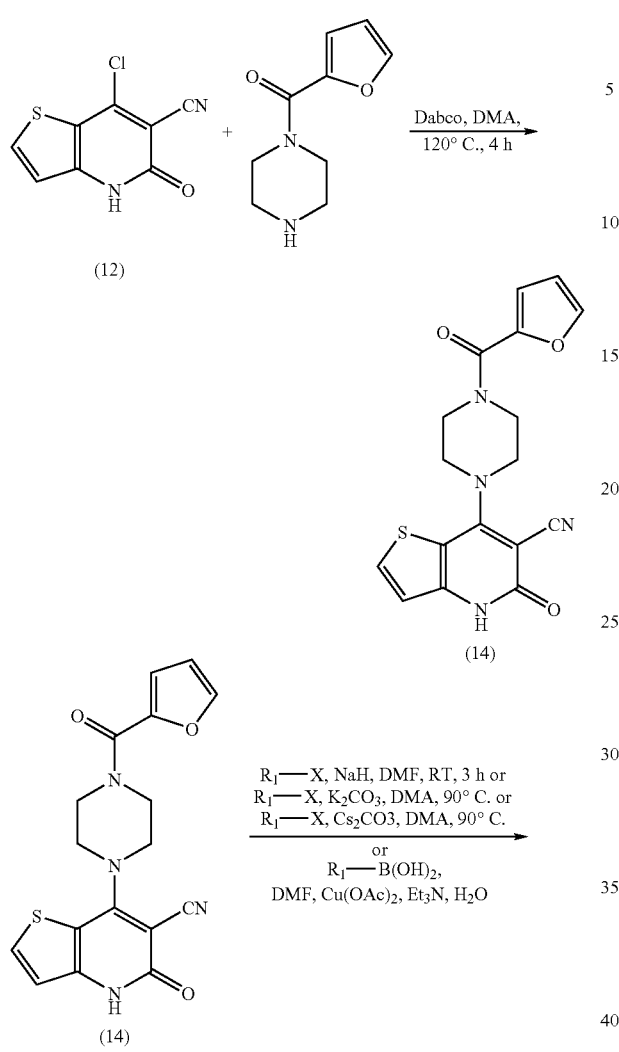

Compounds of structure (I) with $R_2$ as carbonitrile, and $R_1$ and $R_3$ as defined above were also prepared from intermediate 7-chloro-5-oxo-4,5-dihydro-thieno[3,2-b]pyridine-6-carbonitrile, depicted by formula (12). Intermediate 7-chloro-5-oxo-4,5-dihydro-thieno[3,2-b]pyridine-6-carbonitrile, depicted by formula (12), was reacted with tert-butyl-1-piperazine carboxylate to yield 7-(4-tert-butoxycarbonyl-piperazin-1-yl)-5-oxo-4,5-dihydro-thieno[2,3-b]-pyridine-6-carbonitrile, depicted by formula (15). This intermediate was either reacted with an appropriate halide ($R_1$—X) or boronic acid ($R_1$—B(OH)$_2$) to yield an intermediate of structure (16), which was deprotected and reacted with an appropriate acid chloride ($R_3$—COCl), or an acid ($R_3$—COOH) to yield target compounds of structure (I) with $R_2$ as carbonitrile, and $R_1$ and $R_3$ as defined above, as shown in Scheme 8.

Scheme 8

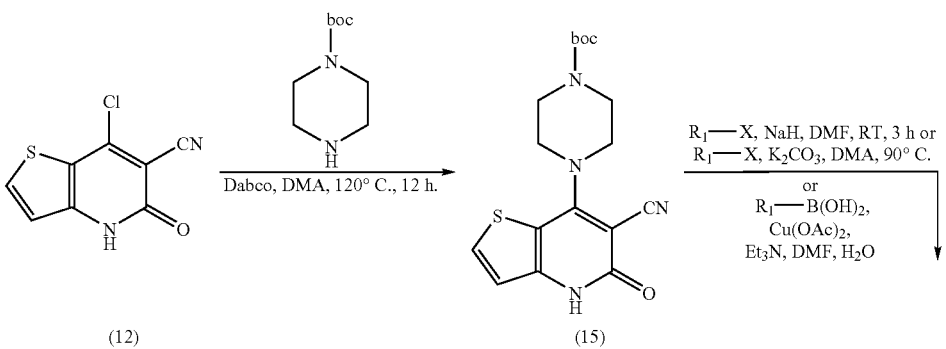

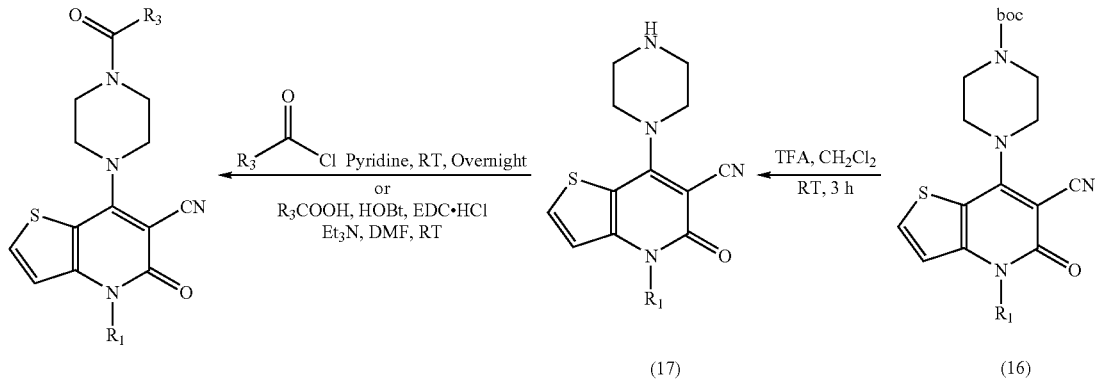

To yield compounds of structure (I) with $R_1$ as alkyl benzoic acid, and $R_2$ and $R_3$ as defined above, the corresponding methyl or ethyl esters were prepared as shown in Scheme 4 and Scheme 8 above and hydrolyzed to the corresponding acids by $BBr_3$, as shown in Scheme 9.

Scheme 9

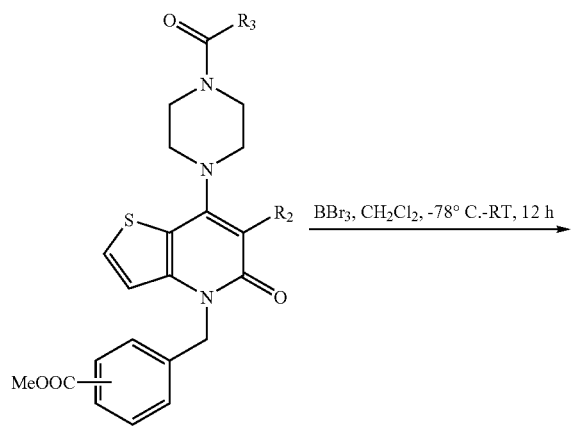

-continued

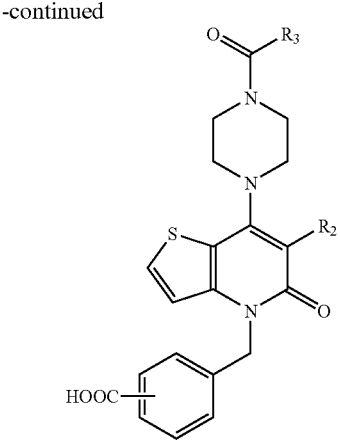

Preparation of Compounds of Structure (II)

Compounds of structure (II) were prepared by using 4-amino-thiophene-3-carboxylic acid methyl ester, as depicted by formula (21), as a starting material. To make this compound, methyl thioglycolate was reacted with methyl acrylate to yield intermediate 3-methoxycarbonylmethylsulfanyl-propionic acid methyl ester, depicted by formula (18), which was cyclized to 4-oxo-tetrahydro-thiophene-3-carboxylic acid methyl ester, depicted by formula (19). This intermediate was reacted with hydroxylamine hydrochloride to yield 4-hydroxyimino-tetrahydro-thiophene-3-carboxylic acid methyl ester, depicted by formula (20), which yielded 4-amino-thiophene-3-carboxylic acid methyl ester hydrochloride, depicted by formula (21), as shown in Scheme 10.

Scheme 10

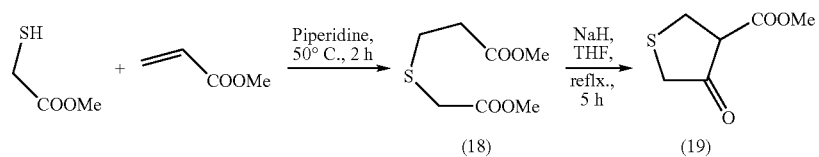

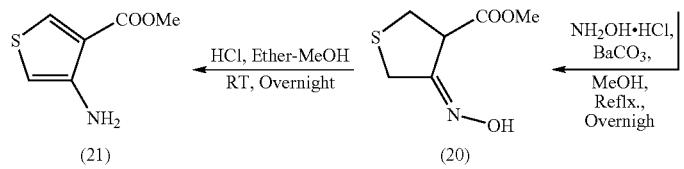

A preferred intermediate in the preparation of a compound of formula (II) is 4-chloro-1,2-dihydro-2-oxo-thieno[3,4-b]pyridine-3-carboxylic acid ethyl ester, depicted by formula (25) below. To prepare this intermediate, 4-aminothiophene-3-carboxylic acid methyl ester hydrochloride, depicted by formula (21), was reacted with ethylmalonyl chloride to yield intermediate 4-(2-ethoxycarbonyl-acetylamino)-thiophene-3-carboxylic acid methyl ester, depicted by formula (22). This intermediate was converted to 7-hydroxy-5-oxo-4,5-dihydro-2-thia-4-aza-indene-6-carboxylic acid ethyl ester, depicted by formula (23) by reacting with sodium ethoxide, and was then converted into 5,7-dihloro-2-thia-4-aza-indene-6-carboxylic acid ethyl ester, depicted by formula (24). Hydrolysis 5,7-dihloro-2-thia-4-aza-indene-6-carboxylic acid ethyl ester, depicted by formula (24), yielded 7-chloro-5-oxo-4,5-dihydro-2-thia-4-aza-indene-3-carboxylic acid ethyl ester, depicted by formula (25), as shown in Scheme 11.

In one method, 7-chloro-5-oxo-4,5-dihydro-2-thia-4-aza-indene-3-carboxylic acid ethyl ester, depicted by formula (25), was reacted with piperazin-1-yl-thiophene-2-yl-methanone to yield 5-oxo-7-[4-(thiophene-2-carbonyl)-piperazin-1-yl]-4,5-dihydro-2-thia-4-aza-indene-6-carboxylic acid ethyl ester, depicted by formula (26). This intermediate was either reacted with an appropriate halide ($R_1$—X) or boronic acid ($R_1$—B(OH)$_2$) to yield target compounds of structure (II) with $R_2$ as ethyl carboxylate, $R_3$ as thiophene, and $R_1$ as defined above, as shown in Scheme 12.

Scheme 12

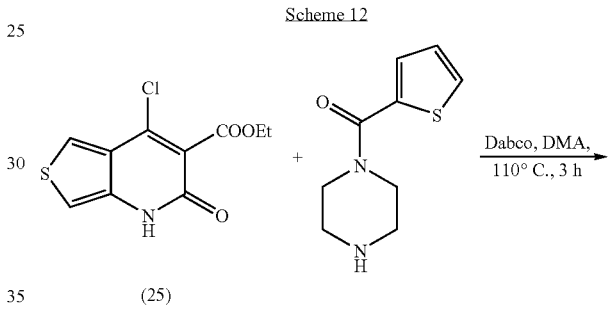

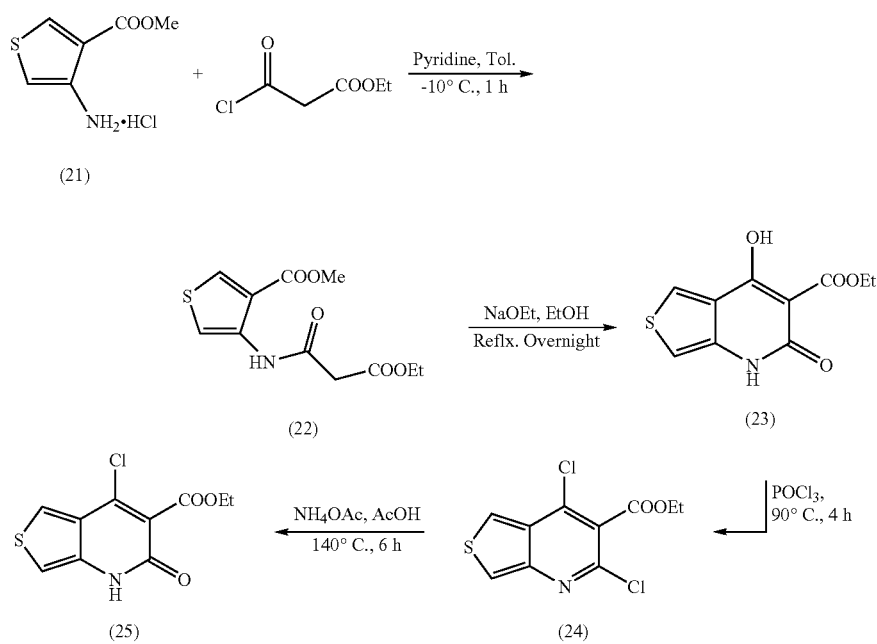

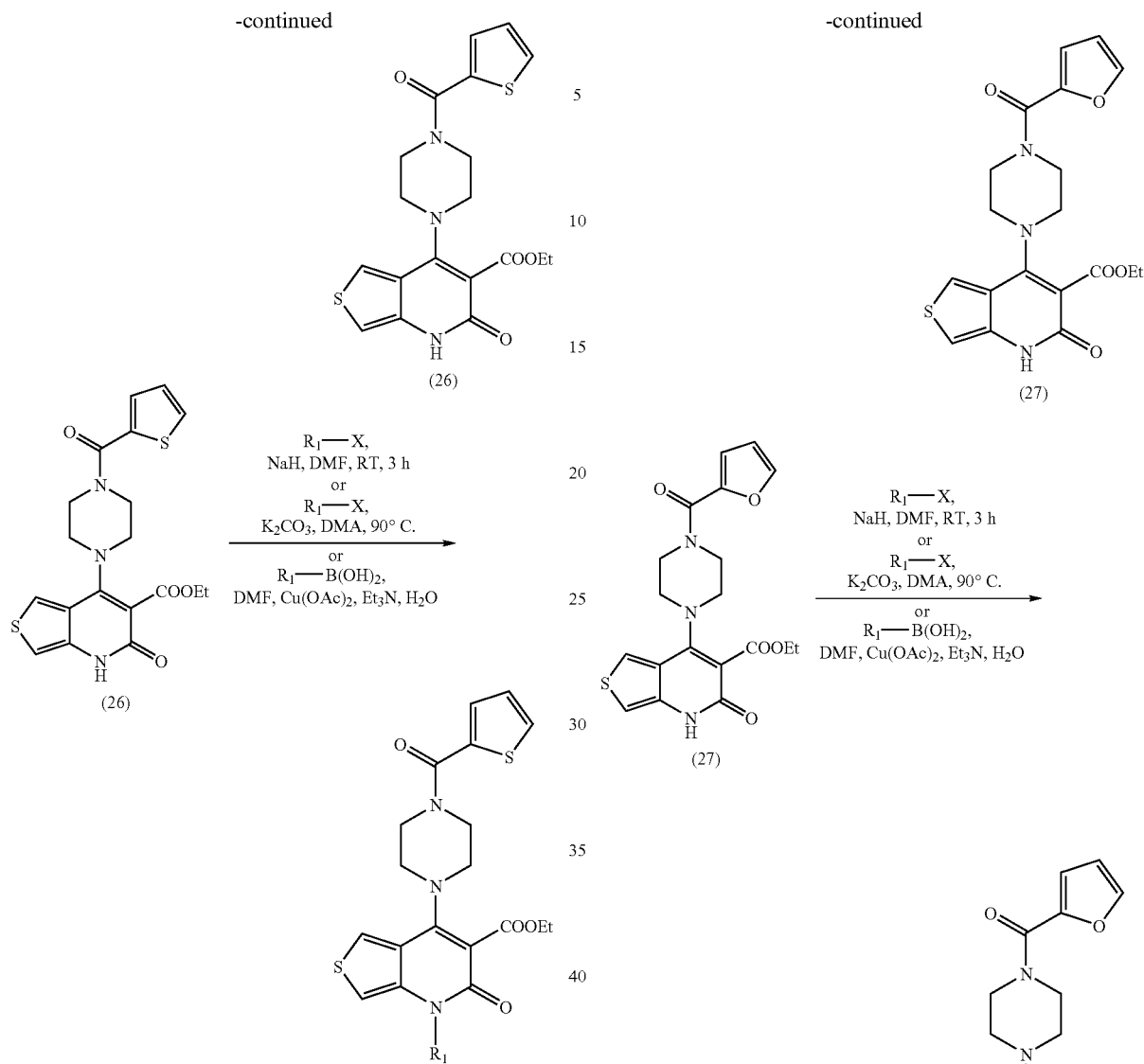

To yield compounds of structure (II) where $R_2$ is ethyl carboxylate, $R_3$ is furan, and $R_1$ is as defined above, intermediate 7-chloro-5-oxo-4,5-dihydro-2-thia-4-aza-indene-3-carboxylic acid ethyl ester, depicted by formula (25), was reacted with 1-(2-furyl)-piperazine to yield 5-oxo-7-[4-(furan-2-carbonyl)-piperazin-1-yl]-4,5-dihydro-2-thia-4-aza-indene-6-carboxylic acid ethyl ester, depicted by formula (27), which was either reacted with an appropriate halide ($R_1$—X) or boronic acid ($R_1$—B(OH)$_2$) to yield compounds of structure (I) with $R_3$ as furan and $R_1$ as defined above, as shown in Scheme 13.

Scheme 13

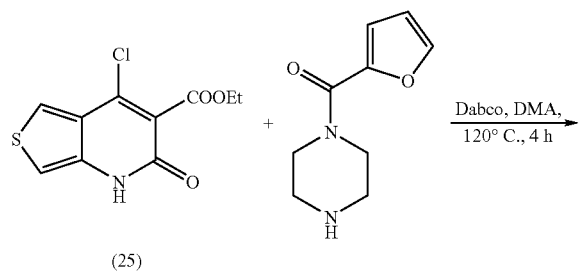

In another method, intermediate 7-chloro-5-oxo-4,5-dihydro-2-thia-4-aza-indene-3-carboxylic acid ethyl ester, depicted by formula (25), was reacted with tert-butyl-1-piperazine carboxylate to yield 7-(4-tert-butoxycarbonyl-piperazin-1-yl)-5-oxo-4,5-dihydro-2-thia-4-aza-indene-6-carboxylic acid ethyl ester, depicted by formula (28). This intermediate was either reacted with an appropriate halide ($R_1$—X) or boronic acid ($R_1$—B(OH)$_2$) to yield an intermediate of structure (29), which was deprotected and reacted with an appropriate acid chloride ($R_3$—COCl) or acid ($R_3$—COOH) to yield target compounds of structure (II), with $R_2$ as ethyl carboxylate, and $R_1$ and $R_3$ as defined above, as shown in Scheme 14.

Scheme 14

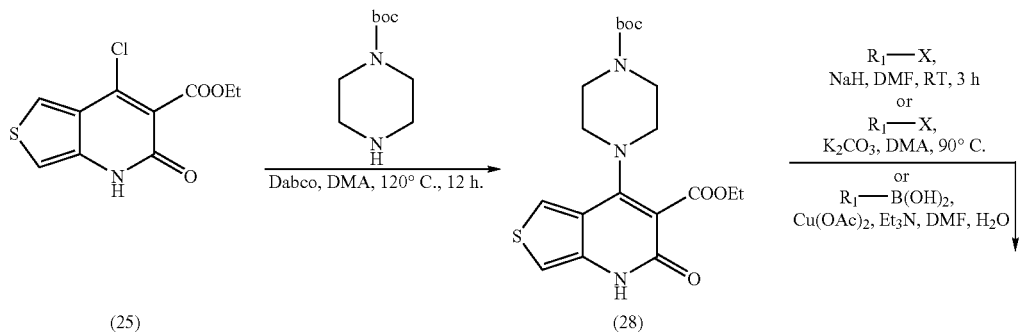

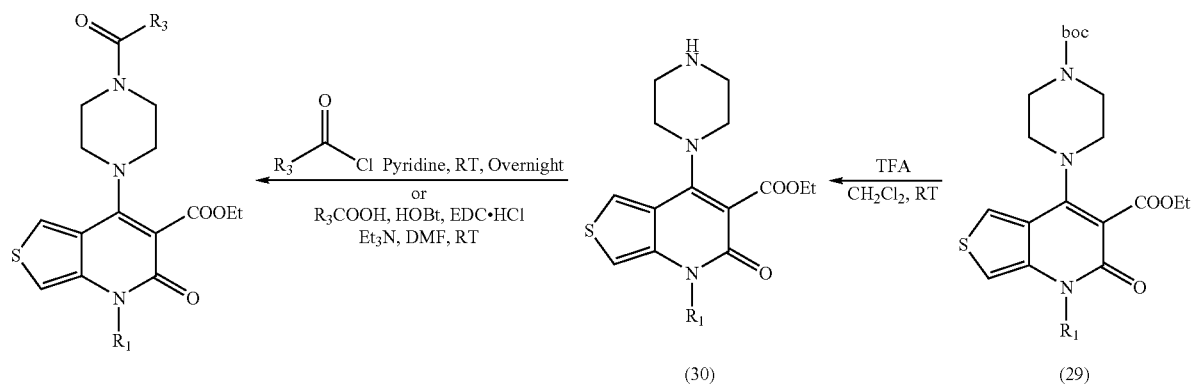

To prepare compounds of structure (II) with R₂ as carbonitrile, and R₁ and R₃ as defined above, 7-chloro-5-oxo-4,5-dihydro-2-thia-4-aza-indene-6-carbonitrile, depicted by formula (33), was used as a key intermediate. To prepare this intermediate, 7-hydroxy-5-oxo-4,5-dihydro-2-thia-4-aza-indene-6-carboxylic acid ethyl ester, depicted by formula (23), was reacted with cyclohexylamine to yield intermediate 7-hydroxy-5-oxo-4,5-dihydro-2-thia-4-aza-indene-6-carboxylic acid cyclohexylamide, depicted by formula (31). This intermediate was converted to 5,7-dichloro-2-thia-4-aza-indene-6-carbonitrile, depicted by formula (32), by reacting with phosphorous oxychloride, and was then converted into 7-chloro-5-oxo-4,5-dihydro-2-thia-4-aza-6-carbonitrile, depicted by formula (33), as shown in Scheme 15.

Scheme 15

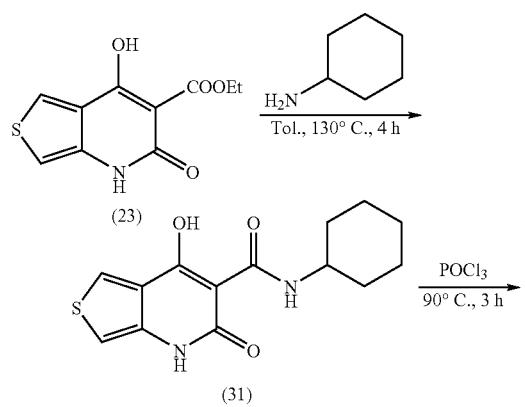

-continued

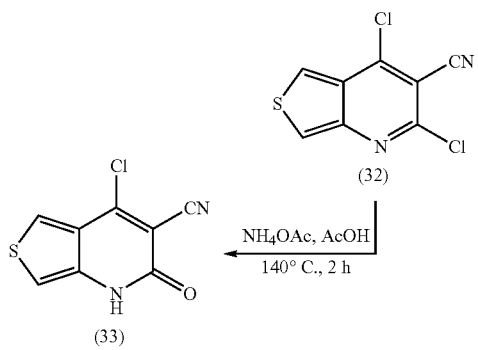

To yield a compound of structure (II) with R₂ as carbonitrile, R₃ as thiophene, and R₁ as defined above, the intermediate 7-chloro-5-oxo-4,5-dihydro-2-thia-4-aza-indene-6-carbonitrile, depicted by formula (33), was reacted with piperazin-1-yl-thiophene-2-yl-methanone to yield 5-oxo-7-[4-(thiophene-2-carbonyl)-piperazin-1-yl]-4,5-dihydro-2-thia-4-aza-indene-6-carbonitrile, depicted by formula (34), which was either reacted with an appropriate halide (R₁—X) or boronic acid (R₁—B(OH)₂) to yield target compounds of structure (II) with R₂ as carbonitrile, R₃ as thiophene, and R₁ as defined above, as shown in Scheme 16.

Scheme 16

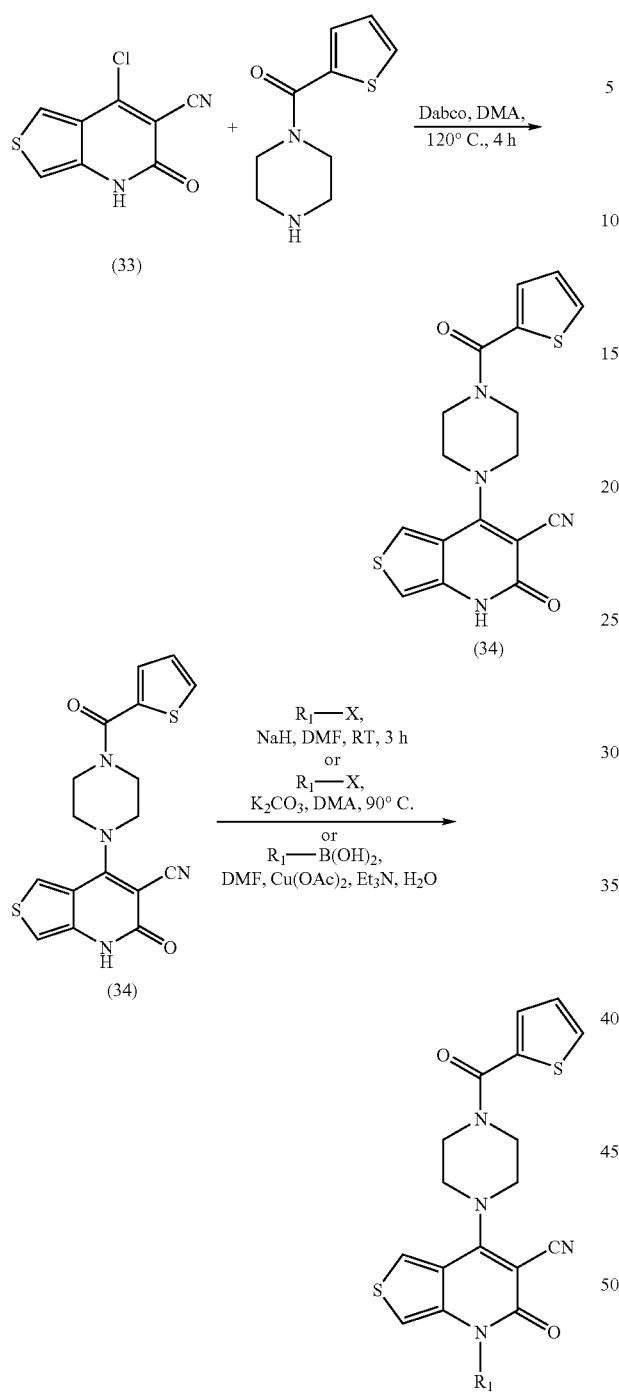

Scheme 17

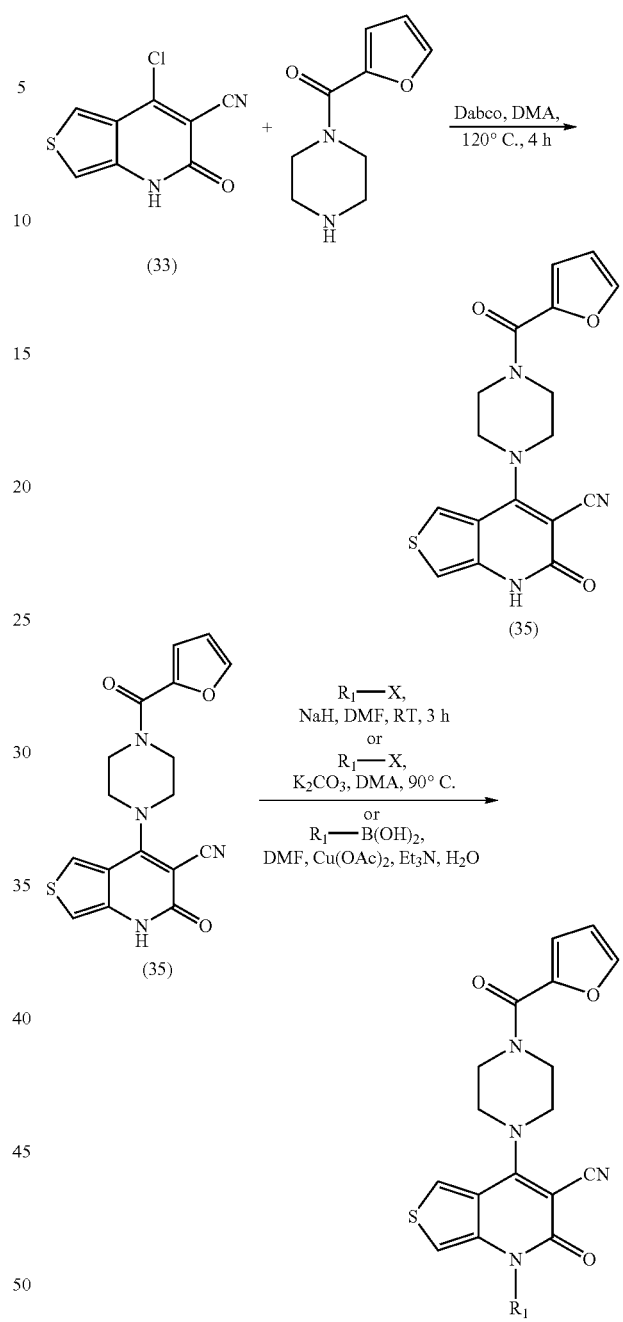

To yield compounds of structure (II) wherein $R_2$ is carbonitrile, $R_3$ is furan, and $R_1$ is as defined above, intermediate 7-chloro-5-oxo-4,5-dihydro-2-thia-4-aza-indene-6-carbonitrile, depicted by formula (33), was reacted with 1-(2-furyl)-piperazine to yield 5-oxo-7-[4-(furan-2-carbonyl)-piperazin-1-yl]-4,5-dihydro-2-thia-4-aza-indene-6-carbonitrile, depicted by formula (35). This intermediate was either reacted with an appropriate halide ($R_1$—X) or boronic acid ($R_1$—B(OH)$_2$) to yield the target compounds of structure (II) with $R_2$ as carbonitrile, $R_3$ as furan, and $R_1$ as defined above, as shown in Scheme 17.

Compounds of structure (II) with $R_2$ as carbonitrile, and $R_1$ and $R_3$ as defined above were also prepared from intermediate 7-chloro-5-oxo-4,5-dihydro-2-thia-4-aza-indene-6-carbonitrile, depicted by formula (33). Intermediate 7-chloro-5-oxo-4,5-dihydro-2-thia-4-aza-indene-6-carbonitrile, depicted by formula (33), was reacted with tert-butyl-1-piperazine carboxylate to yield 7-(4-tert-butoxycarbonyl-piperazin-1-yl)-5-oxo-4,5-dihydro-2-thia-4-aza-indene-6-carbonitrile, depicted by formula (36). This intermediate was either reacted with an appropriate halide ($R_1$—X) or boronic acid ($R_1$—B(OH)$_2$) to yield intermediate of structure (37), which was deprotected and reacted with an appropriate acid chloride ($R_3$—COCl) or acid ($R_3$—COOH) to yield target compounds of structure (II) with $R_2$ as carbonitrile, and $R_1$ and $R_3$ as defined above, as shown in Scheme 18.

Scheme 18

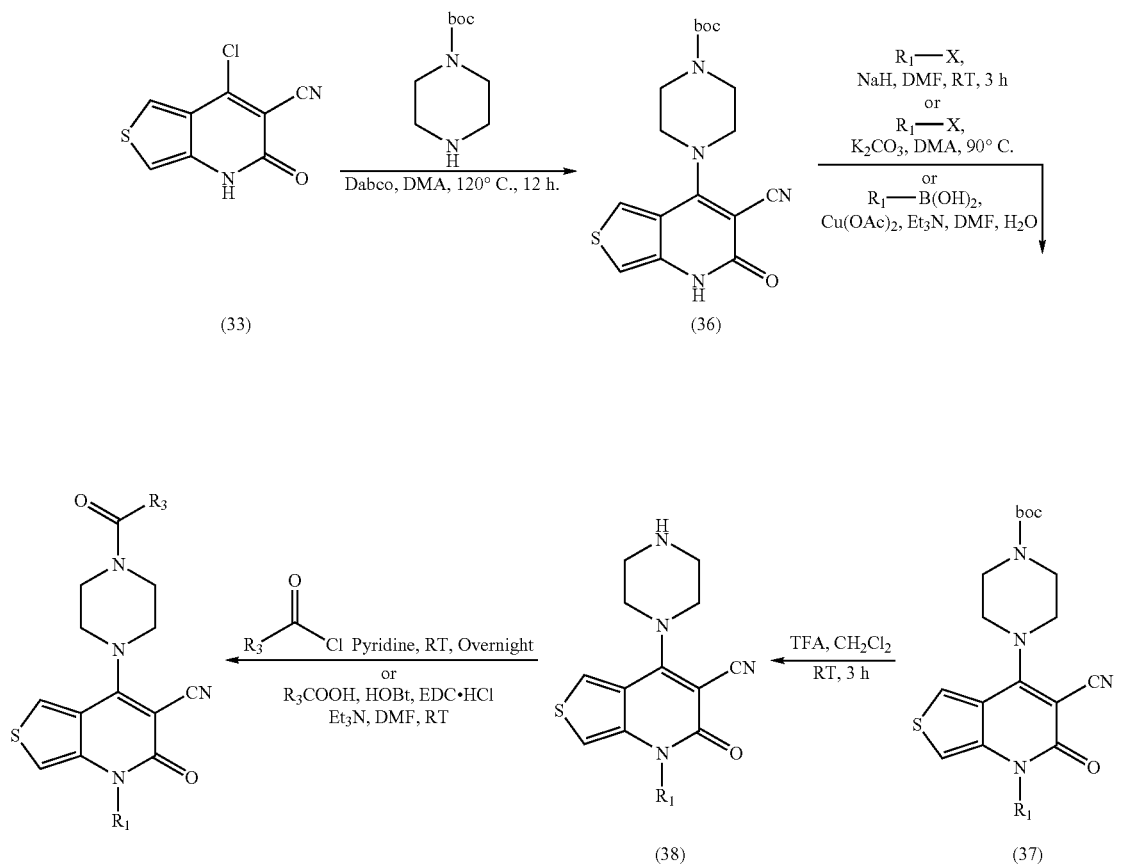

To yield compounds of structure (II) with $R_1$ as alkyl benzoic acid, and $R_2$ and $R_3$ as defined above, the corresponding methyl or ethyl esters were prepared as shown in Scheme 14 or Scheme 18 above, and hydrolyzed to corresponding acids by $BBr_3$, as shown in Scheme 19.

Scheme 19

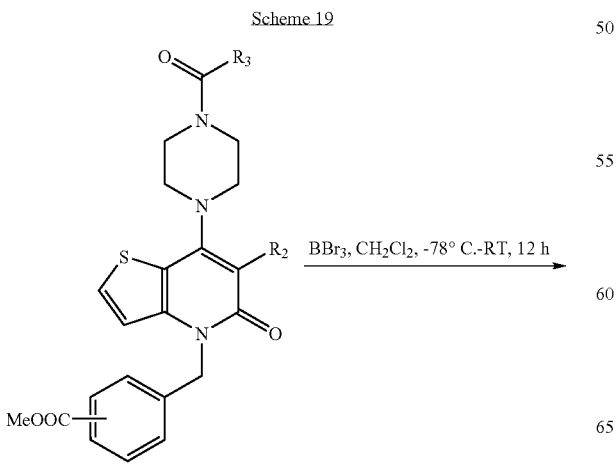

-continued

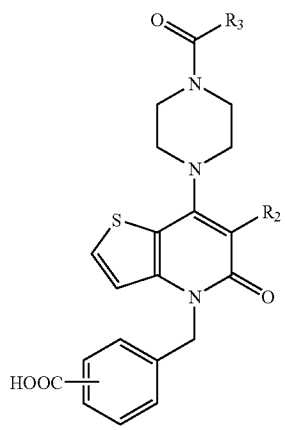

Preparation of Compounds of Structure (III)

A preferred intermediate in the preparation of compounds of structure (III) is 4-chloro-6-oxo-6,7-dihydro-thieno[2,3- b]pyridine-5-carboxylic acid ethyl ester, depicted by formula (42) below. To prepare this intermediate, methyl-2-amino-thiophene-3-carboxylate was reacted with ethylmalonyl chloride to yield intermediate 2-(2-ethoxycarbonyl-acetylamino)-thiophene-3-carboxylic acid methyl ester, depicted by formula (39). This intermediate was converted to 4-hydroxy-6-oxo-6,7-dihydro-thieno[2,3-b]pyridine-5-carboxylic acid ethyl ester, depicted by formula (40), by reacting it with sodium ethoxide, and then converting it into 4,6-dichloro-thieno[2,3-b]pyrdine-5-carboxylic acid ethyl ester, depicted by formula (41). Hydrolysis of 4,6-dichloro-thieno[2,3-b]pyrdine-5-carboxylic acid ethyl ester, depicted by formula (41), yielded 4-chloro-6-oxo-6,7-dihydro-thieno[2,3-b]pyridine-5-carboxylic acid ethyl ester, depicted by formula (42), as shown in Scheme 20.

-continued

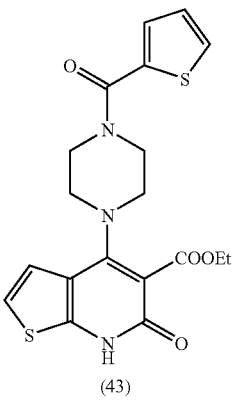

(43)

Scheme 20

In one method, intermediate 4-chloro-6-oxo-6,7-dihydro-thieno[2,3-b]pyridine-5-carboxylic acid ethyl ester, depicted by formula (42), was reacted with piperazin-1-yl-thiophene-2-yl-methanone to yield 6-oxo-4-[4-(thiophene-2-carbonyl)-piperazin-1-yl]-6,7-dihydro-thieno[3,2-b]pyridine-5-carboxylic acid ethyl ester, depicted by formula (43). This intermediate was either reacted with an appropriate halide ($R_1$—X) or boronic acid ($R_1$—B(OH)$_2$) to yield the target compounds of structure (III) with $R_2$ as ethyl carboxylate, $R_3$ as thiophene, and $R_1$ as defined above, as shown in scheme 21.

Scheme 21

-continued

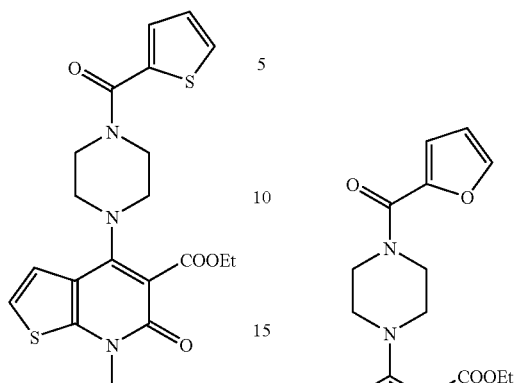

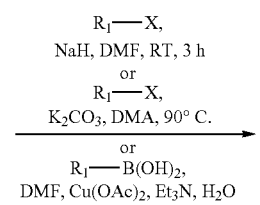

To yield compounds of structure (III) wherein $R_2$ is ethyl carboxylate, $R_3$ is furan, and $R_1$ is as defined above, intermediate 4-chloro-6-oxo-6,7-dihydro-thieno[2,3-b]pyrdine-5-carboxylic acid ethyl ester, depicted by formula (42), was reacted with 1-(2-furyl)-piperazine to yield 4-[4-(furan-2-carbonyl)-piperazin-1-yl]-6-oxo-6,7-dihydro-thieno[3,2-b]-pyrdine-5-carboxylic acid ethyl ester, depicted by formula (44). This intermediate was either reacted with an appropriate halide ($R_1$—X) or boronic acid ($R_1$—B(OH)$_2$) to yield the target compounds of structure (III) with $R_2$ as carboxylic acid, $R_3$ as furan and $R_1$ as defined above, as shown in scheme 23.

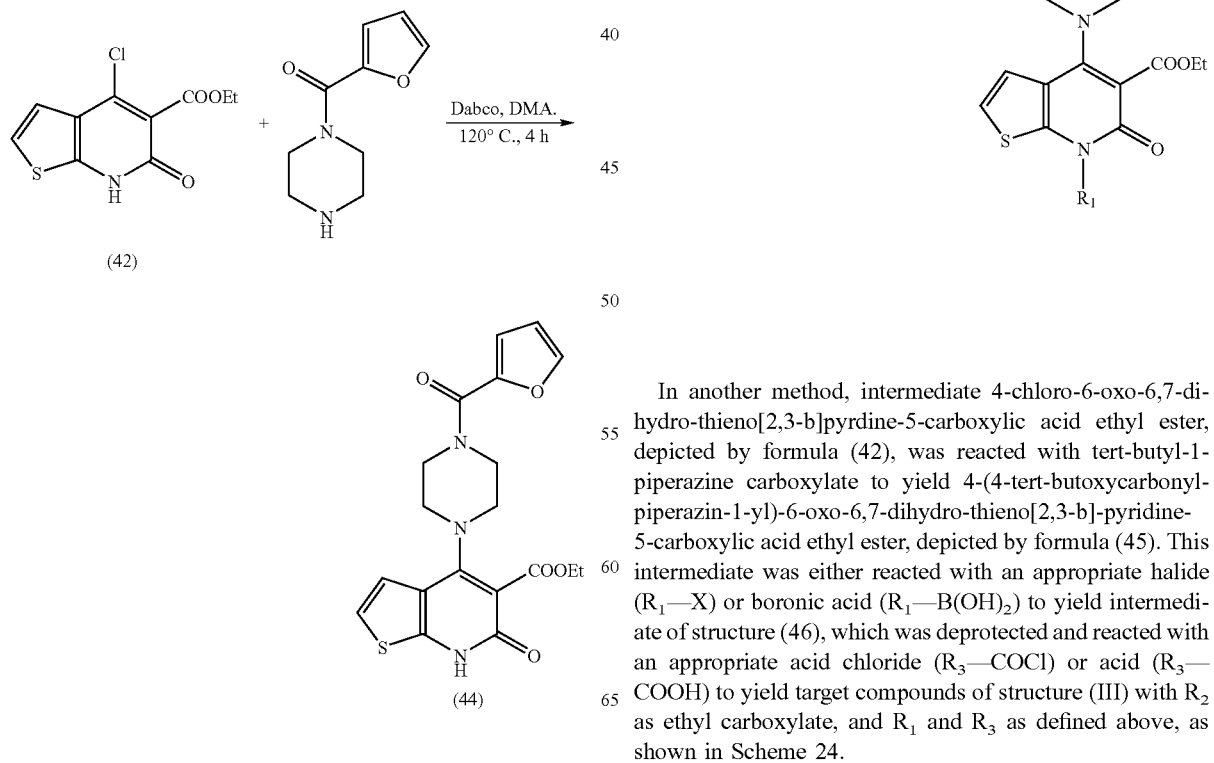

In another method, intermediate 4-chloro-6-oxo-6,7-dihydro-thieno[2,3-b]pyrdine-5-carboxylic acid ethyl ester, depicted by formula (42), was reacted with tert-butyl-1-piperazine carboxylate to yield 4-(4-tert-butoxycarbonyl-piperazin-1-yl)-6-oxo-6,7-dihydro-thieno[2,3-b]-pyridine-5-carboxylic acid ethyl ester, depicted by formula (45). This intermediate was either reacted with an appropriate halide ($R_1$—X) or boronic acid ($R_1$—B(OH)$_2$) to yield intermediate of structure (46), which was deprotected and reacted with an appropriate acid chloride ($R_3$—COCl) or acid ($R_3$—COOH) to yield target compounds of structure (III) with $R_2$ as ethyl carboxylate, and $R_1$ and $R_3$ as defined above, as shown in Scheme 24.

Scheme 24

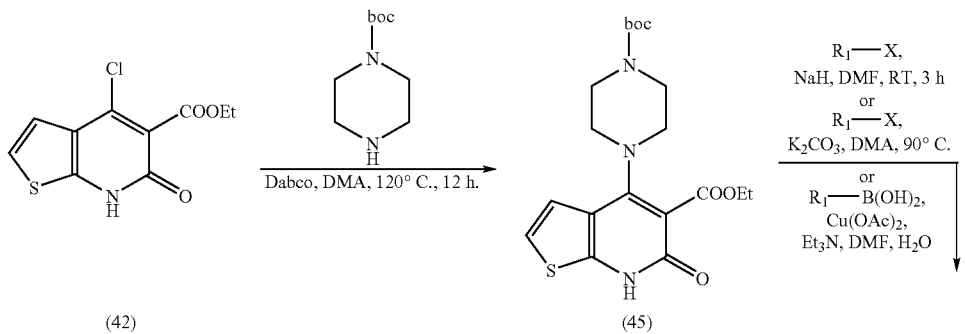

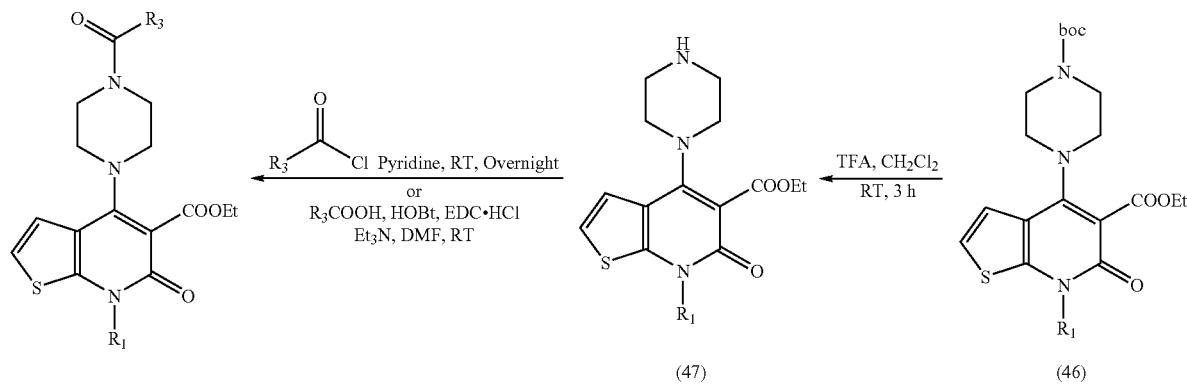

To yield compounds of structure (III) with $R_2$ as carbonitrile, and $R_1$ and $R_3$ as defined above, 4-chloro-6-oxo-6,7-dihydro-thieno[2,3-b]pyridine-5-carbonitrile, depicted by formula (50), was used as a key intermediate. To prepare this intermediate, 4-hydroxy-6-oxo-6,7-dihydro-thieno[2,3-b]pyridine-5-carboxylic acid ethyl ester, depicted by formula (40), was reacted with cyclohexylamine to yield intermediate 4-hydroxy-6-oxo-6,7-dihydro-thieno[2,3-b]pyridine-5-carboxylic acid cyclohexylamide, depicted by formula (48). This intermediate was converted to 4,6-dichloro-thieno[2,3-b]pyrdine-5-carbonitrile, depicted by formula (49), by reacting with phosphorous oxychloride, which was then converted into 4-chloro-6-oxo-6,7-dihydro-2-thieno[2,3-b]pyridine-5-carbonitrile, depicted by formula (50), as shown in Scheme 25.

Scheme 25

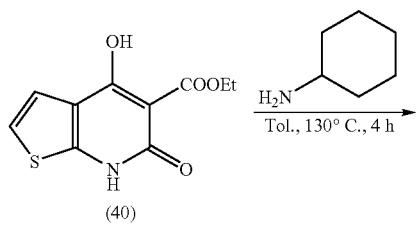

To yield a compound of structure (III) with $R_2$ as carbonitrile, $R_3$ as thiophene, and $R_1$ as defined above, the intermediate 4-chloro-6-oxo-6,7-dihydro-thieno[2,3-b]pyridine-5-carbonitrile, depicted by formula (50), was reacted with piperazin-1-yl-thiophene-2-yl-methanone to yield 6-oxo-4-[4-(thiophene-2-carbonyl)-piperazin-1-yl]-6,7-dihydro-thieno[2,3-b]pyridine-5-carbonitrile, depicted by formula (51). The compound of formula (51) was either reacted with an appropriate halide ($R_1$—X) or boronic acid ($R_1$—$B(OH)_2$) to yield the target compounds of structure (III) with $R_2$ as carbonitrile, $R_3$ as thiophene, and $R_1$ as defined above, as shown in Scheme 26.

structure (III) with $R_2$ as carbonitrile, $R_3$ as furan, and $R_1$ as defined above, as shown in Scheme 27.

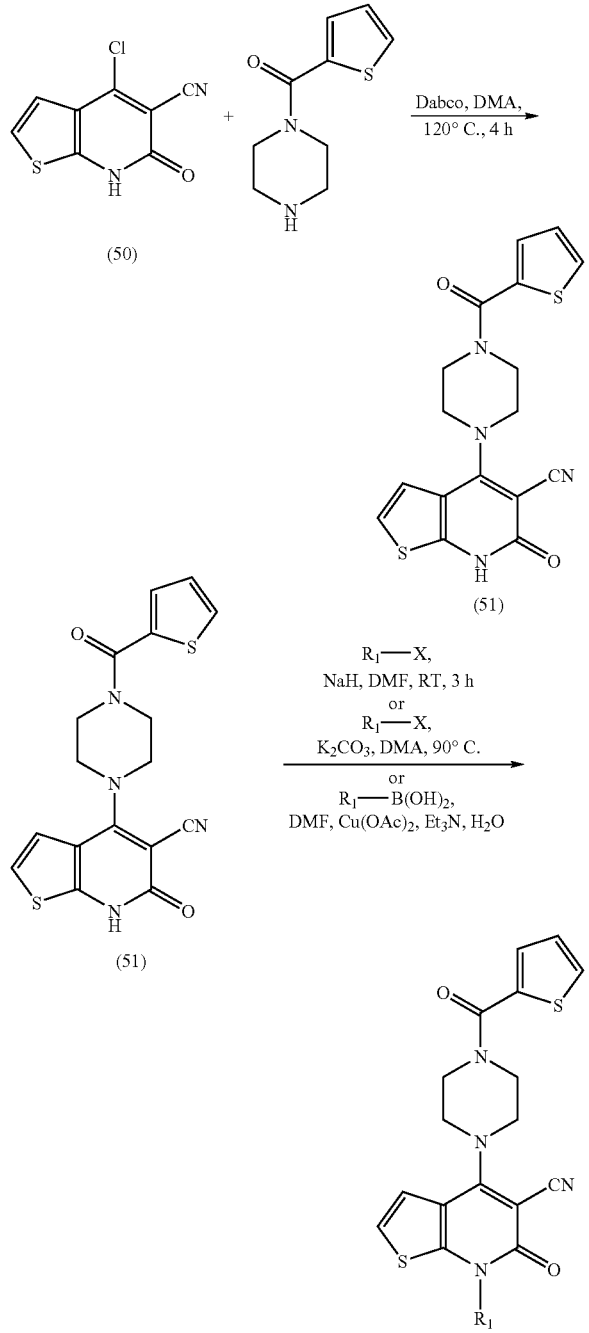

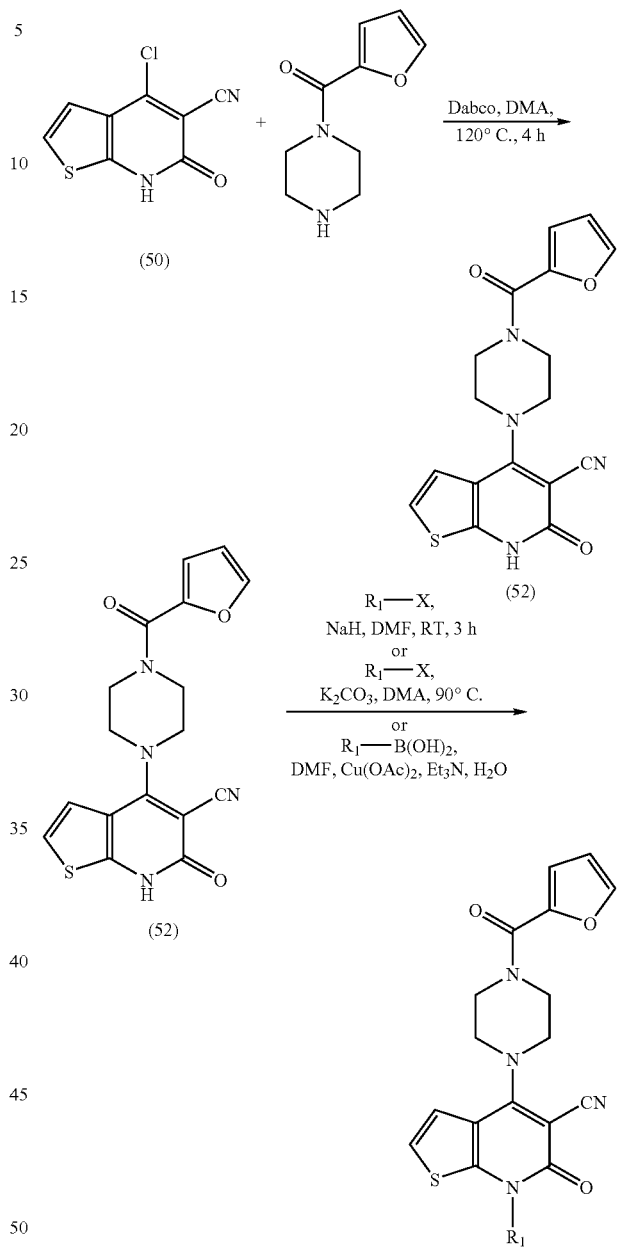

To yield compounds of structure (III) wherein $R_2$ is carbonitrile, $R_3$ is furan, and $R_1$ is as defined above, intermediate 4-chloro-6-oxo-6,7-dihydro-thieno[2,3-b]pyridine-5-carbonitrile, depicted by formula (50), was reacted with 1-(2-furyl)-piperazine to yield 4-[4-(furan-2-carbonyl)-piperazin-1-yl]-6-oxo-6,7-dihydro-thieno[2,3-b]-pyridine-5-carbonitrile, depicted by formula (52). This intermediate was either reacted with an appropriate halide ($R_1$—X) or boronic acid ($R_1$—$B(OH)_2$) to yield target compounds of Compounds of structure (III) with $R_2$ as carbonitrile, and $R_1$ and $R_3$ as defined above were also prepared from intermediate 4-chloro-6-oxo-6,7-dihydro-thieno[2,3-b]pyrdine-5-carbonitrile, depicted by formula (50). Intermediate 4-chloro-6-oxo-6,7-dihydro-thieno[2,3-b]pyridine-5-carbonitrile, depicted by formula (50), was reacted with tert-butyl-1-piperazine carboxylate to yield 4-(5-cyano-6-oxo-6,7-dihydro-thieno[2,3-b]-pyridine-4-yl)-piperazine-1-carboxylic acid tert-butyl ester, depicted by formula (53). This intermediate was either reacted with an appropriate halide ($R_1$—X) or boronic acid ($R_1$—$B(OH)_2$) to yield an intermediate of structure (54), which was deprotected and reacted with an appropriate acid chloride ($R_3$—COCl) or acid ($R_3$—COOH) to yield target compounds of structure (III) with $R_2$ as carbonitrile, and $R_1$ and $R_3$ as defined above, as shown in Scheme 28.

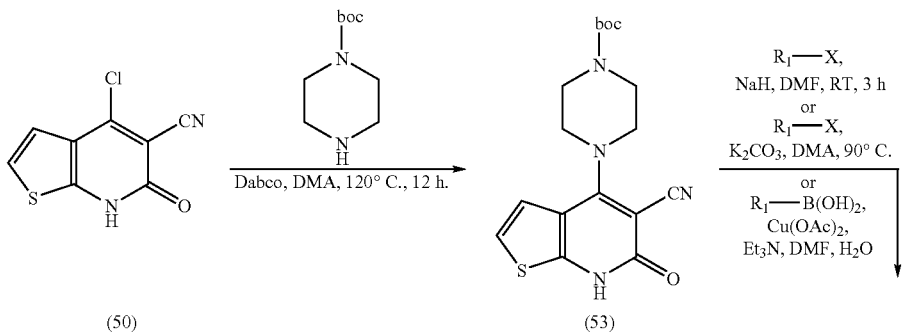

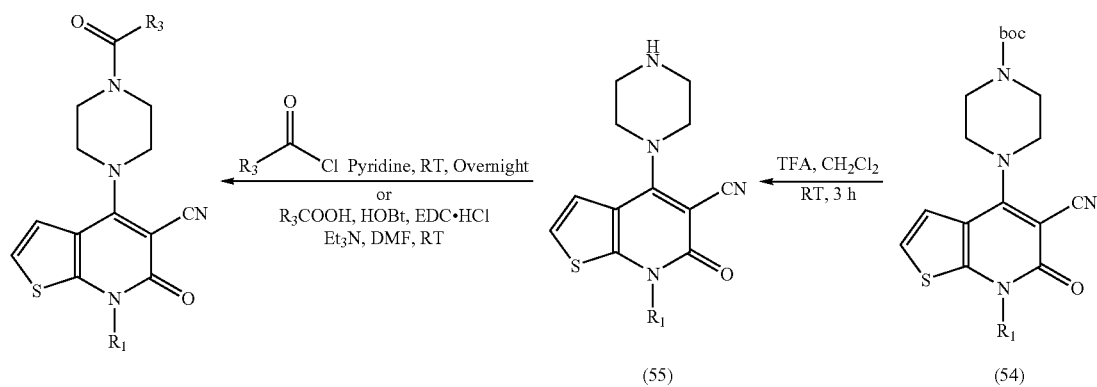

To yield compounds of structure (III) with $R_1$ as alkyl benzoic acid, and $R_2$ and $R_3$ as defined above, corresponding methyl or ethyl esters were prepared as shown in Scheme 24 or Scheme 28 above and hydrolyzed to corresponding acids by $BBr_3$, as shown in Scheme 29.

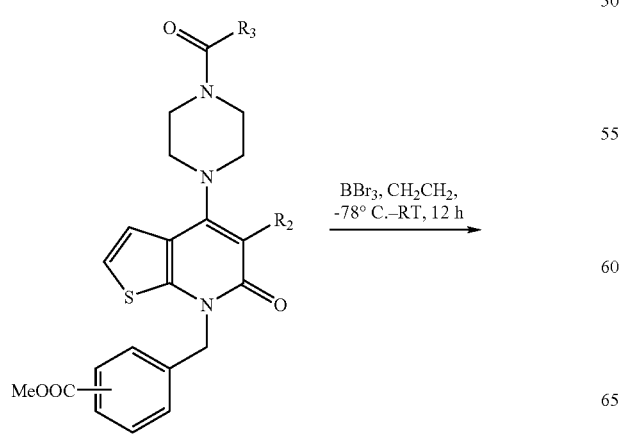

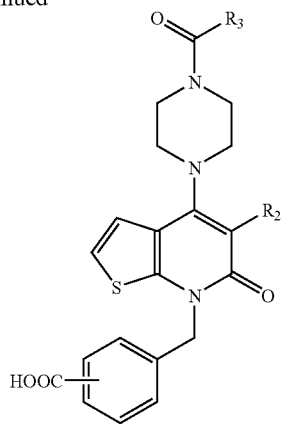

Alternative Method for the Preparation of Compounds of Structure (I)

In an alternative method for the preparation of compounds of structure (I) with $R_1$, $R_2$, $R_3$, X, and Y as defined above, appropriately substituted 1H-thieno[3,2-d][1,3]oxazine-2,4-dione, depicted by formula (54) in Scheme 30, was used as an intermediate. To prepare this intermediate, substituted 3-amino-thiophene-2-carboxylic acid ester was hydrolyzed to the corresponding 3-amino-thiophene-2-carboxylic acid, which was reacted with trichloromethyl chloroformate as shown in Scheme 30. Appropriate N-substitution was introduced by reacting substituted 1H-thieno[3,2-d][1,3]oxazine-2,4-dione, depicted by formula (54), with the corresponding halide ($R_1$—X). The N-substituted intermediate, depicted by formula (55), was then reacted with dialkyl malonate to yield the intermediate of general formula (56) which was chlorinated either by phosphorous oxychloride or by oxalyl chloride, as depicted in Scheme 30.

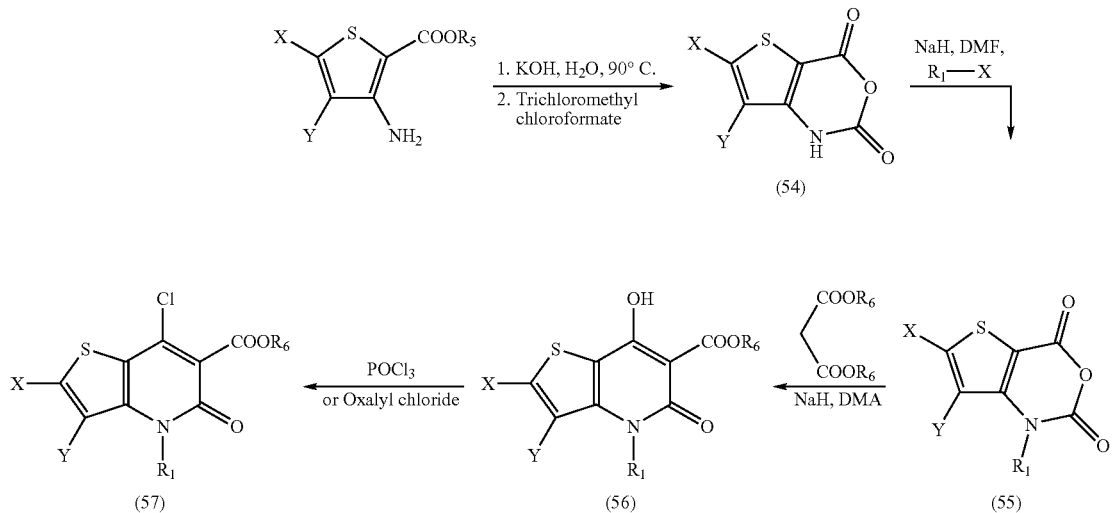

The chloro intermediate, depicted by formula (57), was reacted with piperazine to yield a piperazine intermediate, depicted by formula (58), as shown in Scheme 31. Acylation of the piperazine intermediate, depicted by formula (58), by an appropriate acyl halide ($R_3$—CO—Cl) or by coupling with an appropriate acid ($R_3$—COOH) yielded a compound of general formula (I) as shown in Scheme 31. Alternatively, the chloro intermediate was reacted with an acyl piperazine to yield a compound of general formula (I) with $R_1$, $R_2$, $R_3$, X, and Y as defined above, as shown in Scheme 31.

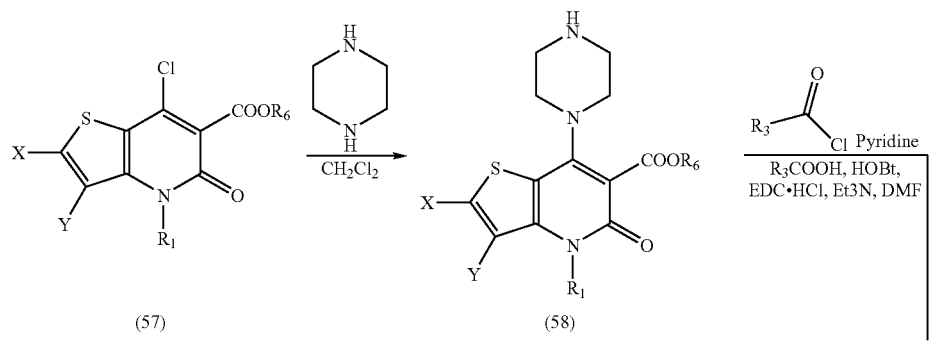

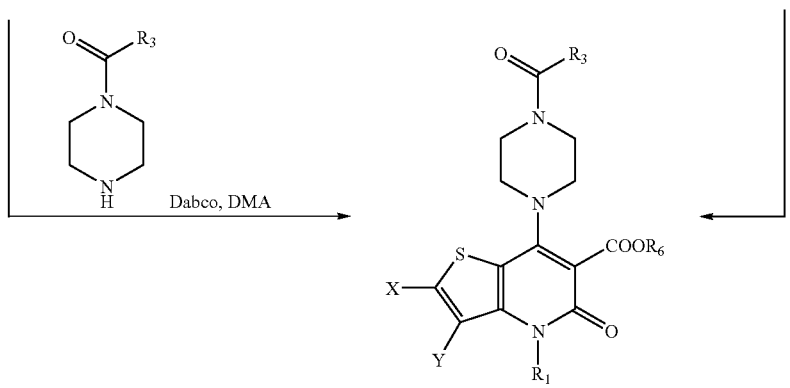

Alternative Method for the Preparation of Compounds of Structure (III)

In an alternative method for the preparation of compounds of structure (III) with $R_1$, $R_2$, $R_3$, X, and Y as defined above, an appropriately substituted 1H-thieno[2,3-d][1,3]oxazine-2,4-dione, depicted by formula (59) in Scheme 32, was used as an intermediate. To prepare this intermediate, a substituted 2-amino-thiophene-3-carboxylic acid ester was hydrolyzed to the corresponding 2-amino-thiophene-3-carboxylic acid, which was then reacted with trichloromethyl chloroformate as shown in Scheme 32. Appropriate N-substitution was introduced by reacting a substituted 1H-thieno[2,3-d][1,3]oxazine-2,4-dione, depicted by formula (59), with a corresponding halide ($R_1$—X). The N-substituted intermediate, depicted by formula (60), was then reacted with dialkyl malonate to yield an intermediate of general formula (61), which was chlorinated either by phosphorous oxychloride or by oxalyl chloride.

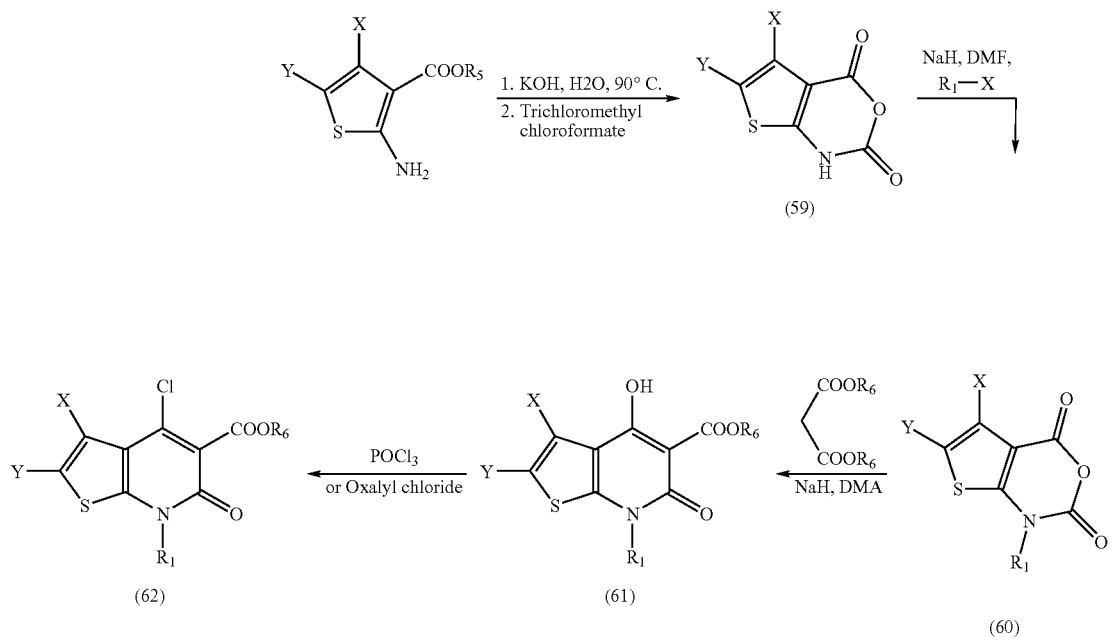

The chloro intermediate, depicted by formula (62), was reacted with piperazine to yield a piperazine intermediate, depicted by formula (63), as shown in Scheme 33. Acylation of the piperazine intermediate (63) by an appropriate acyl halide ($R_3$—CO—Cl) or by coupling with an appropriate acid ($R_3$—COOH) yielded a compound of general formula (III) as shown in Scheme 33. Alternatively, the chloro intermediate was reacted with acyl piperazine to yield a compound of general formula (III), with $R_1$, $R_2$, $R_3$, X, and Y as defined above, as shown in Scheme 33.

formula (4) below, was also prepared by an alternative route as shown in Scheme 34. In this method, methyl-3-aminothiophene-2-carboxylate was reacted with 4-methoxy benzylchloride to yield methyl 3-(4-methoxybenzylamino) thiophene-2-carboxylate, depicted by formula (65). This intermediate was reacted with ethylmalonyl chloride followed by a cyclization reaction to yield 7-hydroxy-4-(4-methoxybenzyl)-5-oxo-4,5-dihydro-thieno[3,2-b]pyridine-6-carboxylic acid ethyl ester, depicted by formula (67). Chlorination of 7-hydroxy-4-(4-methoxybenzyl)-5-oxo-4,5-

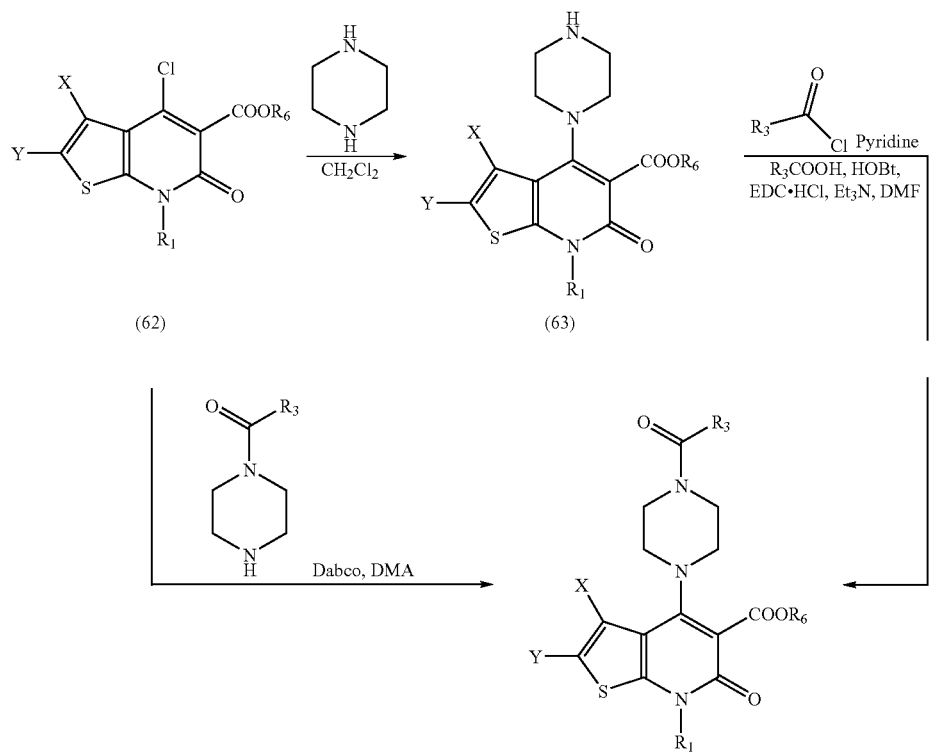

Scheme 33

Alternative Method for the Preparation of Intermediate 7-chloro-5-oxo-4,5-dihydro-thieno[3,2-b]pyridine-6-carboxylic acid ethyl ester (4)

The preferred intermediate in the preparation of compounds of structure (I), 7-chloro-5-oxo-4,5-dihydro-thieno[3,2-b]pyridine-6-carboxylic acid ethyl ester depicted by dihydro-thieno[3,2-b]pyridine-6-carboxylic acid ethyl ester, depicted by formula (67) by reacting with oxalyl chloride followed by deprotection yielded the intermediate 7-chloro-5-oxo-4,5-dihydro-thieno[3,2-b]pyridine-6-carboxylic acid ethyl ester, depicted by formula (4), as shown in Scheme 34.

Scheme 34

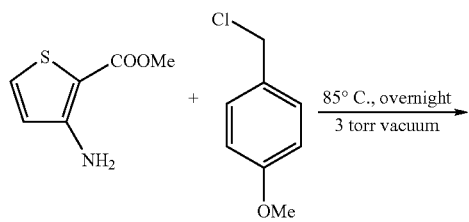

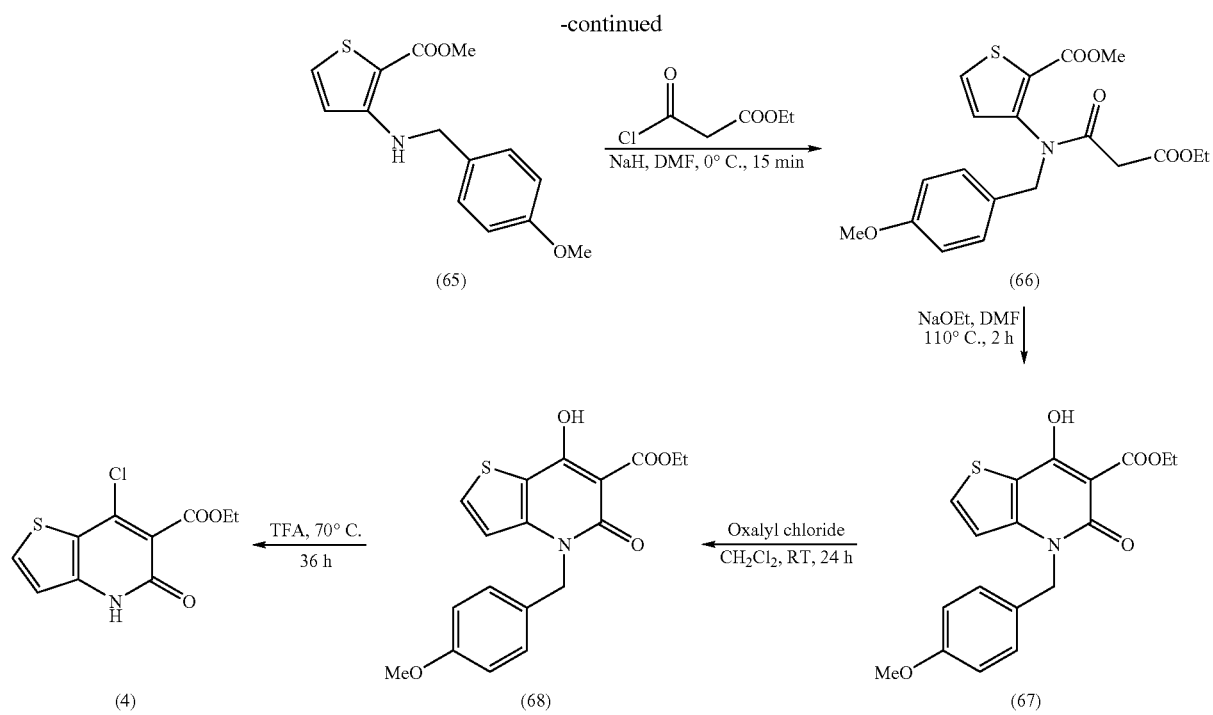

Experiments

Macrophage migration inhibitory factor inhibitors of preferred embodiments were prepared by the methods described in following examples.

Synthesis of 3-(2-ethoxycarbonyl-acetylamino)-thiophene-2-carboxylic acid methyl ester (1)

Ethylmalonyl chloride (1.93 mL, 15.22 mmol) was added to a solution of methyl-3-amino-thiophene-2-carboxylate (2 g, 12.70 mmol) in dry toluene (20 mL) and pyridine (1.23 mL, 15.22 mmol) at −10° C. The solution was stirred at −10° C. for 1 h and poured into ice water. The product was extracted by ethyl acetate. The combined organic phase was sequentially washed by diluted HCl solution, saturated NaHCO$_3$ solution, water, and brine. The organic phase was dried over MgSO$_4$ and concentrated to yield an oily residue. The residue was dissolved in hot ethanol and kept overnight at −4° C. The crystals formed were filtered off and filtrate was concentrated to yield 2.2 g (63%) of 3-(2-ethoxycarbonyl-acetylamino)-thiophene-2-carboxylic acid methyl ester as yellow viscous oil. $^1$H NMR (400 MHz, DMSO-d6) δ 1.21 (t, J=7.2 Hz, 3H), 3.68 (s, 2H), 3.84 (s, 3H), 4.15 (q, J=7.2 Hz, 2H), 7.91 (d, J=5.2 Hz, 1H), 7.93 (d, J=5.2 Hz, 1H), 10.52 (s, 1H) ppm; MS m/z=272 amu (M$^+$+1).

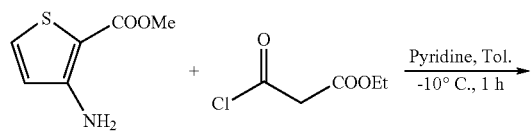

Synthesis of 7-hydroxy-5-oxo-4,5-dihydro-thieno[3,2-b]pyridine-6-carboxylic acid ethyl ester (2)

Sodium ethoxide (0.67 g, 9.29 mmol) was added to a solution of 3-(2-ethoxycarbonyl-acetylamino)-thiophene-2-carboxylic acid methyl ester (1) (2.18 g, 7.74 mmol) in anhydrous ethanol and refluxed overnight. The solution was cooled and excess solvent was distilled off The residue was dissolved in water and acidified by cold diluted HCl solution. The solids formed were filtered, washed by water, and dried under vacuum at room temperature to yield 1.0 g (55%) of 7-hydroxy-5-oxo-4,5-dihydro-thieno[3,2-b]pyridine-6-carboxylic acid ethyl ester as white solid. MP 218° C.; $^1$H NMR (400 MHz, DMSO-d6) δ 1.28 (t, J=7.2 Hz, 3H), 4.29 (q, J=7.2 Hz, 2H), 6.96 (d, J=5.6 Hz, 1H), 8.07 (d, J=5.6 Hz, 1H) ppm; MS m/z=240 amu (M$^+$+1).

Synthesis of 5,7-dichloro-thieno[3,2-b]pyridine-6-carboxylic acid ethyl ester (3)

A solution of 7-hydroxy-5-oxo-4,5-dihydro-thieno[3,2-b]pyridine-6-carboxylic acid ethyl ester (2) (1 g, 4.18 mmol) in neat phosphorous oxychloride was heated at 90° C. for 4 h. The solution was cooled and excess phosphorus oxychloride was distilled under vacuum. The residue was suspended in water, basified by solid NaHCO$_3$, and extracted by ethyl acetate. The organic phase was washed by saturated NaHCO$_3$ solution, water, and brine. The organic phase was dried over MgSO$_4$ and concentrated to yield 5,7-dichloro-thieno[3,2-b]pyridine-6-carboxylic acid ethyl ester (3) as white solids. Yield 0.56 g (52%); MP 73° C.; $^1$H NMR (400 MHz, DMSO-d6) δ 1.35 (t, J=7.2 Hz, 3H), 4.48 (q, J=7.2 Hz, 2H), 7.73 (d, J=5.6 Hz, 1H), 8.50 (d, J=5.6 Hz, 1H) ppm; MS m/z=259 amu (M$^+$).

Synthesis of 7-chloro-5-oxo-4,5-dihydro-thieno[3,2-b]pyridine-6-carboxylic acid ethyl ester (4)

Ammonium acetate (161 mg, 2.1 mmol) was added to a stirred solution of 5,7-dichloro-thieno[3,2-b]pyridine-6-carboxylic acid ethyl ester (3) (530 mg, 1.9 mmol) in glacial acetic acid at room temperature. The solution was heated at 140° C. for 48 h. The hot solution was poured into ice water. The solids formed were filtered, washed by water, and dried. The crude product was recrystallized by CH$_2$Cl$_2$ to yield 273 mg (60%) of 7-chloro-5-oxo-4,5-dihydro-thieno[3,2-b]pyridine-6-carboxylic acid ethyl ester as white solids. MP 206° C.; $^1$H NMR (400 MHz, DMSO-d6) δ 1.28 (t, J=7.2 Hz, 3H), 4.29 (q, J=7.2 Hz, 2H), 7.10 (d, J=5.2 Hz, 1H), 8.13 (d, J=5.2 Hz, 1H) ppm; MS m/z=240 amu (M$^+$+1).

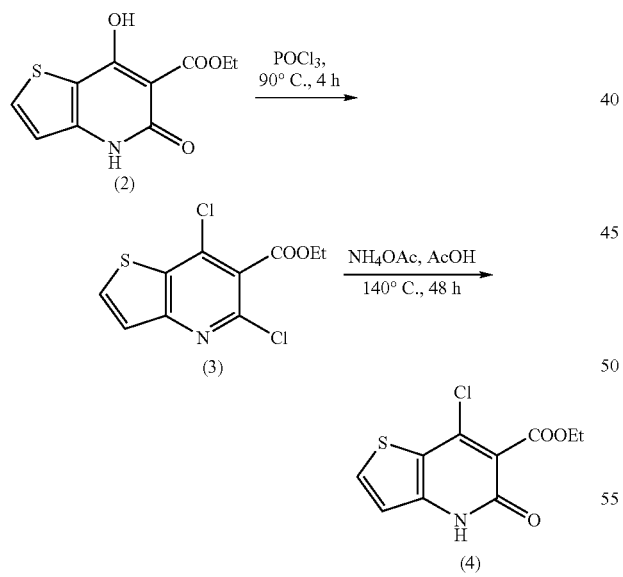

Synthesis of 5-oxo-7-[4-(thiophene-2-carbonyl)-piperazin-1-yl]-4,5-dihydro-thieno[3,2-b]pyridine-6-carboxylic acid ethyl ester (5)

1,4-Diazabicyclo[2.2.2]octane (224 mg, 2 mmol) was added to a solution of 7-chloro-5-oxo-4,5-dihydro-thieno[3,2-b]pyridine-6-carboxylic acid ethyl ester (4) (240 mg, 1 mmol) and piperazin-1-yl-thiophene-2-yl-methanone (215 mg, 1.1 mmol) in dry DMA. The solution was heated at 120° C. for 2 h. The solution was cooled and poured into ice water. The solids formed were filtered, washed by water, and dried to yield 5-oxo-7-[4-(thiophene-2-carbonyl)-piperazin-1-yl]-4,5-dihydro-thieno[3,2-b]pyridine-6-carboxylic acid ethyl ester (400 mg, 96%) as white solids. MP 252° C.; $^1$H NMR (400 MHz, DMSO-d6) δ 1.27 (t, J=7.2 Hz, 3H), 3.31 (m, 4H), 3.77 (m, 4H), 4.24 (q, J=7.2 Hz, 2H), 6.97 (d, J=5.6 Hz, 1H), 7.15 (dd, J=3.6, 4.8 Hz, 1H), 7.47 (dd, J=1.2, 3.6 Hz, 1H), 7.80 (dd, J=1.2, 4.8 Hz, 1H), 7.96 (d, J=5.6 Hz, 1H), 12.10 (s, 1H) ppm; MS m/z=418 amu (M$^+$+1).

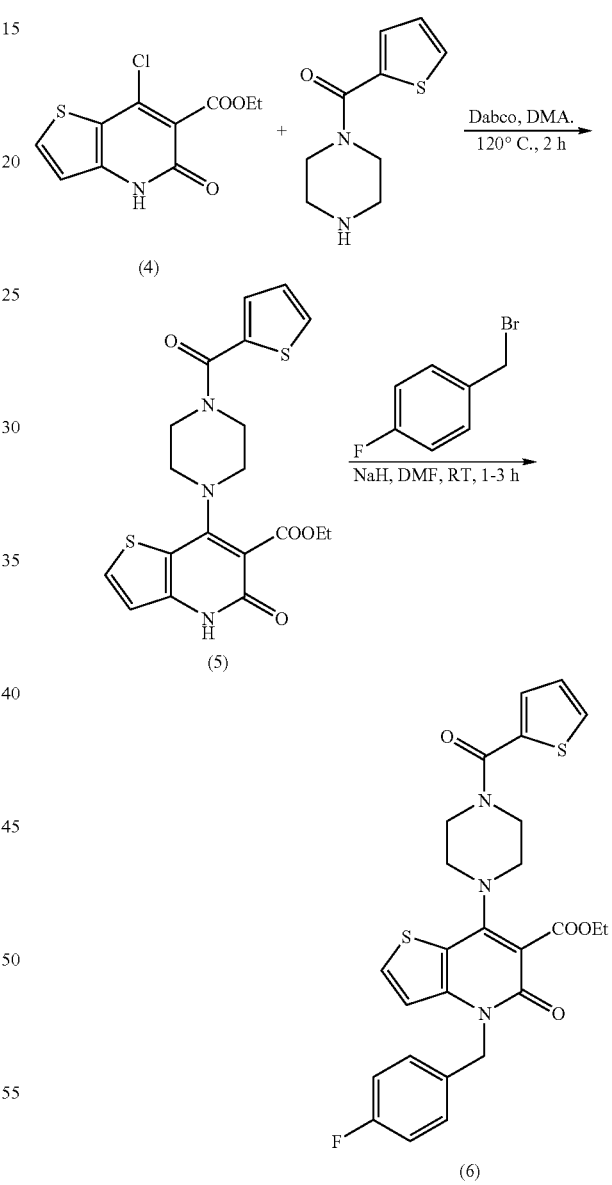

Synthesis of 4-(4-fluoro-benzyl)-5-oxo-7-[4-(thiophene-2-carbonyl)-piperazin-1-yl]-4,5-dihydro-thieno[3,2-b]pyridine-6-carboxylic acid ethyl ester (6)

A solution of 5-oxo-7-[4-(thiophene-2-carbonyl)-piperazin-1-yl]-4,5-dihydro-thieno[3,2-b]pyridine-6-carboxylic acid ethyl ester (5) (232 mg, 0.55 mmol) in dry DMF was added to a suspension of NaH (60% in mineral oil, 24 mg, 0.61 mmol) at room temperature. The solution was stirred at room temperature for 15 min. 4-Fluorobenzylbromide (76 μL, 0.61 mmol) was added to the solution through a syringe and further stirred at room temperature for 1 h. The solution was poured into ice water and the solids formed were filtered, washed by cold water, and dried. The crude product was purified by flash chromatography eluting with 0-2% methanol in $CH_2Cl_2$ gradient to yield 207 mg (90%) of 4-(4-fluoro-benzyl)-5-oxo-7-[4-(thiophene-2-carbonyl)-piperazin-1-yl]-4,5-dihydro-thieno[3,2-b]pyridine-6-carboxylic acid ethyl ester as white solids. $^1$H NMR (400 MHz, DMSO-d6) δ 1.28 (t, J=7.2 Hz, 3H), 3.34 (m, 4H), 3.80 (m, 4H), 4.27 (q, J=7.2 Hz, 2H), 5.34 (s, 2H), 7.14-7.18 (m, 3H), 7.29-7.35 (m, 3H), 7.48 (dd, J=1.2, 3.6, Hz, 1H), 7.80 (dd, J=1.2, 5.2 Hz, 1H), 8.04 (d, J=5.6 Hz, 1H) ppm; MS m/z=526 amu ($M^+$+1). Anal. ($C_{26}H_{24}FN_3O_4S_2$) C, H, N.

Synthesis of 5-oxo-4-(2-oxo-2-phenyl-ethyl)-7-[4-(thiophene-2-carbonyl)-piperazin-1-yl]4,5-dihydro-thieno[3,2-b]pyridine-6-carboxylic acid ethyl ester (7)

A solution of 5-oxo-7-[4-(thiophene-2-carbonyl)-piperazin-1-yl]-4,5-dihydro-thieno[3,2-b]pyridine-6-carboxylic acid ethyl ester (5) (750 mg, 1.79 mmol), Cs2CO3 (1.76 g, 5.40 mmol), 2-chloroacetophenone (0.333 g, 2.15 mmol) in dry NMP was heated overnight at 90° C. The solution was poured into ice water and the solids formed were filtered, washed by cold water, and dried. The crude product was purified by recrystallization with acetone. MP 240° C. 1H-NMR (DMSO-d6) δ 1.26 (t, J=7.2 Hz, 3H), 3.39 (m, 4H), 3.83 (m, 4H), 4.23 (q, J=7.2 Hz, 2H), 4.23 (q, J=7.2 Hz, 2H), 5.75 (s, 2H), 7.16 (m, 1H), 7.34 (d, J=5.6 Hz, 1H), 7.50 (dd, J=1.2, 3.6 Hz, 1H), 7.61 (t, J=7.6 Hz, 2H), 7.74 (m, 1H), 7.80 (dd, J=1.2, 5.2 Hz, 1H), 8.01 (d, J=7.0 Hz, 1H), 8.10 (m, 2H); EIMS m/z 536(M+1).

Synthesis of 5-oxo-4-pyridin-3-yl-methyl-7-[4-(thiophene-2-carbonyl)-piperazin-1-yl]-4,5-dihydro-thieno[3,2-b]pyrdine-6-carboxylic acid ethyl ester (8)

A solution of 5-oxo-7-[4-(thiophene-2-carbonyl)-piperazin-1-yl]-4,5-dihydro-thieno[3,2-b]pyridine-6-carboxylic acid ethyl ester (5) (856 mg, 2.05 mmol), Cs2CO3 (2.75 g, 8.4 mmol), 3-chloromethyl pyridine hydrochloride (0.370 g, 2.25 mmol) and KI (1 g) in dry NMP was heated overnight at 90° C. The solution was poured into ice water and the solids formed were filtered, washed by cold water, and dried. The crude product was purified by reverse phase flash chromatography in combiflash eluting with water/acetonitrile gradient. 1H-NMR (DMSO-d6) δ 3.13 (t, J=7.2 Hz, 3H), 3.80 (m, 4H), 4.27 (q, J=7.2 Hz, 2H), 5.40 (s, 2H), 7.15 (m, 1H), 7.35 (m, 1H), 7.44 (d, J=6.0 Hz, 1H), 7.48 (dd, J=1.2, 3.6 Hz, 1H), 7.60 (m, 1H), 7.79 (dd, J=0.8, 4.8 Hz, 1H), 8.06 (d, J=5.6 Hz, 1H), 8.47 (dd, J=1.6, 4.8 Hz, 1H), 8.56 (d, J=1.6 Hz, 1H); EIMS m/z 509 (M+1).

Synthesis of 4-(3-fluoro-benzyl)-5-oxo-7-[4-(thiophene-2-carbonyl)-piperazin-1-yl]-4,5-dihydro-thieno[3,2-b]pyridine-6-carboxylic acid ethyl ester (9)

A solution of 5-oxo-7-[4-(thiophene-2-carbonyl)-piperazin-1-yl]-4,5-dihydro-thieno[3,2-b]pyridine-6-carboxylic acid ethyl ester (5) (2 g, 4.79 mmol) in dry DMF was added to a suspension of NaH (60% in mineral oil, 230 mg, 5.74 mmol) at room temperature. The solution was stirred at room temperature for 30 min. 3-Fluorobenzylbromide (0.705 mL, 5.74 mmol) was added to the solution through a syringe and the solution was further stirred at room temperature for 3 h. The solvent was evaporated under vacuum and the residue was suspended in water, sonicated briefly, and filtered. The solids were washed by cold water and air dried. The crude product was purified by flash chromatography eluting with 0-2% methanol in $CH_2Cl_2$ gradient to yield 1.2 g (48%) of 4-(3-fluoro-benzyl)-5-oxo-7-[4-(thiophene-2-carbonyl)-piperazin-1-yl]-4,5-dihydro-thieno[3,2b]pyridine-6-carboxylic acid ethyl ester as white solids. MP 95-113° C. $^1$H-NMR (DMSO-$d_6$) δ 1.29 (t, J=7.2 Hz, 3H), 3.37 (m, 4H), 3.82 (m, 4H), 4.27 (q, J=7.2 Hz, 2H), 5.38 (s, 2H), 7.05-7.16 (m, 4H), 7.33 (d, J=5.6 Hz, 1H), 7.36 (m, 1H), 7.48 (dd, J=1.2, 3.6 Hz, 1H), 7.79 (dd, J=1.2, 5.2 Hz, 1H), 8.03 (d, J=5.6 Hz, 1H); EIMS m/z 526 (M+1). Anal. ($C_{26}H_{24}FN_3O_4S_2$) C, H, N.

Synthesis of 7-[4-(furan-2-carbonyl)-piperazin-1-yl]-5-oxo-4,5-dihydro-thieno[3,2-b]pyridine-6-carboxylic acid ethyl ester (10)

1,4-Diazabicyclo[2.2.2]octane (3.08 g, 27.45 mmol) was added to a solution of 7-chloro-5-oxo-4,5-dihydro-thieno[3,2-b]pyridine-6-carboxylic acid ethyl ester (4) (3.54 mg, 13.77 mmol) and 1-(2-furayl)-piperazine (3.22 g, 17.87 mmol) in dry DMA. The solution was heated at 120° C. for 2 h. The solution was cooled and poured into ice water. The solids formed were filtered, washed by water, and dried to yield 7-[4-(furan-2-carbonyl)-piperazin-1-yl]-5-oxo-4,5-dihydro-thieno[3,2-b]pyridine-6-carboxylic acid ethyl ester as brown solid. Yield 5.86 g (99%). $^1$H-NMR (DMSO-$d_6$) δ 1.26 (t, J=7.2 Hz, 3H), 3.34 (m, 4H), 3.80 (br, 4H), 4.23 (q, J=7.2 Hz, 2H), 6.65 (m, 1H), 6.97 (d, J=5.6 Hz, 1H), 7.06 (dd, J=0.8, 3.2 Hz, 1H), 7.87 (dd, J=0.8, 2.0 Hz, 1H), 7.96 (d, J=5.2 Hz, 1H), 12.09 (br, 1H); EIMS m/z 402 (M+1).

Synthesis of 4-(4-fluoro-benzyl)-7-[4-(furan-2-carbonyl)-piperazin-1-yl]-5-oxo-4,5-dihydro-thieno[3,2-b]pyrdine-6-carboxylic acid ethyl ester (11)

A solution of 7-[4-(furan-2-carbonyl)-piperazin-1-yl]-5-oxo-4,5-dihydro-thieno[3,2-b]pyrdine-6-carboxylic acid ethyl ester (10) (750 mg, 1.87 mmol), $Cs_2CO_3$ (1.83 g, 5.63 mmol), 4-fluoro benzyl bromide (0.276 mL, 2.24 mmol) in dry NMP was heated overnight at 90° C. The solution was poured into ice water and the solids formed were filtered, washed by cold water, and dried. The crude product was purified by reverse phase flash chromatography in combi-flash eluting with water/acetonitrile gradient. Yield 240 mg (25%). $^1$H-NMR (DMSO-$d_6$) δ 1.27 (t, J=6.8 Hz, 3H), 3.36 (m, 4H), 3.82 (m, 4H), 4.26 (q, J=6.8 Hz, 2H), 5.35 (s, 2H), 6.65 (m, 1H), 7.06 (dd, J=0.8, 3.6 Hz, 1H), 7.16 (m, 2H), 7.32 (m, 3H), 7.87 (m, 1H), 8.03 (d, J=5.6 Hz, 1H); EIMS m/z 510 (M+1).

Synthesis of 4-(3-fluoro-benzyl)-7-[4-(furan-2-carbonyl)-piperazin-1-yl]-5-oxo-4,5-dihydro-thieno[3,2-b]pyrdine-6-carboxylic acid ethyl ester (12)

This compound was prepared from 7-[4-(furan-2-carbonyl)-piperazin-1-yl]-5-oxo-4,5-dihydro-thieno[3,2-b]pyridine-6-carboxylic acid ethyl ester (10) and 3-fluoro benzyl bromide by applying a similar method as described for 4-(4-fluoro-benzyl)-7-[4-(furan-2-carbonyl)-piperazin-1-yl]-5-oxo-4,5-dihydro-thieno[3,2-b]pyridine-6-carboxylic acid ethyl ester (11). Yield 210 mg, (22%). $^1$H-NMR (DMSO-$d_6$): δ 1.28 (t, J=7.2 Hz, 3H), 3.82 (m, 4H), 4.26 (q, J=7.2 Hz, 2H), 5.38 (s, 2H), 6.65 (m, 1H), 7.07 (m, 4H), 7.34 (d, J=5.6 Hz, 1H), 7.37 (m, 1H), 7.88 (m, 1H), 8.03 (d, J=5.6 Hz, 1H); EIMS m/z 510 (M+1).

Synthesis 7-[4-(furan-2-carbonyl)-piperazin-1-yl]-5-oxo-4-(2-oxo-2-phenyl-ethyl)-4,5-dihydro-thieno[3,2-b]pyridine-6-carboxylic acid ethyl ester (13)

This compound was prepared from 7-[4-(furan-2-carbonyl)-piperazin-1-yl]-5-oxo-4,5-dihydro-thieno[3,2-b]pyridine-6-carboxylic acid ethyl ester (10) and 2-chloroacetophenone by applying similar method as described for 4-(4-fluoro-benzyl)-7-[4-(furan-2-carbonyl)-piperazin-1-yl]-5-oxo-4,5-dihydro-thieno[3,2-b]pyridine-6-carboxylic acid ethyl ester (11). MP 246° C. $^1$H-NMR (DMSO-$d_6$) δ 1.25 (t, J=7.2 Hz, 3H), 3.85 (m, 4H), 4.23 (q, J=6.8 Hz, 2H), 5.75 (s, 2H), 6.66 (m, 1H), 7.07 (d, J=3.2 Hz, 1H), 7.34 (d, J=5.6 Hz, 1H), 7.61 (t, J=7.6 Hz, 2H), 7.73 (t, J=7.6 Hz, 1H), 7.88 (d, J=0.8 Hz, 1H), 8.01 (d, J=5.6 Hz, 1H), 8.10 (d, J=7.6 Hz, 2H); EIMS m/z 520 (M+1).

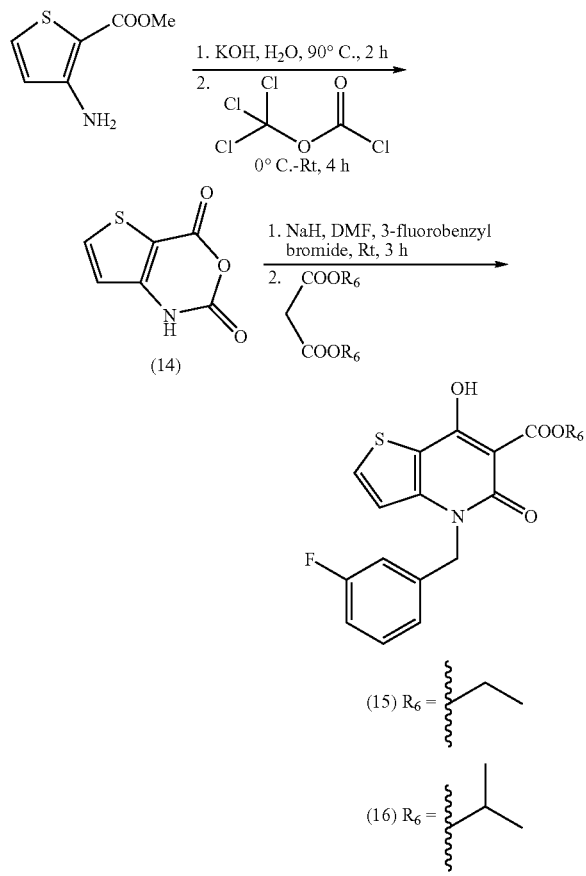

Synthesis of 1H-thieno[3,2-d][1,3]oxazine-2,4-dione (14)

Methyl 3-aminothiophene-2-carboxylate (31.0 g, 0.20 mol) was added to a solution of potassium hydroxide (22.68 g, 0.40 mol) in 1 L water. The solution was heated at 90° C. for 2 hours. The solution was then cooled to 0° C. and trichloromethyl chloroformate (35.7 mL, 0.30 mol) was added slowly, maintaining the temperature between 0° C. and 10° C. The solution was stirred at 0° C. for 4 hours, and then allowed to warm up gradually to room temperature and stirred for another 3 hours. The precipitated solid product was collected by vacuum filtration to give 28.5 g (85% yield) 1H-thieno[3,2-d][1,3]oxazine-2,4-dione. $^1$H-NMR (DMSO-$d_6$) δ 6.94 (d, J=5.0 Hz, 1H), 8.24 (d, J=5.0 Hz, 1H), 12.26 (b, 1H) ppm; EIMS m/z 170 (M+1).

Synthesis of 4-(3-fluoro-benzyl)-7-hydroxy-5-oxo-4,5-dihydro-thieno[3,2-b]pyridine-6-carboxylic acid ethyl ester (15)

1H-Thieno[3,2-d][1,3]oxazine-2,4-dione (14) (40.0 g, 0.24 mol) was added to a suspension of sodium hydride (60% dispersion in mineral oil, 21.75 g, 0.54 mol) in 300 mL anhydrous DMF stirred under argon at −10° C. After stirring at −10° C. for 15 minutes, 3-fluorobenzylbromide (29.73 mL, 0.24 mol) was added to the solution. The solution was allowed to come to room temperature and further stirred for 3 hours. The solution was again cooled to −10° C., and diethylmalonate (36.62 mL, 0.24 mol) was added slowly. The solution was then heated at 110° C. for 45 minutes. A large amount of gas evolved very quickly once the solution was heated, so this heating step was done in a flask at least 5 times as large as the reaction volume, and a reflux condenser was used which was open to the air, and not sealed with a septum. The reaction mixture was cooled to room temperature, and poured into a solution of potassium carbonate (32.68 g, 0.24 mol) in 2.5 L of water. This aqueous solution was stirred for 5 minutes, and then it was extracted 2 times with 600 mL ethyl acetate and 2 times with 600 mL isopropyl ether. These organic phases were discarded. The aqueous solution was then acidified slowly to pH 2 with 4M HCl. The precipitated solid product was collected by vacuum filtration to yield 60.1 g (73% yield) of 4-(3-fluoro-benzyl)-7-hydroxy-5-oxo-4,5-dihydro-thieno[3,2-b]pyridine-6-carboxylic acid ethyl ester. $^1$H-NMR (DMSO-$d_6$) δ 1.30 (t, J=7.2 Hz, 3H), 4.32 (q, J=7.2 Hz, 2H), 5.36 (s, 2H), 7.06 (m, 3H), 7.33 (m, 2H), 8.15 (m, 1H), 13.37 (s, 1H) ppm, EIMS m/z 348 (M+1).

Synthesis of 4-(3-fluoro-benzyl)-7-hydroxy-5-oxo-4,5-dihydro-thieno[3,2-b]pyridine-6-carboxylic acid isopropl ester (16)

This compound was prepared by using the same procedure as described for 4-(3-fluoro-benzyl)-7-hydroxy-5-oxo-4,5-dihydro-thieno[3,2-b]pyridine-6-carboxylic acid ethyl ester (15) by using diisopropyl malonate. $^1$H-NMR (DMSO-$d_6$) δ 1.30 (d, J=6.4 Hz, 6H), 5.17 (m, 1H), 5.36 (s, 2H), 7.08 (m, 3H), 7.31 (m, 2H), 8.15 (dd, J=2.4, 5.2 Hz, 1H), 13.41 (b, 1H) ppm; EIMS m/z 362 (M+1).

Synthesis of 7-chloro-4-(3-fluoro-benzyl)-5-oxo-4,5-dihydro-thieno[3,2-b]pyridine-6-carboxylic acid ethyl ester (17)

4-(3-Fluoro-benzyl)-7-hydroxy-5-oxo-4,5-dihydro-thieno[3,2-b]pyridine-6-carboxylic acid ethyl ester (15) (60 g, 0.17 mol) was dissolved in 600 mL anhydrous DMF under a blanket of argon and cooled to −30° C. Oxalyl chloride (40.7 mL, 0.47 mol) was then added very slowly (producing a large volume of gas), with the reaction vessel open to the atmosphere. The solution was then heated to 75° C. for 2 hours. The solution was cooled to room temperature and poured into a solution of 150 g. NaCl in 6 L ice water without stirring. The mixture was allowed to sit without stirring for 15 minutes, and was then stirred vigorously for 1 minute with a spatula. The precipitated solid product was collected by vacuum filtration to yield 55 g (87% yield) of 7-chloro-4-(3-fluoro-benzyl)-5-oxo-4,5-dihydro-thieno[3,2-b]pyridine-6-carboxylic acid ethyl ester. $^1$H-NMR (DMSO-d$_6$) δ 1.30 (t, J=7.2 Hz, 3H), 4.34 (q, J=7.2 Hz, 2H), 5.45 (s, 2H), 7.06-7.17 (m, 3H), 7.37 (m, 1H), 7.49 (d, J=5.6 Hz, 1H), 8.20 (d, J=5.6 Hz, 1H) ppm; EIMS m/z 366 (M+1).

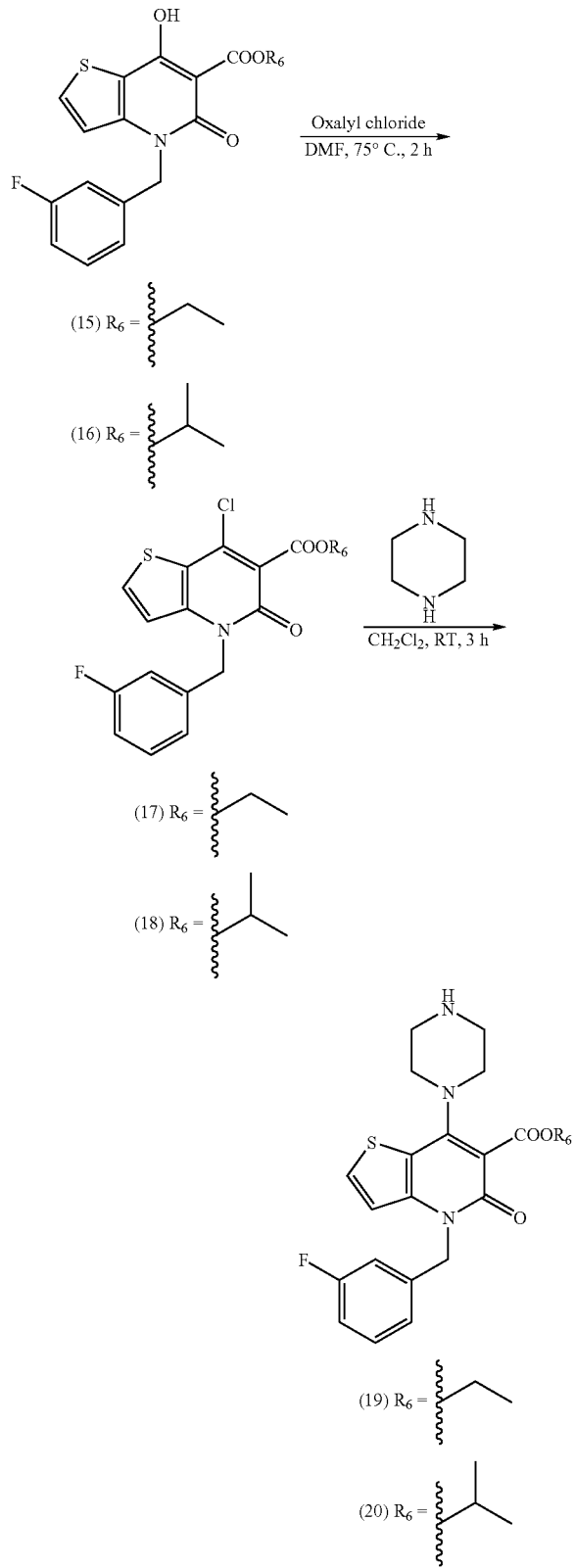

Synthesis of 7-chloro-4-(3-fluoro-benzyl)-5-oxo-4,5-dihydro-thieno[3,2-b]pyridine-6-carboxylic acid isopropyl ester(18)

This compound was prepared from 4-(3-fluoro-benzyl)-7-hydroxy-5-oxo-4,5-dihydro-thieno[3,2-b]pyridine-6-carboxylic acid isopropyl ester (16) by applying the same procedure as described for 7-chloro-4-(3-fluoro-benzyl)-5-oxo-4,5-dihydro-thieno[3,2-b]pyrdine-6-carboxylic acid ethyl ester (17). $^1$H-NMR (DMSO-d$_6$): δ 1.31 (d, J=6.4 Hz, 6H), 5.16 (m, 1H), 5.45 (s, 2H), 7.05-7.16 (m, 3H), 7.38 (m, 1H), 7.49 (d, J=5.2 Hz, 1H), 8.19 (d, J=5.6 Hz, 1H) ppm; EIMS m/z 380 (M+1).

Synthesis of 4-(3-fluoro-benzyl)-5-oxo-7-piperazin-1-yl-4,5-dihydro-thieno[3,2-b]pyridine-6-carboxylic acid ethyl ester (19)

7-Chloro-4-(3-fluoro-benzyl)-5-oxo-4,5-dihydro-thieno[3,2-b]pyridine-6-carboxylic acid ethyl ester (17) (10 g, 27.39 mmol) was added slowly to a solution of piperazine (9.42 g, 109 mmol) in dichloromethane. The solution was stirred at room temperature for 3 h. The solvent was evaporated under vacuum. The residue was suspended in water, stirred vigorously at room temperature, and filtered. The solids were again dissolved in dichloromethane and washed by water. The organic phase was dried over MgSO$_4$ and concentrated to yield 9.63 g (84%) of 4-(3-fluoro-benzyl)-5-oxo-7-piperazin-1-yl-4,5-dihydro-thieno[3,2-b]pyridine-6-carboxylic acid ethyl ester. $^1$H-NMR (DMSO-d$_6$) δ 1.29 (m, 3H), 2.81 (m, 4H), 3.21 (m, 4H), 4.25 (m, 2H), 5.35 (s, 2H), 7.12 (m, 3H), 7.30 (m, 2H), 7.97 (m, 1H); EIMS m/z 416 (M+1).

Synthesis of 4-(3-fluoro-benzyl)-5-oxo-7-piperazin-1-yl-4,5-dihydro-thieno[3,2-b]pyridine-6-carboxylic acid isopropyl ester (20)

This compound was prepared from 7-chloro-4-(3-fluoro-benzyl)-5-oxo-4,5-dihydro-thieno[3,2-b]pyridine-6-carboxylic acid isopropyl ester (18) by applying the same procedure as described for 4-(3-fluoro-benzyl)-5-oxo-7-piperazin-1-yl-4,5-dihydro-thieno[3,2-b]pyridine-6-carboxylic acid ethyl ester (19). $^1$H-NMR (DMSO-d$_6$) δ 1.28 (d, J=6.0 Hz, 6H), 2.81 (m, 4H), 3.22 (m, 4H), 5.07 (m, 1H), 5.36 (s, 2H), 7.10 (m, 3H), 7.29 (m, 1H), 7.35 (m, 1H), 7.98 (m, 1H); EIMS m/z 430 (M+1).

Synthesis of 4-(3-fluoro-benzyl)-7-[4-(5-fluoro-thiophene-2-carbonyl)-piperazin-1-yl]-5-oxo-4,5-dihydro-thieno[3,2-b]pyridine-6-carboxylic acid isopropyl ester (21)

A solution of 4-(3-fluoro-benzyl)-5-oxo-7-piperazin-1-yl-4,5-dihydro-thieno[3,2-b]pyrdine-6-carboxylic acid isopropyl ester (20) (2 g, 4.65 mmol), HOBt (0.692 g, 5.12 mmol), EDC.HCl (0.982 g, 5.12), triethylamine (0.971 mL, 6.98 mmol) and 5-fluoro-thiophene-2-carboxylic acid (0.749 g, 5.12 mmol) was stirred overnight at room temperature. The solution was poured into 2.5% NaHCO$_3$ solution and the solids formed were filtered, washed by cold water and air dried. The crude product was purified by flash chromatography eluting with 0-10% methanol in CH$_2$Cl$_2$ gradient to yield 2.16 g (83%) of 4-(3-fluoro-benzyl)-7-[4-(5-fluoro-thiophene-2-carbonyl)-piperazin-1-yl]-5-oxo-4,5-dihydro-thieno[3,2-b]pyrdine-6-carboxylic acid isopropyl ester. $^1$H-NMR (DMSO-d$_6$) δ 1.29 (d, J=6.0 Hz, 6H), 3.37 (m, 4H), 3.79 (m, 4H), 5.10 (m, 1H), 5.38 (s, 2H), 6.80 (m, 1H), 7.07 (m, 3H), 7.28 (t, J=3.6 Hz, 1H), 7.32 (d, J=5.6 Hz, 1H), 7.37 (m, 1H), 8.02 (d, J=5.6 Hz, 1H); EIMS m/z 558 (M+1).

Synthesis of 4-(3-fluoro-benzyl)-7-[4-(5-fluoro-thiophene-2-carbonyl)-piperazin-1-yl]-5-oxo-4,5-dihydro-thieno[3,2-b]pyridine-6-carboxylic acid ethyl ester (22)

This compound was prepared from 4-(3-fluoro-benzyl)-5-oxo-7-piperazin-1-yl-4,5-dihydro-thieno[3,2-b]pyridine-6-carboxylic acid ethyl ester (19) by applying the same procedure as described for 4-(3-fluoro-benzyl)-7-[4-(5-fluoro-thiophene-2-carbonyl)-piperazin-1-yl]-5-oxo-4,5-dihydro-thieno[3,2-b]pyridine-6-carboxylic acid isopropyl ester (21). Yield 2.22 g (85%). $^1$H-NMR (DMSO-d$_6$) δ 1.29 (t, J=7.2 Hz, 3H), 3.39 (m, 4H), 3.82 (m, 4H), 4.27 (q, J=7.2 Hz, 2H), 5.38 (s, 2H), 6.80 (m, 1H), 7.10 (m, 3H), 7.29 (t, J=3.6 Hz, 1H), 7.33 (d, J=5.6 Hz, 1H), 7.36 (m, 1H), 8.03 (d, J=5.6 Hz, 1H); EIMS m/z 544 (M+1).

Alternative Method for the Synthesis of 4-(3-fluoro-benzyl)-5-oxo-7-[4-(thiophene-2-carbonyl)-piperazin-1-yl]-4,5-dihydro-thieno[3,2-b]pyridine-6-carboxylic acid ethyl ester (9)

A solution of 7-chloro-4-(3-fluoro-benzyl)-5-oxo-4,5-dihydro-thieno[3,2-b]pyridine-6-carboxylic acid ethyl ester (17) (45 g, 123 mmol), 1,4-diazabicyclo[2.2.2]octane (15.9 g, 141 mmol) and piperazin-1-yl-thiophene-2-yl-methanone (27.8 g, 141 mmol) in dry DMF was heated at 110° C. for 7 h under argon. The solution was cooled and poured into 2% ammonium chloride solution. The solids formed were filtered and washed by cold water. The solids were dissolved in dichloromethane and washed by water. The organic phase was dried over MgSO$_4$ and concentrated under vacuum to yield 58.6 g (91%) of 4-(3-fluoro-benzyl)-5-oxo-7-[4-(thiophene-2-carbonyl)-piperazin-1-yl]-4,5-dihydro-thieno[3,2-b]pyridine-6-carboxylic acid ethyl ester. $^1$H-NMR (DMSO-d$_6$): δ 1.29 (t, J=7.2 Hz, 3H), 3.37 (m, 4H), 3.82 (m, 4H), 4.27 (q, J=7.2 Hz, 2H), 5.38 (s, 2H), 7.05-7.16 (m, 4H), 7.33 (d, J=5.6 Hz, 1H), 7.36 (m, 1H), 7.48 (dd, J=1.2, 3.6 Hz, 1H), 7.79 (dd, J=1.2, 5.2 Hz, 1H), 8.03 (d, J=5.6 Hz, 1H); EIMS m/z 526 (M+1). Anal. (C$_{26}$H$_{24}$FN$_3$O$_4$S$_2$) C, H, N.

Synthesis of 4-(3-fluoro-benzyl)-5-oxo-7-[4-(thiophene-2-carbonyl)-piperazin-1-yl]-4,5-dihydro-thieno[3,2-b]pyridine-6-carboxylic acid isopropyl ester (23)

This compound was prepared from 7-chloro-4-(3-fluoro-benzyl)-5-oxo-4,5-dihydro-thieno[3,2-b]pyridine-6-carboxylic acid isopropyl ester (18) by applying the same procedure as described for 4-(3-fluoro-benzyl)-5-oxo-7-[4-(thiophene-2-carbonyl)-piperazin-1-yl]-4,5-dihydro-thieno[3,2-b]pyridine-6-carboxylic acid ethyl ester (9). Yield (57%). $^1$H-NMR (DMSO-d$_6$) δ 1.29 (d, J=6.4 Hz, 6H), 3.37 (m, 4H), 3.81 (m, 4H), 5.10 (m, 1H), 5.38 (s, 2H), 7.04-7.16 (m, 4H), 7.32 (d, J=5.6 Hz, 1H), 7.37 (m, 1H), 7.47 (dd, J=1.2, 3.6 Hz, 1H), 7.79 (dd, J=1.2, 5.2 Hz, 1H), 8.02 (d, J=5.6 Hz, 1H); EIMS m/z 540 (M+1).

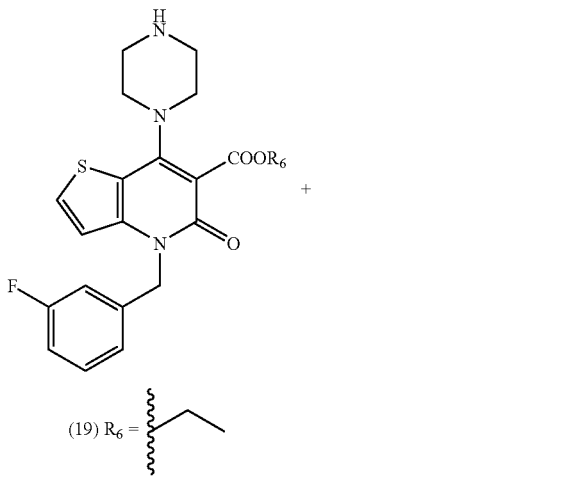

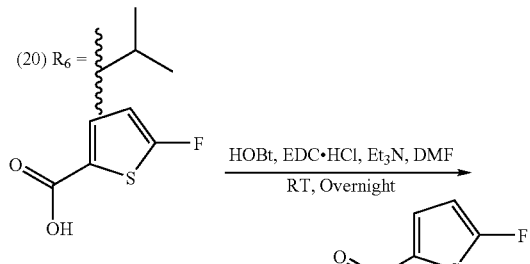

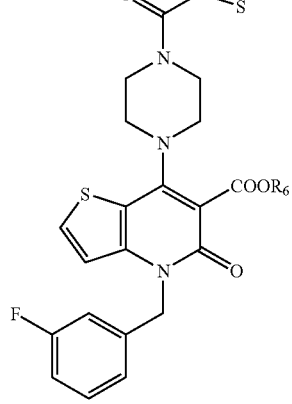

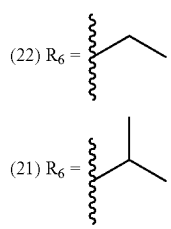

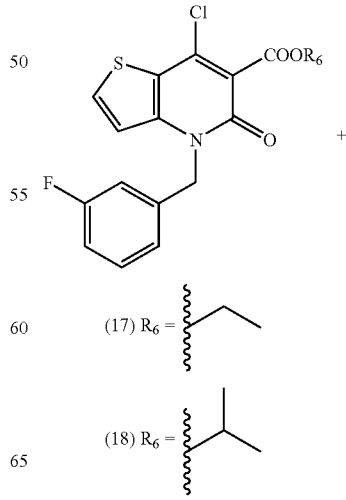

-continued

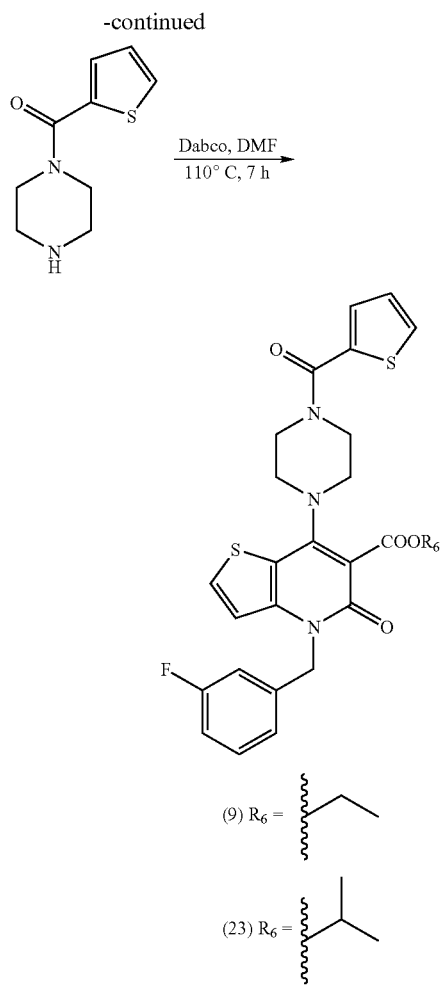

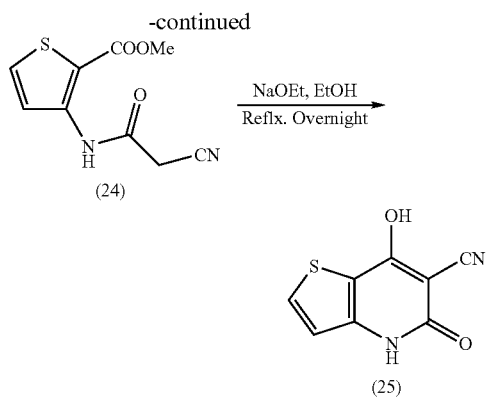

Synthesis of 7-hydroxy-5-oxo-4,5-dihydro-thieno[3,2-b]pyridine-6-carbonitrile (25)

Sodium ethoxide (3.10 g, 45.62 mmol) was added to a solution of 3-(2-cyano-acetylamino)-thiophene-2-carboxylic acid methyl ester (24) (3.10 g, 45.62 mmol) in anhydrous ethanol and refluxed overnight. The solution was cooled and excess solvent was distilled off. The residue was dissolved in water and acidified to pH 2 by cold diluted HCl solution. The solids formed were filtered, washed by cold water, and dried under vacuum at room temperature to yield 6.7 g (84%) of 7-hydroxy-5-oxo-4,5-dihydro-thieno[3,2-b]pyridine-6-carbonitrile as white solids. MP>300° C.; $^1$H NMR (400 MHz, DMSO-d6) δ 6.96 (d, J=5.2 Hz, 1H), 8.04 (d, J=5.2 Hz, 1H), 12.10 (s, 1H) ppm; MS m/z=193 amu(M$^+$+1).

Synthesis of 7-chloro-5-oxo-4,5-dihydro-thieno[3,2-b]pyridine-6-carbonitrile (26)

Triethylamine (11.78 mL, 84.54 mmol) was added to a solution of 7-hydroxy-5-oxo-4,5-dihydro-thieno[3,2-b]pyridine-6-carbonitrile (25) (6.5 g, 33.81 mmol) in neat phosphorous oxychloride at room temperature and heated at 70° C. for 1 h. The solution was cooled and excess phosphorus oxychloride was distilled under vacuum. The residue was suspended in water, and basified by solid NaHCO$_3$. The solids formed were filtered, washed by water, and dried. The crude product was suspended in dichloromethane, sonicated briefly, and filtered to yield 7-chloro-5-oxo-4,5-dihydro-thieno[3,2-b]pyrdine-6-carbonitrile (9) as white solids. Yield 5.3 g, (74%); MP 342° C.; $^1$H NMR (400 MHz, DMSO-d6) δ 7.11 (d, J=5.6 Hz, 1H), 8.29 (d, J=5.6 Hz, 1H) ppm; MS m/z=211 amu (M$^+$+1).

Synthesis of 3-(2-cyano-acetylamino)-thiophene-2-carboxylic acid methyl ester (24)

A solution of methyl-3-amino-thiophene-2-carboxylate (13 g, 82.70 mmol) in neat methyl cyanoacetate (40 mL) was heated at 210° C. for 10 h. The solution was cooled and excess methyl cyanoacetate was distilled off under vacuum. The residue was taken in methanol, sonicated briefly, and filtered. The solids were washed by cold methanol and dried to yield 9.3 g (50%) of 3-(2-cyano-acetylamino)-thiophene-2-carboxylic acid methyl ester as white solids. MP 146° C.; $^1$H NMR (400 MHz, DMSO-d6) δ 4.18 (s, 2H), 7.86 (d, J=5.2 Hz, 1H), 7.93 (d, J=5.2 Hz, 1H), 10.25 (s, 1H) ppm; MS m/z=225 amu (M$^+$+1).

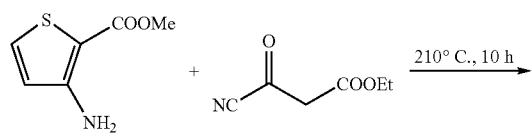

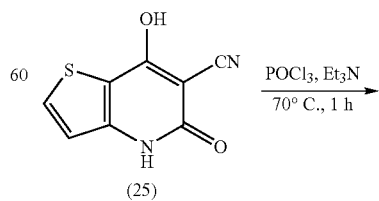

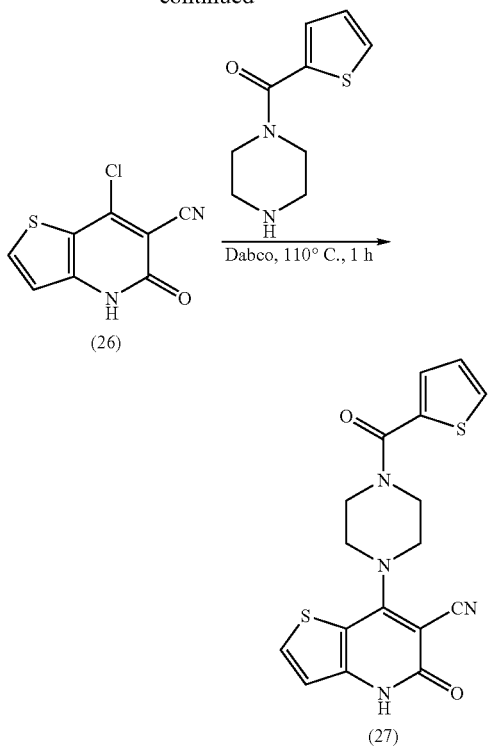

Synthesis of 5-oxo-7-[4-(thiophene-2-carbonyl)-piperazin-1-yl]-4,5-dihydro-thieno[3,2-b]pyridine-6-carbonitrile (27)

1,4-Diazabicyclo[2.2.2]octane (3.19 g, 28.48 mmol) was added to a solution of 7-chloro-5-oxo-4,5-dihydro-thieno[3,2-b]pyridine-6-carbonitrile (26) (3.0 g, 14.24 mmol) and piperazin-1-yl-thiophene-2-yl-methanone (3.07 g, 15.60 mmol) in dry DMA. The solution was heated at 110° C. for 1 h. The solution was cooled and poured into ice water. The solids formed were filtered, washed by water, and dried to yield 5-oxo-7-[4-(thiophene-2-carbonyl)-piperazin-1-yl]-4,5-dihydro-thieno[3,2-b]pyridine-6-carbonitrile (4.72 g, 89%) as white solids. MP 293° C.; $^1$H NMR (400 MHz, DMSO-d6) δ 3.89 (m, 8H), 7.02 (d, J=5.6 Hz, 1H), 7.20 (dd, J=3.6, 5.2 Hz, 1H), 7.54 (dd, J=1.2, 3.6 Hz, 1H), 7.84 (dd, J=1.2, 5.2 Hz, 1H), 8.16 (d, J=5.2 Hz, 1H) ppm; MS m/z=371 amu (M$^+$+1).

General Procedures for Alkylation at Nitrogen of Thienopyridinone Moiety

The compounds referred to as compounds (28) through (31) were prepared by applying either general procedure A or general procedure B.

General Procedure A

A solution of 5-oxo-7-[4-(thiophene-2-carbonyl)-piperazin-1-yl]-4,5-dihydro-thieno[3,2-b]pyridine-6-carbonitrile (27) (1.35 mmol) in dry DMF was added to a suspension of NaH (60% in mineral oil, 1.48 mmol) at room temperature. The solution was stirred at room temperature for 15 min under argon. A corresponding alkyl halide (1.48 mmol) was added to the solution and further stirred at room temperature until the reaction was completed (TLC and/or LC-MS controlled). The solution was poured into ice water and the solids formed were filtered, washed by cold water, and dried. The crude product was purified by flash chromatography eluting with 0-2% methanol in $CH_2Cl_2$ gradient to yield the compounds of preferred embodiments.

General Procedure B

A solution of 5-oxo-7-[4-(thiophene-2-carbonyl)-piperazin-1-yl]-4,5-dihydro-thieno[3,2-b]pyridine-6-carbonitrile (27) (1.35 mmol), a corresponding alkyl halide (2.70 mmol), and anhydrous potassium carbonate or cesium carbonate (6.75 mmol) in DMF was heated overnight at 90° C. The solution was cooled and the solvent was distilled under reduced pressure. The residue was suspended in water, sonicated briefly, and filtered. The crude product was purified by flash chromatography, eluting with 0-2% methanol in dichloromethane gradient.

Synthesis of 4-(4-fluoro-benzyl)-5-oxo-7-[4-(thiophene-2-carbonyl)-piperazin-1-yl]-4,5-dihydro-thieno[3,2-b]pyridine-6-carbonitrile (28)

The compound was prepared by using 4-fluorobenzyl bromide according to general procedure A to yield 260 mg (40%) white solids. MP 286° C.; $^1$H NMR (400 MHz, DMSO-d6) δ 3.88 (m, 8H), 5.36 (s, 2H), 7.13-7.18 (m, 3H), 7.30-7.35 (m, 3H), 7.51 (dd, J=1.2, 3.6 Hz, 1H), 7.81 (dd, J=1.2, 5.2 Hz, 1H), 8.21 (d, J=5.2 Hz, 1H) ppm; MS m/z=479 amu (M$^+$+1). Anal. ($C_{24}H_{19}FN_4O_2S_2$) C, H, N.

Synthesis of 4-(3-fluoro-benzyl)-5-oxo-7-[4-(thiophene-2-carbonyl)-piperazin-1-yl]-4,5-dihydro-thieno[3,2-b]pyrdine-6-carbonitrile (29)

The compound was prepared by using 3-fluorobenzyl bromide according to general procedure A to yield 372 mg (56%) white solids. MP 271° C.; $^1$H NMR (400 MHz, DMSO-d6) δ 3.89 (m, 8H), 5.39 (s, 2H), 7.05-7.13 (m, 3H), 7.16 (dd, J=3.6, 4.8 Hz, 1H), 7.31-7.37 (m, 2H), 7.51 (dd, J=1.2, 3.6 Hz, 1H), 7.81 (dd, J=1.2, 5.2 Hz, 1H), 8.21 (d, J=5.2 Hz, 1H) ppm; MS m/z=479 amu (M$^+$+1). Anal. ($C_{24}H_{19}FN_4O_2S_2$) C, H, N.

Synthesis of 5-oxo-4-(2-oxo-2-phenyl-ethyl)-7-[4-(thiophene-2-carbonyl)-piperazin-1-yl]-4,5-dihydro-thieno[3,2-b]pyridine-6-carbonitrile (30)

The compound was prepared by using 2-bromoacetophenone according to general procedure A to yield 362 mg (55%) white solids. MP 300° C.; $^1$H NMR (400 MHz, DMSO-d6) δ 3.92 (m, 8H), 5.78 (s, 2H), 7.17 (dd, J=3.6, 5.2 Hz, 1H), 7.36 (d, J=6.0 Hz, 1H), 7.52 (dd, J=1.2, 3.6 Hz, 1H), 7.61-7.63 (m, 2H), 7.75 (m, 1H), 7.81 (dd, J=1.2, 5.2 Hz, 1H), 8.09 (dd, J=1.6, 7.2 Hz, 2H), 8.21 (d, J=5.6 Hz, 1H) ppm; MS m/z=489 amu (M$^+$+1). Anal. ($C_{25}H_{20}N_4O_3S_2$) C, H, N.

Synthesis of 5-oxo-4-pyridine-3-yl-methyl-7-[4-(thiophene-2-carbonyl)-piperazin-1-yl]-4,5-dihydro-thieno[3,2-b]pyridine-6-carbonitrile (31)

The compound was prepared by using 3-bromomethyl pyridine hydrobromide according to general procedure B to yield 310 mg (49%) white solids. MP 247° C.; $^1$H NMR (400 MHz, DMSO-d6) δ 3.89 (m, 8H), 5.41 (s, 2H), 7.16 (dd, J=4.0, 5.2 Hz, 1H), 7.33 (dd, J=4.4, 7.6 Hz, 1H), 7.42 (d, J=5.6 Hz, 1H), 7.51 (d, J=3.6 Hz, 1H), 7.61 (d, J=8.0 Hz, 1H), 7.81 (d, J=5.2 Hz, 1H), 8.23 (d, J=5.6 Hz, 1H), 8.47

(dd, J=1.6, 5.6 Hz, 1H), 8.57 (d, J=2.0 Hz, 1H) ppm; MS m/z=462 amu (M++1). Anal. ($C_{23}H_{19}N_5O_2S_2$) C, H, N.

Synthesis of 3-methoxycarbonylmethylsulfanyl-propionic acid methyl ester (32)

Methyl acrylate (99.16 mL, 1.1 mol) was added slowly to a solution of methyl thioglycolate (91 mL, 1 mol) and piperidine (2 mL) while maintaining the temperature of reaction mixture at 50° C. The reaction mixture was stirred at 50° C. for 2 h. Excess methyl acrylate and piperidine were distilled off under high vacuum to yield 192 g (99%) of 3-methoxycarbonylmethylsulfanyl-propionic acid methyl ester as a colorless viscous oil. $^1$H NMR (400 MHz, $CDCl_3$) δ 2.63 (d, J=7.2 Hz, 2H), 2.89 (d, J=7.2 Hz, 2H), 3.24 (s, 2H), 3.68 (s, 3H), 3.72 (s, 3H) ppm.

Synthesis of 4-oxo-tetrahydro-thiophene-3-carboxylic acid methyl ester (33)

A solution of 3-methoxycarbonylmethylsulfanyl-propionic acid methyl ester (32) (58 g, 300 mmol) in dry THF (800 mL) was added slowly within 4 h to a refluxing solution of hexane washed NaH (60% in mineral oil, 13.24 g, 331 mmol) in THF. The solution was further refluxed for 5 h. The solution was cooled and the solvent was evaporated. The residue was taken in water, acidified to pH~1 by cold HCl solution, and extracted by $CH_2Cl_2$. The combined organic phase was dried over $MgSO_4$ and concentrated under vacuum to get a viscous residue. The residue was purified by flash chromatography eluting with hexane to yield 17 g (35%) of 4-oxo-tetrahydro-thiophene-3-carboxylic acid methyl ester as colorless viscous oil which solidified on keeping overnight under vacuum. MP 51° C.; $^1$H NMR (400 MHz, $CDCl_3$) δ 3.17-3.82 (m, 6.5 H), 10.94 (s, 0.5H) ppm. The isomeric mixture was used to next step without further purification.

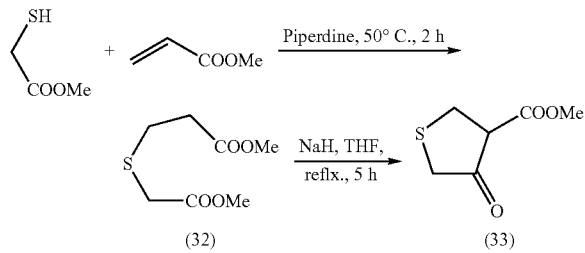

Synthesis of 4-hydroxyimino-tetrahydro-thiophene-3-carboxylic acid methyl ester (34)

A suspension of 4-oxo-tetrahydro-thiophene-3-carboxylic acid methyl ester (33) (16.96 g, 106 mmol), hydroxylamine hydrochloride (16.96 g, 244 mmol) and barium carbonate (48.16 g, 244 mmol) in methanol (800 mL) was refluxed overnight. The solution was cooled and filtered. The filtrate was concentrated in vacuo. The residue was suspended in water and extracted by ethyl acetate. The combined organic phase was dried over $MgSO_4$ and concentrated to yield 18.30 g (98%) of an isomeric mixture of 4-hydroxyimino-tetrahydro-thiophene-3-carboxylic acid methyl ester as a viscous oil. $^1$H NMR (400 MHz, $CDCl_3$) δ 3.14-4.11 (m, 7H), 8.17 (m, 1H) ppm. The isomeric mixture was used in the following step without further purification.

Synthesis of 4-amino-thiophene-3-carboxylic acid methyl ester (35)

HCl (1M solution in ether, 125 mL) was added slowly to a solution of 4-hydroxyimino-tetrahydro-thiophene-3-carboxylic acid methyl ester (34) (18.30 g, 104 mmol) in dry ether (200 mL) and dry methanol (50 mL) stirred at room temperature. The solution was further stirred at room temperature under argon for 24 h. The solids formed were filtered, washed by cold ether, and dried to yield 18.20 g (91%) of 4-amino-thiophene-3-carboxylic acid methyl ester as the hydrochloride salt. MP 198° C.; $^1$H NMR (400 MHz, DMSO-d6) δ 3.86 (s, 3H), 7.22 (d, J=2.4 Hz, 1H), 8.37 (d, J=3.2 Hz, 1H) ppm; MS m/z=158 amu (M++1).

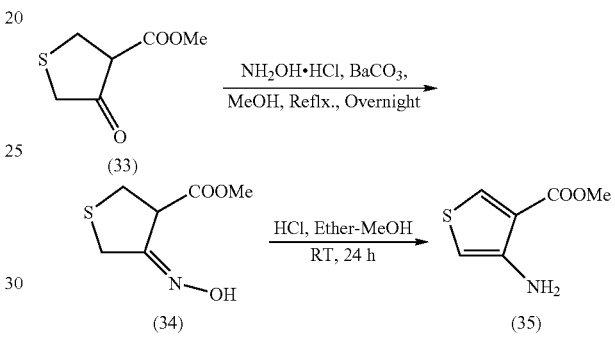

Synthesis of 4-(2-ethoxycarbonyl-acetylamino)-thiophene-3-carboxylic acid methyl ester (36)

Pyridine (6.45 mL, 79.79 mmol) was added to a stirred suspension of 4-amino-thiophene-3-carboxylic acid methyl ester hydrochloride (35) (7 g, 36.27 mmol) in dry toluene at room temperature. The solution was further stirred at room temperature for 5 min and then cooled to −10° C. Ethylmalonyl chloride (4.59 mL, 36.27 mmol) was added to this solution and further stirred at −10° C. for 1 h. The solution was allowed to come to room temperature and poured into ice water. The product was extracted by ethyl acetate. The combined organic phase was sequentially washed by diluted HCl solution, saturated $NaHCO_3$ solution, water, and brine. The organic phase was dried over $MgSO_4$ and concentrated to yield 8.57 g (63%) of 4-(2-ethoxycarbonyl-acetylamino)-thiophene-3-carboxylic acid methyl ester as a yellow viscous oil. $^1$H NMR (400 MHz, DMSO-d6) δ 1.19 (t, J=7.2 Hz, 3H), 3.63 (s, 2H), 3.86 (s, 3H), 4.15 (q, J=7.2 Hz, 2H), 7.96 (d, J=3.6 Hz, 1H), 8.37 (d, J=3.6 Hz, 1H), 10.37 (s, 1H) ppm; MS m/z=240 amu (M++1).

Synthesis of 7-hydroxy-5-oxo-4,5-dihydro-2-thia-4-aza-indene-6-carboxylic acid ethyl ester (37)

Sodium ethoxide (4.75 g, 66.34 mmol) was added to a solution of 4-(2-ethoxycarbonyl-acetylamino)-thiophene-3-carboxylic acid methyl ester (19) (8.57 g, 31.59 mmol) in anhydrous ethanol and refluxed overnight. The solution was cooled and excess solvent was distilled off The residue was dissolved in water and acidified by cold diluted HCl solution. The solids formed were filtered, washed by water and dried under vacuum at room temperature to get 4.3 g (57%)

of 7-hydroxy-5-oxo-4,5-dihydro-2-thia-4-aza-indene-6-carboxylic acid ethyl ester as white solid. MP 193° C.; $^1$H NMR (400 MHz, DMSO-d6) δ 1.27 (t, J=7.2 Hz, 3H), 4.28 (q, J=7.2 Hz, 2H), 6.83 (d, J=3.2 Hz, 1H), 8.24 (d, J=3.6 Hz, 1H), 11.10 (s, 1H), 12.90 (s, 1H) ppm; MS m/z=240 amu (M$^+$+1).

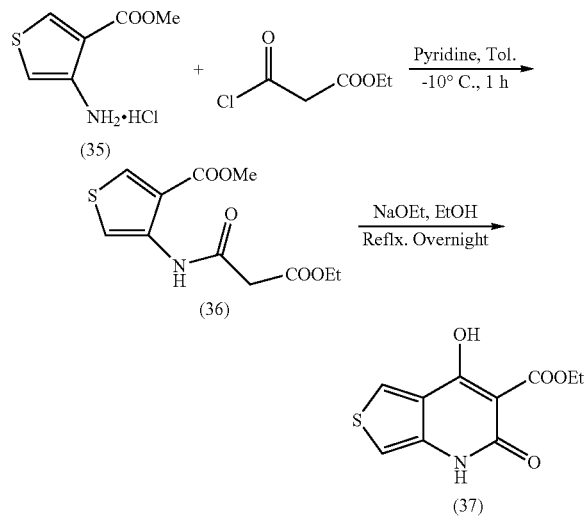

Synthesis of 5,7-dichloro-2-thia-4-aza-indene-6-carboxylic acid ethyl ester (38)

A solution of 7-hydroxy-5-oxo-4,5-dihydro-2-thia-4-aza-indene-6-carboxylic acid ethyl ester (37) (3.9 g, 16.30 mmol) in neat phosphorous oxychloride (40 mL) was heated at 90° C. for 4 h. The solution was cooled and excess phosphorus oxychloride was distilled under vacuum. The residue was suspended in water, sonicated briefly, and filtered. The solids were dissolved in CH$_2$Cl$_2$ and washed sequentially by saturated NaHCO$_3$ solution, water, and brine. The organic phase was dried over MgSO$_4$ and concentrated under vacuum The crude product was purified by flash chromatography, eluting with CH$_2$Cl$_2$, to yield 5,7-dichloro-2-thia-4-aza-indene-6-carboxylic acid ethyl ester as white solids. Yield 2.1 g (46%); MP 79° C.; $^1$H NMR (400 MHz, DMSO-d6) δ 1.35 (t, J=7.2 Hz, 3H), 4.46 (q, J=7.2 Hz, 2H), 8.47 (d, J=3.6 Hz, 1H), 8.53 (d, J=3.2 Hz, 1H) ppm; MS m/z=276 amu (M).

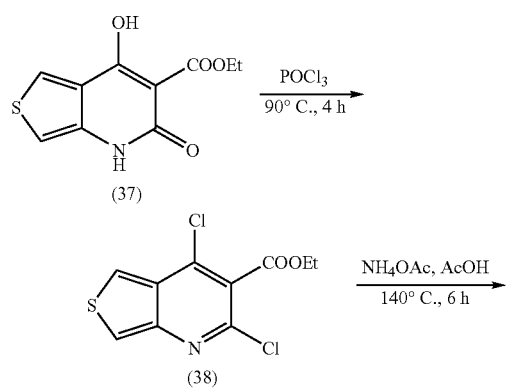

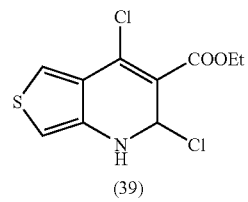

Synthesis of 7-chloro-5-oxo-4,5-dihydro-2-thia-4-aza-indene-6-carboxylic acid ethyl ester (39)

Ammonium acetate (0.644 mg, 8.3 mmol) was added to a stirred solution of 5,7-dichloro-2-thia-4-aza-indene-6-carboxylic acid ethyl ester (38) (2.1 g, 7.6 mmol) in glacial acetic acid at room temperature. The solution was heated at 140° C. for 6 h. The hot solution was poured over ice. The solids formed were filtered, washed by water, and dried to yield 1.9 g (97%) of 7-chloro-5-oxo-4,5-dihydro-2-thia-4-aza-indene-6-carboxylic acid ethyl ester as white solids. MP 157° C.; $^1$H NMR (400 MHz, DMSO-d6) δ 1.28 (t, J=7.2 Hz, 3H), 4.32 (q, J=7.2 Hz, 2H), 7.06 (d, J=3.6 Hz, 1H), 8.20 (d, J=3.2 Hz, 1H) ppm; MS m/z=258 amu (M$^+$+1).

Synthesis of 5-oxo-7-[4-(thiophene-2-carbonyl)-piperazin-1-yl]-4,5-dihydro-2-thia-4-aza-indene-6-carboxylic acid ethyl ester (40)

1,4-Diazabicyclo[2.2.2]octane (2.07 g, 10.16 mmol) was added to a solution of 7-chloro-5-oxo-4,5-dihydro-2-thia-4-aza-indene-6-carboxylic acid ethyl ester (39) (2.4 g, 9.24 mmol) and piperazin-1-yl-thiophene-2-yl-methanone (1.99 g, 10.16 mmol) in dry DMA. The solution was heated at 110° C. for 3 h. The solution was cooled and the solvent was distilled. The residue was suspended in water, sonicated briefly, and filtered. The solids were washed by excess water and dried to yield 5-oxo-7-[4-(thiophene-2-carbonyl)-piperazin-1-yl]-4,5-dihydro-2-thia-4-aza-indene-6-carboxylic acid ethyl ester (3.47 g, 90%) as white solids. MP 282° C.; $^1$H NMR (400 MHz, DMSO-d6) δ 1.27 (t, J=7.2 Hz, 3H), 3.27 (m, 4H), 3.77 (m, 4H), 4.24 (q, J=7.2 Hz, 2H), 6.86 (d, J=3.6 Hz, 1H), 7.15 (dd, J=3.6, 5.2 Hz, 1H), 7.46 (dd, J=1.2, 3.6 Hz, 1H), 7.80 (dd, J=1.2, 4.8 Hz, 1H), 8.02 (d, J=3.2 Hz, 1H), 11.30 (s, 1H) ppm; MS m/z=418 amu (M$^+$+1).

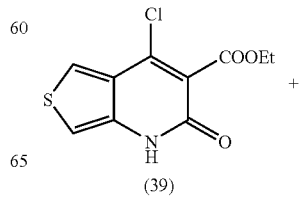

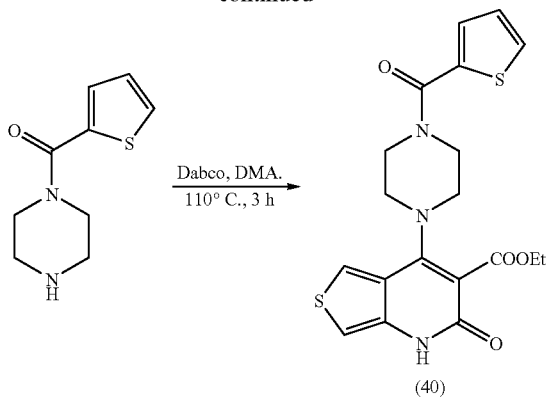

(40)

Synthesis of 5-oxo-4-(2-oxo-2-phenyl-ethyl)-7-[4-(thiophene-2-carbonyl)-piperazin-1-yl]-4,5-dihydro-2-thia-4-aza-indene-6-carboxylic acid ethyl ester (41)

The compound was prepared from 5-oxo-7-[4-(thiophene-2-carbonyl)-piperazin-1-yl]-4,5-dihydro-2-thia-4-aza-indene-6-carboxylic acid ethyl ester (40) and 2-bromoacetophenone by applying general procedure A. Yield 66%; $^1$H NMR (400 MHz, DMSO-d6) δ 1.25 (t, J=7.2 Hz, 3H), 3.34 (m, 4H), 3.86 (m, 4H), 4.24 (q, J=7.2 Hz, 2H), 5.58 (s, 2H), 7.15 (dd, J=3.6, 4.6 Hz, 1H), 7.24 (d, J=3.2 Hz, 1H), 7.48 (dd, J=1.2, 3.6 Hz, 1H), 7.60 (m, 2H), 7.71 (m, 1H), 7.80 (dd, J=1.2, 4.8 Hz, 1H), 8.09 (m, 2H), 8.16 (d, J=3.2 Hz, 1H) ppm; MS m/z=535 amu (M$^+$+1). Anal. ($C_{27}H_{25}N_3O_5S_2$) C, H, N.

Synthesis of 4-(4-fluoro-benzyl)-5-oxo-7-[4-(thiophene-2-carbonyl)-piperazin-1-yl]-4,5-dihydro-2-thia-4-aza-indene-6-carboxylic acid ethyl ester (42)

The compound was prepared from 5-oxo-7-[4-(thiophene-2-carbonyl)-piperazin-1-yl]-4,5-dihydro-2-thia-4-aza-indene-6-carboxylic acid ethyl ester (40) and 4-fluorobenzylbromide by applying general procedure A. Yield 54%; MP 227° C. $^1$H NMR (400 MHz, DMSO-d6) δ 1.27 (t, J=7.2 Hz, 3H), 3.30 (m, 4H), 3.83 (m, 4H), 4.27 (q, J=7.2 Hz, 2H), 5.18 (s, 2H), 7.14-7.17 (m, 3H), 7.20 (d, J=3.2 Hz, 1H), 7.33 (m, 2H), 7.46 (dd, J=1.2, 4.8 Hz, 1H), 7.80 (dd, J=1.2, 4.8 Hz, 1H), 8.13 (d, J=3.2 Hz, 1H) ppm; MS m/z=526 amu (M$^+$+1). Anal. ($C_{26}H_{24}FN_3O_4S_2$) C, H, N.

Synthesis of 4-(4-methoxycarbonyl-benzyl)-5-oxo-7-[4-(thiophene-2-carbonyl)-piperazin-1-yl]-4,5-dihydro-2-thia-4-aza-indene-6-carboxylic acid ethyl ester (43)

The compound was prepared from 5-oxo-7-[4-(thiophene-2-carbonyl)-piperazin-1-yl]-4,5-dihydro-2-thia-4-aza-indene-6-carboxylic acid ethyl ester (40) and methyl-4-bromomethylbenzoate by applying general procedure A. Yield 51%; $^1$H NMR (400 MHz, DMSO-d6) δ 1.25 (t, J=7.2 Hz, 3H), 3.30 (m, 4H), 3.82 (m, 7H), 4.27 (q, J=7.2 Hz, 2H), 5.28 (s, 2H), 7.12 (d, J=3.2 Hz, 1H), 7.16 (dd, J=5.2, 3.2 Hz, 1H), 7.37 (m, 2H), 7.47 (dd, J=1.2, 3.6 Hz, 1H), 7.79 (dd, J=1.2, 5.2 Hz, 1H), 7.91 (m, 2H), 8.13 (d, J=3.2 Hz, 1H) ppm; MS m/z=565 amu (M$^+$+1). Anal. ($C_{28}H_{27}N_3O_6S_2$) C, H, N.

Synthesis of 7-hydroxy-5-oxo-4,5-dihydro-2-thia-4-aza-indene-6-carboxylic acid cyclohexylamide (44)

Cyclohexylamine (4.6 mL, 40.12 mmol) was added to a solution of 7-hydroxy-5-oxo-4,5-dihydro-2-thia-4-aza-indene-6-carboxylic acid ethyl ester (39) (3.2 g, 82.70 mmol) in toluene and heated at 130° C. for 4 h. The solution was cooled and excess solvent was distilled off under vacuum. The residue was taken in $CH_2Cl_2$, sonicated briefly, and filtered to yield 3.5 g (89%) of 7-hydroxy-5-oxo-4,5-dihydro-2-thia-4-aza-indene-6-carboxylic acid cyclohexylamide as white solids. MP 244° C.; $^1$H NMR (400 MHz, DMSO-d6) δ 1.26-1.41 (m, 5H), 1.53 (m, 1H), 1.65 (m, 2H), 1.86 (m, 2H), 3.81 (m, 1H), 6.95 (s, 1H), 8.25 (s, 1H) ppm; MS m/z=293 amu (M$^+$+1).

Synthesis of 5,7-dichloro-2-thia-4-aza-indene-6-carbonitrile (45)

A solution of 7-hydroxy-5-oxo-4,5-dihydro-2-thia-4-aza-indene-6-carboxylic acid cyclohexylamide (44) (3.5 g, 11.97 mmol) in neat phosphorous oxychloride at room temperature was heated at 90° C. for 3 h. The solution was cooled and excess phosphorus oxychloride was distilled under vacuum. The residue was suspended in water, and basified by solid $NaHCO_3$. The solids formed were filtered washed by water and dried to yield 5,7-dichloro-2-thia-4-aza-indene-6-carbonitrile as white solids. Yield 2.5 g (91%); MP 228° C.; $^1$H NMR (400 MHz, DMSO-d6) δ 8.50 (m, 1H), 8.75 (m, 1H) ppm; MS m/z=229 amu (M$^+$).

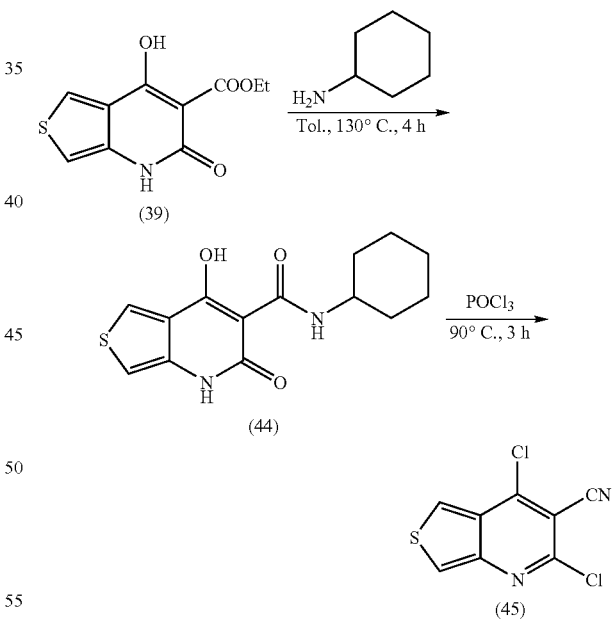

Synthesis of 7-chloro-4,5-dihydro-5-oxo-2-thia-5-aza-indene-6-carbonitrile (46)

Ammonium acetate (0.92 g, 12.0 mmol) was added to a stirred solution of 5,7-dichloro-2-thia-4-aza-indene-6-carbonitrile (45) (2.5 g, 10.91 mmol) in glacial acetic acid at room temperature. The solution was heated at 140° C. for 2 h. The hot solution was poured over ice. The solids formed were filtered, washed by water, and dried to yield 2.0 g (87%) of 7-chloro-4,5-dihydro-5-oxo-2-thia-5-aza-indene-6-carbonitrile as white solids. MP 310° C.; $^1$H NMR (400 MHz, DMSO-d6) δ 7.11 (d, J=3.2 Hz, 1H), 8.45 (d, J=3.2 Hz, 1H) ppm; MS m/z=211 amu (M$^+$).

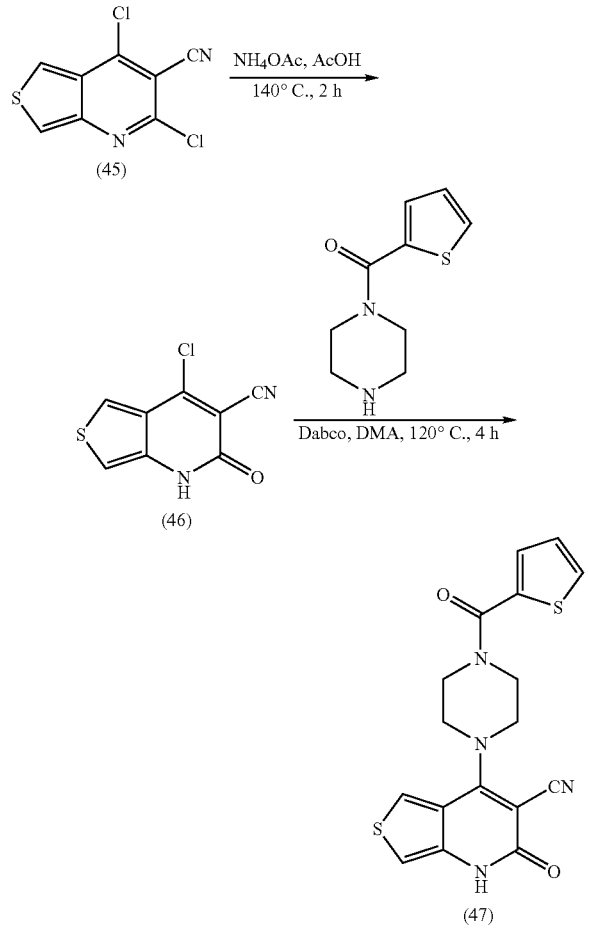

Synthesis of 5-oxo-7-[4-(thiophene-2-carbonyl)-piperazin-1-yl]-4,5-dihydro-2-thia-4-aza-indene-6-carbonitrile (47)

1,4-Diazabicyclo[2.2.2]octane (2.13 g, 19.0 mmol) was added to a solution of 7-chloro-4,5-dihydro-5-oxo-2-thia-5-aza-indene-6-carbonitrile (46) (2.0 g, 9.5 mmol) and piperazin-1-yl-thiophene-2-yl-methanone (2.23 g, 11.4 mmol) in dry DMA. The solution was heated at 110° C. for 4 h. The solution was cooled and excess solvent was distilled under vacuum The residue was suspended in water, sonicated briefly, filtered, washed by water, and dried to yield 5-oxo-7-[4-(thiophene-2-carbonyl)-piperazin-1-yl]-4,5-dihydro-2-thia-4-aza-indene-6-carbonitrile (3.2 g, 91%) as white solids. MP 263° C.; $^1$H NMR (400 MHz, DMSO-d6) δ 3.89 (m, 8H), 6.90 (d, J=3.2 Hz, 1H), 7.17 (dd, J=3.6, 5.2 Hz, 1H), 7.50 (dd, J=1.2, 3.6 Hz, 1H), 7.81 (dd, J=1.2, 5.2 Hz, 1H), 8.28 (d, J=3.2 Hz, 1H) ppm; MS m/z=371 amu (M$^+$+1).

The compounds referred to as compounds (48) through (51) were prepared from 5-oxo-7-[4-(thiophene-2-carbonyl)-piperazin-1-yl]-4,5-dihydro-2-thia-4-aza-indene-6-carbonitrile (47) by applying either general procedure A or general procedure B described above.

Synthesis of 5-oxo-4-(2-oxo-2-phenyl-ethyl)-7-[4-(thiophene-2-carbonyl)-piperazin-1-yl]-4,5-dihydro-2-thia-4-aza-indene-6-carbonitrile (48)

The compound was prepared by using 2-bromoacetophenone according to general procedure A. Yield 56%. MP 308° C.; $^1$H NMR (400 MHz, DMSO-d6) δ 3.95 (m, 8H), 5.60 (s, 2H), 7.17 (dd, J=3.6, 4.8 Hz, 1H), 7.27 (d, J=3.2 Hz, 1H), 7.52 (dd, J=1.2, 3.6 Hz, 1H), 7.61-7.63 (m, 2H), 7.73 (m, 1H), 7.82 (dd, J=1.2, 4.8 Hz, 1H), 8.09 (dd, J=1.2, 7.2 Hz, 2H), 8.43 (d, J=3.2 Hz, 1H) ppm; MS m/z=489 amu (M$^+$+1). Anal. ($C_{25}H_{20}N_4O_3S_2$) C, H, N.

Synthesis of 4-(4-fluoro-benzyl)-5-oxo-7-[4-(thiophene-2-carbonyl)-piperazin-1-yl]-4,5-dihydro-2-thia-4-aza-indene-6-carbonitrile (49)

The compound was prepared by using 4-fluorobenzyl bromide according to general procedure A. Yield 40%; MP 238° C.; $^1$H NMR (400 MHz, DMSO-d6) δ 3.92 (m, 8H), 5.19 (s, 2H), 7.15-7.19 (m, 4H), 7.30-7.35 (m, 2H), 7.50 (dd, J=1.2, 3.6 Hz, 1H), 7.80 (dd, J=1.2, 5.2 Hz, 1H), 8.40 (d, J=3.2Hz, 1H) ppm; MS m/z=479 amu (M$^+$+1). Anal. ($C_{24}H_{19}FN_4O_2S_2$) C, H, N.

Synthesis of 4-{6-cyano-5-oxo-7-[4-(thiophene-2-carbonyl)-piperazin-1-yl]-5H-2-thia-4-aza-indene-4-ylmethyl}-benzoic acid methyl ester (50)

The compound was prepared by using methyl 4-bromomethyl benzoate according to general procedure A. Yield 56%; MP 263° C.; $^1$H NMR (400 MHz, DMSO-d6) δ 3.82 (s, 3H), 3.93 (m, 8H), 5.29 (s, 2H), 7.12 (d, J=3.2 Hz, 1H), 7.17 (dd, J=3.6, 4.8 Hz, 1H), 7.38 (d, J=8.0 Hz, 1H), 7.51 (dd, J=1.2, 3.6 Hz, 1H), 7.80 (dd, J=1.2, 5.2 Hz, 1H), 7.92 (d, J=8.0 Hz, 1H), 8.40 (d, J=2.8 Hz, 1H) ppm; MS m/z=519 amu (M$^+$+1). Anal. ($C_{26}H_{22}N_4O_4S_2$) C, H, N.

Synthesis of 5-oxo-4-pyridine-3-yl-methyl-7-[4-(thiophene-2-carbonyl)-piperazin-1-yl]-4,5-dihydro-2-thia-4-aza-indene-6-carbonitrile (51)

The compound was prepared by using 3-chloromethyl pyridine hydrochloride according to general procedure B. Yield 49%; MP 263° C.; $^1$H NMR (400 MHz, DMSO-d6) δ 3.92 (m, 8H), 5.25 (s, 2H), 7.17 (dd, J=4.0, 5.2 Hz, 1H), 7.28 (d, J=3.2 Hz, 1H), 7.33 (dd, J=4.8, 8.0 Hz, 1H), 7.50 (d, J=1.2 Hz, 1H), 7.66 (d, J=8.0 Hz, 1H), 7.80 (d, J=5.2 Hz, 1H), 8.40 (d, J=3.2 Hz, 1H), 8.45 (d, J=4.8 Hz, 1H), 8.58 (s, 1H) ppm; MS m/z=462 amu (M$^+$+1). Anal. ($C_{23}H_{19}N_5O_2S_2$) C, H, N.

Synthesis of 5-oxo-4-pyridine-3-yl-7-[4-(thiophene-2-carbonyl)-piperazin-1-yl]-4,5-dihydro-2-thia-4-aza-indene-6-carbonitrile (52)

Cu(OAc)$_2$ (363 mg, 2 mmol), pyridine-3-boronic acid (614 mg, 5 mmol), and triethylamine (560 μL, 4 mmol) were added to a solution of 5-oxo-7-[4-(thiophene-2-carbonyl)-piperazin-1-yl]-4,5-dihydro-2-thia-4-aza-indene-6-carbonitrile (47) (370 mg, 1 mmol) in wet DMF (DMF:H$_2$O::9:1) stirred at room temperature. The solution was further stirred at room temperature for 24 h. The solution was passed through a bed of celite and the solvent was evaporated. The residue was suspended in water and extracted by $CH_2Cl_2$. The combined organic phase was partitioned with 10% aqueous HCl solution. The aqueous phase was separated and the pH was adjusted to 5 by 4 N NaOH solution. Then, a saturated solution of $NaHCO_3$ was added until the pH reached to 8. The solids formed were filtered, washed by water, and dried under vacuum at 70° C. to get 5-oxo-4-pyridine-3-yl-7-[4-(thiophene-2-carbonyl)-piperazin-1-yl]-4,5-dihydro-2-thia-4-aza-indene-6-carbonitrile as white solids. Yield 243 mg (54%); MP 282° C.; $^1$H NMR (400 MHz, DMSO-d6) δ 3.99 (m, 8H), 6.42 (d, J=2.8 Hz, 1H), 7.18 (dd, J=4.0, 4.8 Hz, 1H), 7.52 (d, J=2.8 Hz, 1H), 7.64 (dd, J=4.8, 8.0 Hz, 1H), 7.81 (d, J=4.8 Hz, 1H), 7.88 (dm, 1H), 8.47 (d, J=3.2 Hz, 1H), 8.58 (d, J=2.0 Hz, 1H), 8.71 (d, J=3.6 Hz, 1H) ppm; MS m/z=448 amu ($M^+$+1). Anal. ($C_{22}H_{17}N_5O_2S_2$) N.

Synthesis of methyl 3-(4-methoxybenzylamino)-thiophene-2-carboxylic acid methyl ester (53)

4-Methoxybenzyl chloride (22.8 mL, 167.42 mmol) was added to a solution of methyl-3-amino-thiophene-2-carboxylate (17.55 g, 111 mmol) in dry $CH_2Cl_2$ (20 mL). The solution was mixed well. Excess $CH_2Cl_2$ was evaporated and the mixture was heated overnight at 85° C. under vacuum (3 torr). The mixture was cooled to room temperature. Hexane was added to the mixture, which was refluxed for 30 min, and cooled to 0° C. The solids formed were filtered, washed by hexane, and dried to yield 28.19 g (91%) of 3-(4-methoxybenzylamino)-thiophene-2-carboxylic acid methyl ester as red solids. $^1$H NMR (400 MHz, DMSO-d6) δ 3.71 (s, 6H), 4.42 (s, 2H), 6.77 (d, J=5.6 Hz, 1H), 6.88 (d, J=8.8 Hz, 2H), 7.25 (d, J=8.8 Hz, 2H), 7.63 (d, J=5.6 Hz, 1H), ppm; MS m/z=278 amu ($M^+$+1).

Synthesis of 7-hydroxy-4-(4-methoxybenzyl)-5-oxo-4,5-dihydro-thieno[3 2-b]pyridine-6-carboxylic acid ethyl ester (54)

Solid NaH (60% in min. oil, 4.62 g, 135 mmol) was added in portions to a stirred solution of 3-(4-methoxybenzylamino)-thiophene-2-carboxylic acid methyl ester (53) (26.69 g, 96 mmol) in dry DMF. The solution was stirred for 10 min. at room temperature and cooled to 0° C. Ethyl malonyl chloride was added slowly and the solution was further stirred at room temperature for 15 min. Sodium ethoxide (13.1 g, 192 mmol) was added to the solution and the solution was heated to 110° C. for 2 h. The solution was cooled and excess solvent was distilled off The residue was dissolved in a mixture of water (350 mL) and 4 M NaOH (50 mL), and the insoluble impurities were filtered off The filtrate was washed by diisopropyl ether and then acidified to pH 4 by cold diluted HCl solution. The solids formed were filtered, washed by water, and dried under vacuum at room temperature to yield 27 g (79%) of 7-hydroxy-4-(4-methoxybenzyl)-5-oxo-4,5-dihydro-thieno[3,2-b]pyridine-6-carboxylic acid ethyl ester as off-white solids. $^1$H NMR (400 MHz, DMSO-d6) δ 1.30 (t, J=7.2 Hz, 3H), 3.70 (s, 3H), 4.32 (q, J=7.2 Hz, 2H), 5.27 (s, 2H), 6.86 (d, J=8.8 Hz, 2H), 7.21 (d, J=8.8 Hz, 2H), 7.34 (d, J=5.6 Hz, 1H), 8.14 (d, J=5.6 Hz, 1H), 13.31 (br, 1H) ppm; MS m/z=360 amu ($M^+$+1).

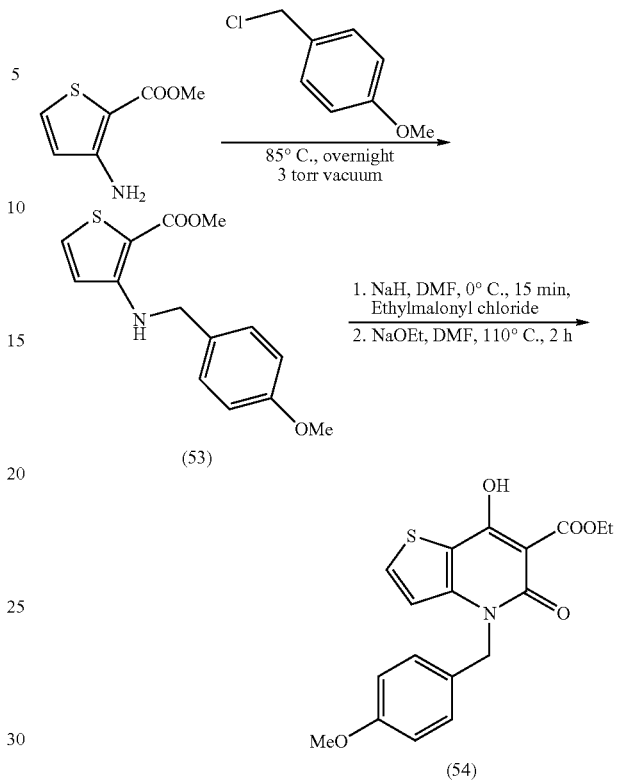

Synthesis of 7-chloro-4-(4-methoxybenzyl)-5-oxo-4,5-dihydro-thieno[3,2-b]pyridine-6-carboxylic acid ethyl ester (55)

Oxalyl chloride (4.8 mL, 55 mmol) was added to a solution of 7-hydroxy-4-(4-methoxybenzyl)-5-oxo-4,5-dihydro-thieno[3,2-b]pyridine-6-carboxylic acid ethyl ester (54) (9.87 g, 27 mmol) in dry $CH_2Cl_2$ at 0° C. After adding anhydrous DMF (0.5 mL), the solution was allowed to come at room temperature and was further stirred at room temperature for 24 h. Excess solvent was evaporated to yield 7-chloro-4-(4-methoxybenzyl)-5-oxo-4,5-dihydro-thieno[3,2-b]pyridine-6-carboxylic acid ethyl ester as off white solids. Yield 85%; $^1$H NMR (400 MHz, DMSO-d6) δ 1.30 (t, J=7.2 Hz, 3H), 3.70 (s, 3H), 5.36 (s, 2H), 6.88 (d, J=8.4 Hz, 2H), 7.24 (d, J=8.4 Hz, 2H), 7.53 (d, J=5.6 Hz, 1H), 8.20 (d, J=5.6 Hz, 1H ppm; MS m/z=378 amu ($M^+$+H).

Synthesis of 7-chloro-5-oxo-4,5-dihydro-thieno[3,2-b]pyridine-6-carboxylic acid ethyl ester (4)

A solution of 7-chloro-4-(4-methoxybenzyl)-5-oxo-4,5-dihydro-thieno[3,2-b]pyridine-6-carboxylic acid ethyl ester (55) (10.40 g, 27.5 mmol) in neat TFA was heated at 70° C. under argon for 36 h. The solution was cooled and poured into ice water. The solids formed were filtered, washed by water, and dried to yield 7.08 g (99%) of 7-chloro-5-oxo-4,5-dihydro-thieno[3,2-b]pyridine-6-carboxylic acid ethyl ester as white solids. MP 206° C.; $^1$H NMR (400 MHz, DMSO-d6) δ 1.28 (t, J=7.2 Hz, 3H), 4.29 (q, J=7.2 Hz, 2H), 7.10 (d, J=5.2 Hz, 1H), 8.13 (d, J=5.2 Hz, 1H) ppm; MS m/z=240 amu ($M^+$+1).

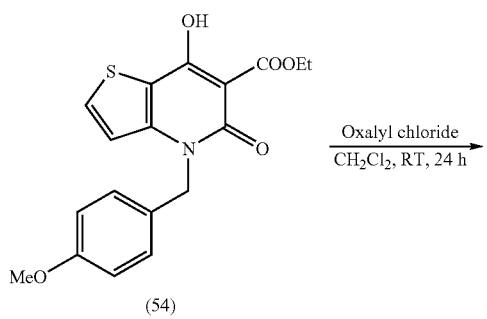

(54)

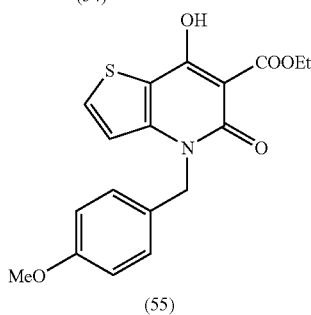

(55)

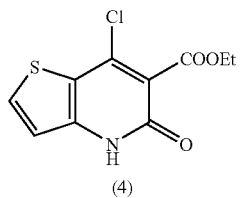

(4)

Synthesis of 1H-thieno[2,3-d][1,3]oxazine-2,4-dione (56)

Methyl 2-amino-thiophene-3-carboxylate (5 g, 31.72 mmol) was added to a solution of potassium hydroxide (3.55 g, 63.45 mmol) in 10 mL water. The solution was heated at 90° C. until to get a clear solution. The solution was then cooled to 0° C. and trichloromethyl chloroformate (5.74 mL, 47.57 mmol) was added slowly. The solution was allowed to come to room temperature and further stirred for 30 min. The precipitated solid was collected by vacuum filtration to yield 4.7 g (88%) of 1H-thieno[2,3-d][1,3]oxazine-2,4-dione. MP 233° C. $^1$H-NMR (DMSO-d$_6$) δ 7.15 (d, J=6.0 Hz, 1H), 7.19 (d, J=6.0 Hz, 1H) ppm.

Synthesis of 5-methyl-1H-thieno[2,3-d][1,3]oxazine-2,4-dione (57)

Potassium hydroxide (14.77 g, 0.26 mol) was dissolved in 500 mL water. To this solution was added ethyl 2-amino-4-methyl-thiophene-3-carboxylate (24.38 g, 0.13 mol). The solution was heated at 100° C. for 16 hours. The solution was then cooled to 0° C. and trichloromethyl chloroformate (23.8 mL, 0.20 mol) was added slowly. The solution was allowed to come to room temperature and further stirred for 5 hours. The precipitated solid was collected by vacuum filtration to yield 16.0 g (66%) of 5-methyl-1H-thieno[2,3-d][1,3]oxazine-2,4-dione. MP 220° C. $^1$H-NMR (DMSO-d$_6$) δ 2.30 (d, J=1.2 Hz, 3H), 6.78 (d, J=1.2 Hz, 1H), 12.55 (b, 1H) ppm; EIMS m/z 184 (M+1).

Synthesis of 1-benzyl-1H-thieno[2,3-d][1,3]oxazine-2,4-dione (58)

NaH (60% dispersion in mineral oil, 1.0 g, 0.025 mol) was added to a solution of 1H-thieno[2,3-d][1,3]oxazine-2,4-dione (56) (3.53 g, 0.021 mol) in anhydrous DMF stirred at 0° C. under argon. The solution was stirred for 15 minutes before adding benzyl bromide (2.97 mL, 0.025 mol). The solution was allowed to come to room temperature and further stirred for 12 hours. The solution was poured into ice water and the precipitated solid was collected by vacuum filtration to yield 4.0 g (74%) of 1-benzyl-1H-thieno[2,3-d][1,3]oxazine-2,4-dione. $^1$H-NMR (DMSO-d$_6$) δ 5.13 (s, 2H), 7.22 (d, J=5.6 Hz, 1H), 7.28 (d, J=5.6 Hz, 1H), 7.30-7.45 (m, 5H) ppm; EIMS m/z 260 (M+1).

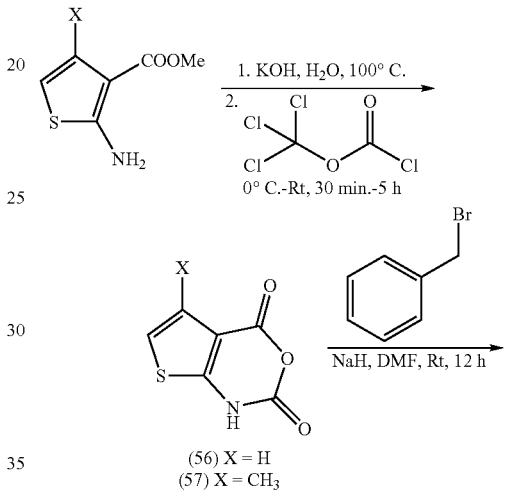

(56) X = H
(57) X = CH$_3$

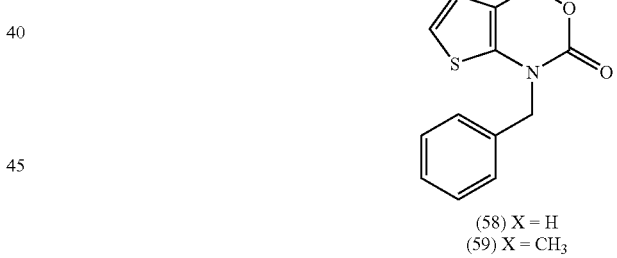

(58) X = H
(59) X = CH$_3$

Synthesis of 1-benzyl-5-methyl-1H-thieno[2,3-d][1,3]oxazine-2,4-dione (59)

This compound was prepared from 5-methyl-1H-thieno[2,3-d][1,3]oxazine-2,4-dione (57) by applying the same method as described for the preparation of 1-benzyl-1H-thieno[2,3-d][1,3]oxazine-2,4-dione (58). Yield 4.2 g (56%); MP 183° C. $^1$H-NMR (DMSO-d$_6$) δ 2.31 (s, 3H), 5.10 (s, 2H), 6.85 (s, 1H), 7.37 (m, 5H) ppm; EIMS m/z 274 (M+1).

Synthesis of 7-benzyl-4-hydroxy-6-oxo-6,7-dihydro-thieno[2,3-b]pyridine-5-carboxylic acid ethyl ester (60)

Diethyl malonate (2.14 mL, 0.014 mol) was added slowly to a suspension of sodium hydride (60% dispersion in mineral oil, 0.66 g, 0.017 mol) in 50 mL anhydrous DMF stirred at 0° C. under argon. The solution was stirred for 15 minutes. Solid 1-benzyl-1H-thieno[2,3-d][1,3]oxazine-2,4-dione (58) (3.58 g, 0.014 mol) was added, and the solution was heated at 110° C. for 2 hours. The solvent was then removed under vacuum, and the residue was dissolved in water and washed with ethyl acetate. The aqueous layer was acidified with dil. HCl to precipitate the product, which was collected by vacuum filtration to give 3.09 g (68%) of 7-benzyl-4-hydroxy-6-oxo-6,7-dihydro-thieno[2,3-b]pyridine-5-carboxylic acid ethyl ester. MP 146° C. $^1$H-NMR (DMSO-$d_6$) δ 1.30 (t, J=7.2 Hz, 3H), 4.32 (q, J=7.2 Hz, 2H), 5.25 (s, 2H), 7.24-7.36 (m, 7H), 13.21 (b, 1H) ppm; EIMS m/z 330 (M+1).

Synthesis of 7-benzyl-4-hydroxy-3-methyl-6-oxo-6, 7-dihydro-thieno[2,3-b]pyridine-5-carboxylic acid ethyl ester (61)

This compound was prepared from 1-benzyl-5-methyl-1H-thieno[2,3-d][1,3]oxazine-2,4-dione (59) by applying the same method described for the preparation of 7-benzyl-4-hydroxy-6-oxo-6,7-dihydro-thieno[2,3-b]pyridine-5-carboxylic acid ethyl ester (60). Yield 80%; MP 166° C. $^1$H-NMR (DMSO-$d_6$): δ 1.32 (t, J=6.8 Hz, 3H), 2.40 (d, J=1.2 Hz, 3H), 4.36 (q, J=6.8 Hz, 2H), 5.22 (s, 2H), 6.84 (d, J=1.2 Hz, 1H), 7.25 (m, 3H), 7.32 (m, 2H), 14.04 (b, 1H) ppm; EIMS m/z 344 (M+1).

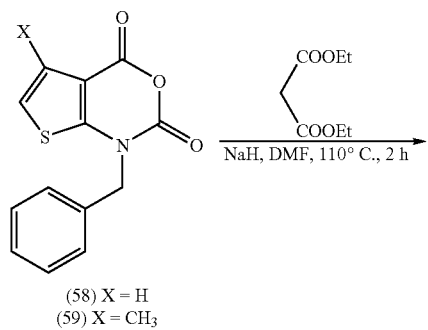

(58) X = H
(59) X = CH$_3$

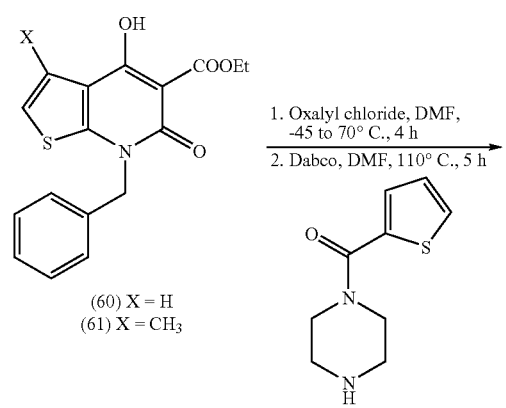

(60) X = H
(61) X = CH$_3$

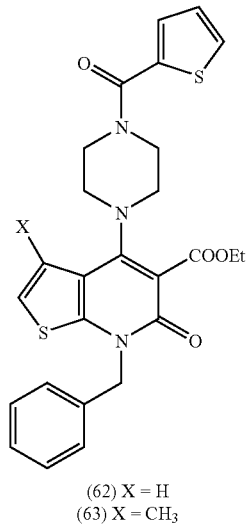

(62) X = H
(63) X = CH$_3$

Synthesis of 7-benzyl-6-oxo-4-[4-(thiophene-2-carbonyl)-piperazin-1-yl]-6,7-dihydro-thieno[2,3-b] pyridine-5-carboxylic acid ethyl ester (62)

Oxalyl chloride (0.66 mL, 0.008 mol) was added slowly to a solution of 7-benzyl-4-hydroxy-6-oxo-6,7-dihydro-thieno[2,3-b]pyridine-5-carboxylic acid ethyl ester (60) (1.0 g, 0.003 mol) in 25 mL anhydrous DMF stirred at −45° C. under argon. The solution was heated to 70° C. for 4 hours, and then poured into water. A small amount of brine was added, and the precipitated solid was collected by vacuum filtration. The oily solid was dissolved in dichloromethane, dried with magnesium sulfate, and then concentrated under vacuum to yield an oil. The oil was dissolved in DMF. Piperazin-1-yl-thiophen-2-yl-methanone (1.2 g, 0.004 mol) and DABCO (0.68 g, 0.006 mol) were added to the solution under argon. The solution was heated to 110° C. for 5 hours, and then poured into a 5% ammonium chloride aqueous solution. The precipitated solid was collected by vacuum filtration, and then purified by reverse phase (MeCN/water) chromatography to yield 0.320 g (21%) of 7-benzyl-6-oxo-4-[4-(thiophene-2-carbonyl)-piperazin-1-yl]-6,7-dihydro-thieno[2,3-b]pyridine-5-carboxylic acid ethyl ester. $^1$H-NMR (DMSO-$d_6$) δ 1.28 (t, J=7.2 Hz, 3H), 3.40 (b, 4H), 3.81 (b, 4H), 4.26 (q, J=7.2 Hz, 2H), 5.26 (s, 2H), 7.15 (m, 1H), 7.28 (m, 5H), 7.35 (m, 2H), 7.47 (m, 1H), 7.79 (m, 1H) ppm; EIMS m/z 508 (M+1).

Synthesis of 7-benzyl-3-methyl-6-oxo-4-[4-(thiophene-2-carbonyl)-piperazin-1-yl]-6,7-dihydro-thieno[2,3-b]pyridine-5-carboxylic acid ethyl ester (63)

This compound was prepared from 7-benzyl-4-hydroxy-3-methyl-6-oxo-6,7-dihydro-thieno[2,3-b]pyridine-5-carboxylic acid ethyl ester (61) by applying the method described for the preparation of 7-benzyl-6-oxo-4-[4-(thiophene-2-carbonyl)-piperazin-1-yl]-6,7-dihydro-thieno[2,3-b]pyridine-5-carboxylic acid ethyl ester (62). Yield 16%; MP 195° C. $^1$H-NMR (DMSO-$d_6$) δ 1.29 (t, J=7.2 Hz, 3H), 2.53 (d, J=1.2 Hz, 3H), 4.29 (q, J=7.2 Hz, 2H), 5.27 (s, 2H), 6.94 (d, J=1.2 Hz, 1H), 7.16 (m, 1H) 7.28 (m, 3H), 7.33 (m, 2H), 7.43 (dd, J=0.8, 3.6 Hz, 1H), 7.79 (dd, J=0.8, 4.8 Hz, 1H) ppm; EIMS m/z 522 (M+1).

Synthesis of 7-benzyl-4-chloro-6,7-dihydro-6-oxo-thieno[2,3-b]pyridine-5-carbonitrile (64)

Cyclohexylamine (1.44 mL, 0.013 mol) was added to a solution of ethyl 7-benzyl-4-hydroxy-6-oxo-6,7-dihydro-thieno[2,3-b]pyridine-5-carboxylic acid ethyl ester (60) (2.07 g, 0.006 mol) in toluene stirred under argon. The solution was refluxed for 4 hours, and then the toluene was removed under vacuum. The residue was dissolved in dichloromethane and washed with sodium bisulfate solution. The organic layer was dried over magnesium sulfate and concentrated under vacuum to give an oil. The oil was dissolved in 25 mL phosphorus oxychloride and cooled to 0° C., and triethylamine (2.18 mL, 0.016 mol) was added. The reaction was heated to 100° C. for 4 days. The solution was cooled and excess phosphorus oxychloride was removed under vacuum The residue was suspended in water and the solid was collected by vacuum filtration. The solid was dissolved in dichloromethane, washed with saturated solution of sodium bicarbonate, water, and brine. The organic layer was dried over magnesium sulfate and concentrated under vacuum to give 1.56 g (83%) of 7-benzyl-4-chloro-6,7-dihydro-6-oxo-thieno[2,3-b]pyridine-5-carbonitrile. $^1$H-NMR (DMSO-$d_6$) δ 5.37 (s, 2H), 7.34 (m, 6H), 7.49 (m, 1H) ppm; EIMS m/z 301 (M+1).

Synthesis of 7-benzyl-4-chloro-6,7-dihydro-3-methyl-6-oxo-thieno[2,3-b]pyridine-5-carbonitrile (65)

This compound was prepared from 7-benzyl-4-hydroxy-3-methyl-6-oxo-6,7-dihydro-thieno[2,3-b]pyrdine-5-carboxylic acid ethyl ester (61) by applying a similar procedure as described for the preparation of 7-benzyl-4-chloro-6,7-dihydro-6-oxo-thieno[2,3-b]pyrdine-5-carbonitrile (64). Yield 87%. $^1$H-NMR (DMSO-$d_6$): δ 2.48 (s, 3H), 5.36 (s, 2H), 7.14 (s, 1H), 7.32 (m, 5H) ppm; EIMS m/z 315 (M+1).

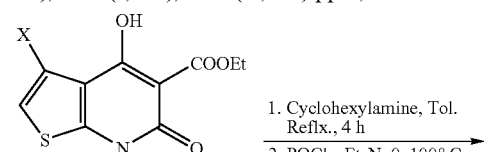

(60) X = H
(61) X = CH$_3$

1. Cyclohexylamine, Tol. Reflx., 4 h
2. POCl$_3$, Et$_3$N, 0–100° C. 4 d

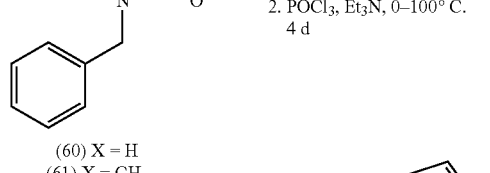

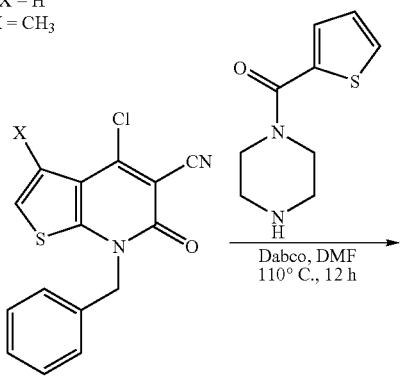

Dabco, DMF
110° C., 12 h

(64) X = H
(65) X = CH$_3$

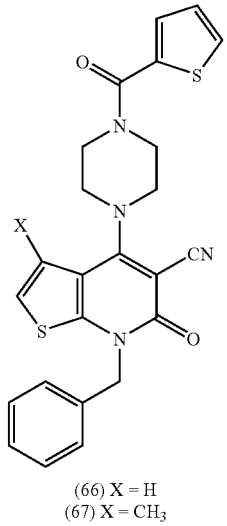

(66) X = H
(67) X = CH$_3$

Synthesis of 7-benzyl-6-oxo-4-[4-(thiophene-2-carbonyl)-piperazin-1-yl]-6,7-dihydro-thieno[2,3-b]pyrdine-5-carbonitrile (66)

A solution of 7-benzyl-4-chloro-6,7-dihydro-6-oxo-thieno[2,3-b]pyridine-5-carbonitrile (64) (0.750 g, 0.0025 mol), piperazin-1-yl-thiophen-2-yl-methanone (0.69 g, 0.0035 mol), and DABCO (0.56 g, 0.005 mol) in anhydrous DMF was heated at 110° C. for 12 h. The solution was cooled and poured into a 5% ammonium chloride aqueous solution and the precipitated solid was collected by vacuum filtration. The solid was purified by reverse phase chromatography (MeCN/water) to yield 0.330 g (29%) of 7-benzyl-6-oxo-4-[4-(thiophene-2-carbonyl)-piperazin-1-yl]-6,7-dihydro-thieno[2,3-b]pyridine-5-carbonitrile. MP 257° C.; 1H-NMR (DMSO-d6) δ 3.83 (m, 8H), 5.28 (s, 2H), 7.16 (m, 1H), 7.33 (m, 7H), 7.51 (d, J=3.2 Hz, 1H), 7.81 (d, J=4.8 Hz, 1H) ppm; EIMS m/z 461 (M+1).

Synthesis of 7-benzyl-3-methyl-6-oxo-4-[4-(thiophene-2-carbonyl)-piperazin-1-yl]-6,7-dihydro-thieno[2,3-b]pyridine-5-carbonitrile (67)

This compound was prepared from 7-benzyl-4-chloro-6,7-dihydro-3-methyl-6-oxo-thieno[2,3-b]pyrdine-5-carbonitrile (65) by applying the same method as described for the preparation of 7-benzyl-6-oxo-4-[4-(thiophene-2-carbonyl)-piperazin-1-yl]-6,7-dihydro-thieno[2,3-b]pyridine-5-carbonitrile (66). Yield 25%; MP 223° C. $^1$H-NMR (DMSO-$d_6$) δ 2.48 (d, J=0.8 Hz, 3H), 3.50 (m, 4H), 3.86 (b, 4H), 5.30 (s, 2H), 6.99 (d, J=1.2 Hz, 1H), 7.16 (m, 1H), 7.30 (m, 5H), 7.47 (dd, J=0.8, 3.6 Hz, 1H), 7.80 (dd, J=1.2, 5.2 Hz, 1H) ppm; EIMS m/z 475 (M+1).

Synthesis of 6-methyl-1H-thieno[2,3-d][1,3]oxazine-2,4-dione (68)

Methyl 2-amino-5-methyl-thiophene-3-carboxylate (16.8 g, 299 mmol) was added to a solution of potassium hydroxide (25 g, 146 mmol) in 300 mL water. The solution was heated at 90° C. until to yield a clear solution. The solution was heated at same temperature for another 30 min and then cooled to 0° C. Trichloromethyl chloroformate (26.42 mL, 219 mmol) was added slowly without allowing the temperature to rise beyond 10° C. The solution was further stirred for 2 h. The precipitated solid was collected by vacuum filtration to yield 21.6 g (83%) of 6-methyl-1H-thieno[2,3-d][1,3]oxazine-2,4-dione. ¹H-NMR (DMSO-d₆) δ 2.38 (d, J=1.2 Hz, 3H), 6.90 (q, J=1.2 Hz, 1H), 12.44 (b, 1H) ppm; EIMS m/z 184 (M+1).

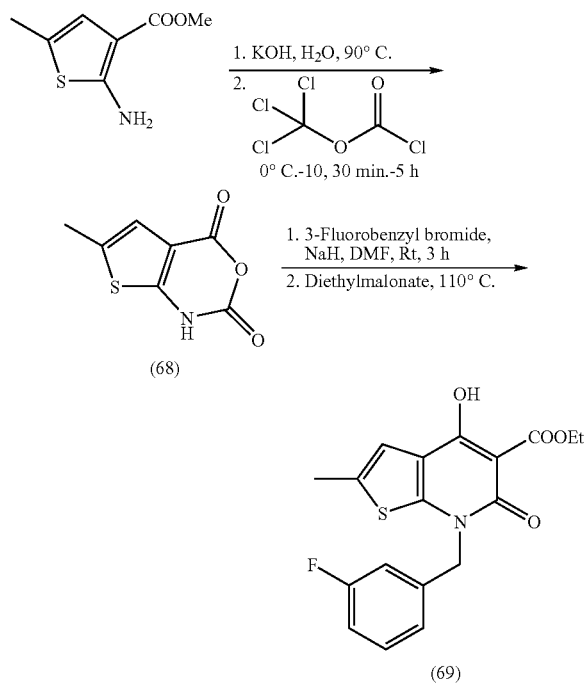

(68)

(69)

Synthesis of 7-(3-fluoro-benzyl)-4-hydroxy-2-methyl-6-oxo-6,7-dihydro-thieno[2,3-b]pyridine-5-carboxylic acid ethyl ester (69)

Sodium hydride (60% dispersion in mineral oil, 5.6 g, 0.140 mol) was added slowly to a solution of 6-methyl-1H-thieno[2,3-d][1,3]oxazine-2,4-dione (68) (11.07 g, 0.060 mol) in anhydrous DMF stirred under argon at 0° C. The solution was stirred for 15 minutes before adding 3-fluoro benzylbromide (7.6 mL, 0.062 mol). The solution was allowed to come at room temperature and further stirred for 3 hours. The solution was cooled to −10° C. and diethylmalonate (9.36 mL, 0.061 mol) was added slowly. The solution was heated at 110° C. (TLC control). The reaction was cooled and poured into aqueous sodium carbonate (7.7 g, 0.072 mol) solution. The aqueous solution was washed with isopropyl ether and acidified to pH 2 with dil. HCl. The solids were filtered, washed by cold water and air dried to yield 16.9 g (97%) of 7-(3-fluoro-benzyl)-4-hydroxy-2-methyl-6-oxo-6,7-dihydro-thieno[2,3-b]pyridine-5-carboxylic acid ethyl ester (69). ¹H-NMR (DMSO-d₆) δ 1.30 (t, J=7.2 Hz, 3H), 2.40 (d, J=1.2 Hz, 3H), 4.32 (q, J=7.2 Hz, 2H), 5.22 (s, 2H), 7.05-7.15 (m, 4H), 7.38 (m, 1H), 13.25 m/z 362 (M+1).

Synthesis of 4-chloro-7-(3-fluoro-benzyl)-2-methyl-6-oxo-6,7-dihydro-thieno[2,3-b]pyridine-5-carboxylic acid ethyl ester (70)

Oxalyl chloride (4.83 mL, 0.055 mol) was added to a solution of 7-(3-fluoro-benzyl)-4-hydroxy-2-methyl-6-oxo-6,7-dihydro-thieno[2,3-b]pyridine-5-carboxylic acid ethyl ester (69) (8 g, 0.022 mol) in DMF at −30° C. under argon. The temperature was raised gradually to 75° C. and stirred for 3 h. The solution was cooled and poured into ice water. The solids formed were filtered, washed by cold water and dried to yield 6.8 g (82%) of 4-chloro-7-(3-fluoro-benzyl)-2-methyl-6-oxo-6,7-dihydro-thieno[2,3-b]pyridine-5-carboxylic acid ethyl ester. ¹H-NMR (DMSO-d₆) δ 1.30 (t, J=7.2 Hz, 3H), 2.45 (d, J=1.2 Hz, 3H), 4.33 (q, J=7.2 Hz, 2H), 5.31 (s, 2H), 7.05 (d, J=1.2 Hz, 1H), 7.09-7.17 (m, 3H), 7.40 (m, 1H) ppm, EIMS m/z 380 (M+1).

Synthesis of 7-(3-fluoro-benzyl)-2-methyl-6-oxo-4-[4-(thiophene-2-carbonyl)-piperazin-1-yl]-6,7-dihydro-thieno[2,3-b]pyridine-5-carboxylic acid ethyl ester (71)

A solution of 4-chloro-7-(3-fluoro-benzyl)-2-methyl-6-oxo-6,7-dihydro-thieno[2,3-b]pyrdine-5-carboxylic acid ethyl ester (70) (3.0 g, 7.89 mmol), piperazin-1-yl-thiophen-2-yl-methanone (1.78 g, 9.09 mmol), and DABCO (1.02 g, 9.09 mmol) in anhydrous DMF was heated overnight at 110° C. The solution was cooled and poured into a 2% ammonium chloride aqueous solution. The precipitated solid was collected by vacuum filtration. The solid was redissolved in dichloromethane and filtered. The filtrate was concentrated under vacuum and the residue was purified by flash chromatography eluting with 0-5% MeOH in CH₂Cl₂ gradient to yield 2.8 g (65%) of 7-(3-fluoro-benzyl)-2-methyl-6-oxo-4-[4-(thiophene-2-carbonyl)-piperazin-1-yl]-6,7-dihydro-thieno[2,3-b]pyridine-5-carboxylic acid ethyl ester. ¹H-NMR (DMSO-d₆) δ 1.29 (t, J=7.2 Hz, 3H), 2.43 (s, 3H), 3.29 (m, 4H), 3.81 (m, 4H), 4.26 (q, J=7.2 Hz, 2H), 5.23 (s, 2H), 6.99 (d, J=1.2 Hz, 1H), 7.06-7.16 (m, 4H), 7.41 (m, 1H), 7.46 (dd, J=1.2, 4.0 Hz, 1H), 7.79 (dd, J=1.2, 4.8 Hz, 1H); EIMS m/z 540(M+1).

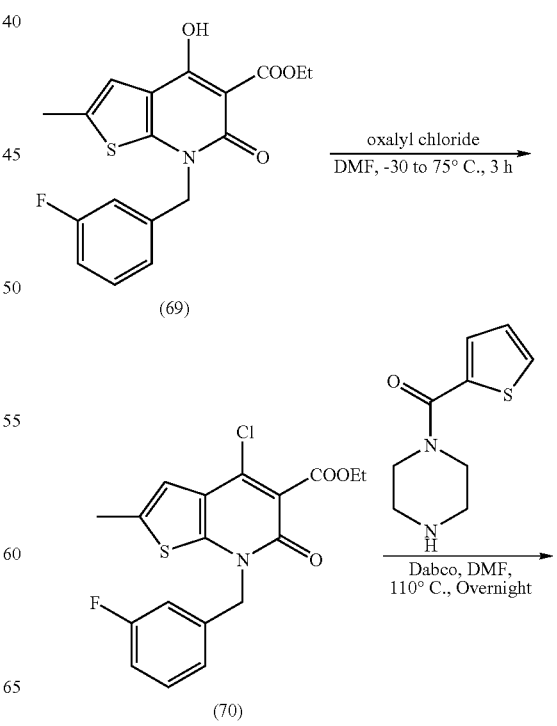

(69)

(70)

-continued

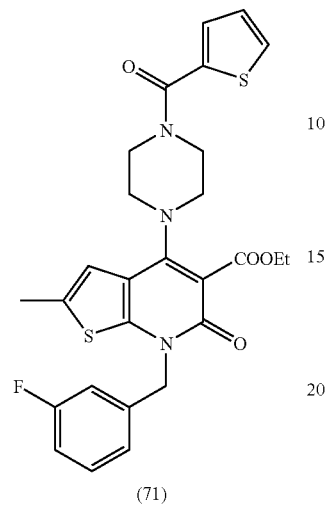

(71)

Antibody Binding Assay of MIF Inhibitors

An antibody binding assay for MIF inhibitors was performed on selected compounds in a 96-well format using MIF produced by THP-1 cells. The THP-1 cells were washed once with 250 µl of 0.1 M sodium carbonate, pH 11.4, for 1 to 2 minutes and immediately aspirated. The THP-1 cells were then washed with media containing 0.5% FBS plus 25 µg/ml heparin and then incubated in this same medium for the indicated lengths of time. The THP-1 cells were resuspended to approx. $5 \times 10^6$ cells/ml in RPMI medium containing 20 µg/ml of bacterial LPS and incubated for 18-20 hours, after which THP-1 cell supernatant was collected and incubated with a candidate compound. A 96-well ELISA plate (Costar Number 3590) was coated with a MIF monoclonal antibody (R&D Systems Catalog Number MAB289) at a concentration of 4 µg/ml for two hours at 37° C. Undiluted THP-1 cell culture supernatant incubated with the candidate compound was added to the ELISA plate for a two-hour incubation at room temperature. The wells were then washed, a biotinylated MIF polyclonal antibody (R&D Systems #AF-289-PB) was added followed by Streptavidin-HRP and a chromogenic substrate. The amount of MIF was calculated by interpolation from an MIF standard curve. The in vitro MIF $IC_{50}$ (nM) of selected candidate compounds is provided in Table 1.

Each of the compounds tested exhibited MIF inhibiting activity in the assay, i.e., they inhibit MIF activity and are therefore suitable for use as pharmaceutical compositions for the treatment of diseases mediated by MIF. Assay test results for preferred compounds are provided in Table 1.

TABLE 1

| Compound | Structure | In vitro MIF $IC_{50}$ (nM) |
| --- | --- | --- |
| 101 | 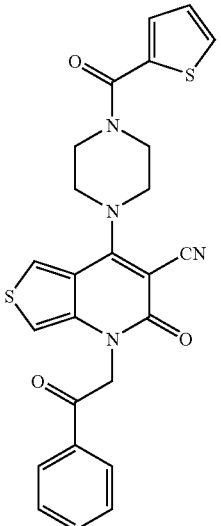 | 70 |
| 102 | 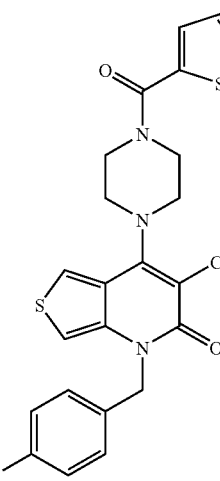 | 82 |
| 103 | 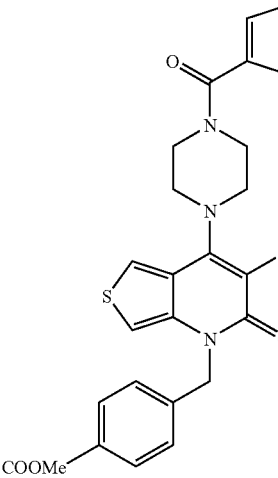 | 437 |

TABLE 1-continued

| Compound | Structure | In vitro MIF IC$_{50}$ (nM) |
|---|---|---|
| 104 | (structure) | 59 |
| 105 | (structure) | 53 |
| 106 | (structure) | 40 |
| 107 | (structure) | 35 |
| 108 | (structure) | 171 |
| 109 | (structure) | 233 |

TABLE 1-continued

| Compound | Structure | In vitro MIF IC$_{50}$ (nM) |
|---|---|---|
| 110 | 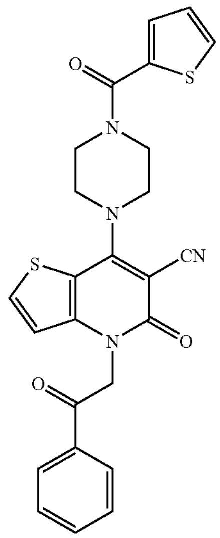 | 1,734 |
| 111 | 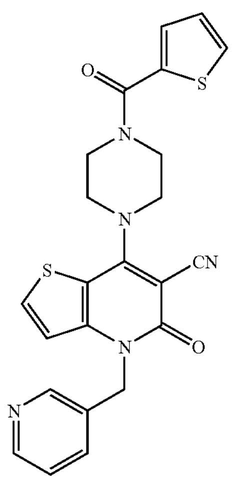 | 254 |
| 112 | 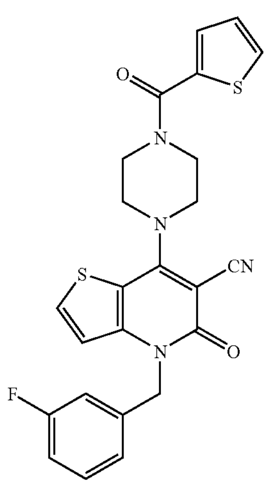 | 595 |
| 113 | | 419 |
| 114 | | 70 |
| 115 | | 11,800 |

TABLE 1-continued

| Compound | Structure | In vitro MIF IC$_{50}$ (nM) |
|---|---|---|
| 116 | 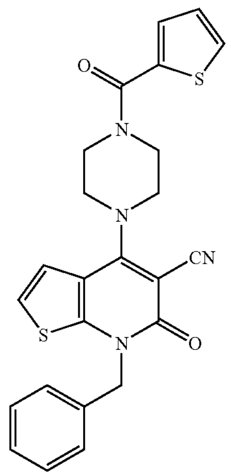 | 139 |
| 117 | 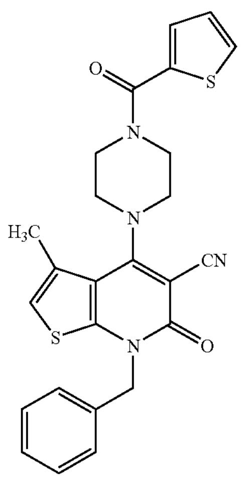 | 12,260 |
| 119 | 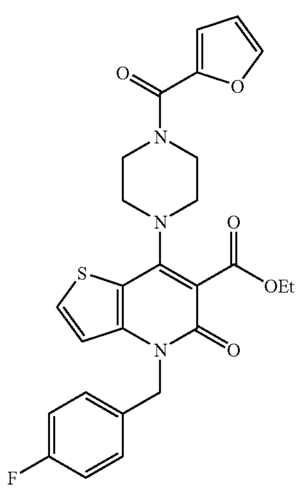 | 4,150 |
| 120 | | 799 |
| 121 | | 146 |
| 122 | | 5,840 |

TABLE 1-continued

| Compound | Structure | In vitro MIF IC$_{50}$ (nM) |
|---|---|---|
| 123 | 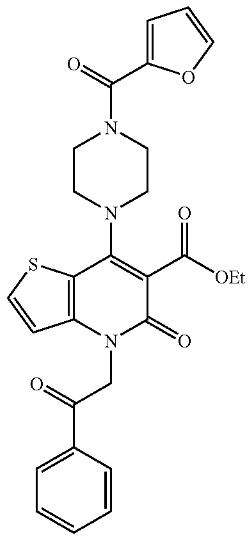 | 8,770 |
| 124 | 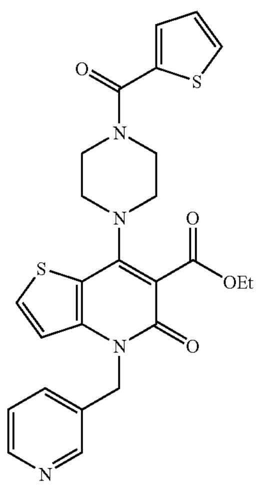 | 269 |
| 125 | 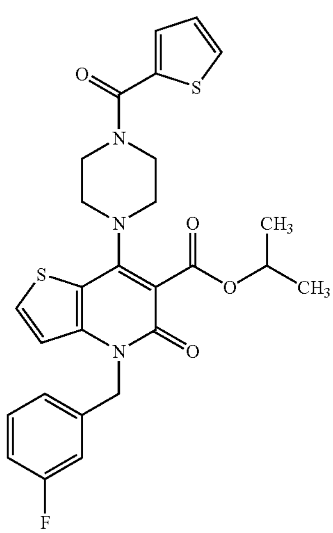 | 387 |
| 126 | 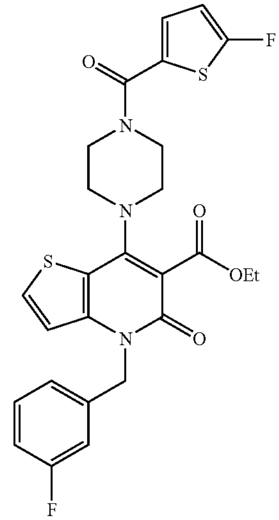 | 648 |
| 127 | 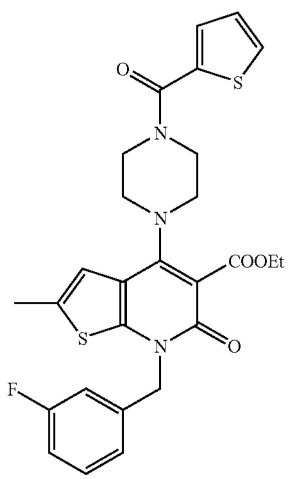 | 32 |

Amongst other uses, the MIF inhibitors of the preferred embodiments, particular including the specific compounds in Table 1, are useful for the treatment of MIF-mediated diseases, such as inflammatory and autoimmune diseases including, but not limited to arthritis, uveoritinitis, colitis (including Crohn's disease and ulcerative colitis), nephritis, atopic dermatitis, psoriasis, proliferative vascular disease, cytokine-mediated toxicity, sep sis, septic shock, interleukin-2 toxicity, acute respiratory distress syndrome (ARDS), asthma, insulin-dependent diabetes, multiple sclerosis, artherosclerosis, graft versus host disease, lupus syndromes, and other conditions characterized by local or systemic MIF-release or synthesis. The MIF inhibitors of the preferred embodiments can, e.g, further be used to treat tumor growth and angiogenesis, and to treat malaria. The minimum inhibitory concentration (MIC) of the MIF inhibitors of Table 1, as well as other MIF inhibitors of preferred embodiments as described herein, against these diseases or conditions is from about 1.0 nM to about 100 µM. For the treatment of these diseases or conditions, the MIF inhibitors of the preferred embodiments can be administered to larger mammals, for example humans, by oral, intravenous or intramuscular administration at doses of from less than about 1.0 mg to dosages of 100 mg/Kg or more, as are used with other conventional therapies.

In diseases and conditions which are mediated by MIF, such as those described herein, treatment comprises administering to a subject in need of such treatment an effective amount of a MIF inhibitor of Table 1, or one or more other MIF inhibitors of the preferred embodiments in the form of a pharmaceutical composition. The term "treatment" as used herein is a broad term, and is to be given its ordinary and customary meaning to a person of ordinary skill in the art (and is not to be limited to a special or customized meaning), and refers without limitation to both treatment of an existing disease or condition, as well as prophylaxis. For such treatment, the appropriate dosage depends upon, for example, the chemical nature, and the pharmacokinetic data of the MIF inhibitor, the individual host, the mode of administration and the nature and severity of the disease or condition being treated. However, in general, for satisfactory results in larger mammals, for example humans, an indicated daily dosage of from about 0.01 g to about 1.0 g, of a MIF inhibitor of the preferred embodiments can be conveniently administered, for example, in a single dose or in divided doses up to two, three, or four or more times a day.

Various MIF inhibitors and methods of preparing and using the same, as well as assays for use in determining MIF inhibiting activity of candidate compounds, are disclosed in U.S. Publication No. US-2003-0195194-A1; U.S. Publication No. US-2004-0204586-A1; and U.S. Publication No. US-2005-0124604-A1.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A compound having a structure selected from the group consisting of:

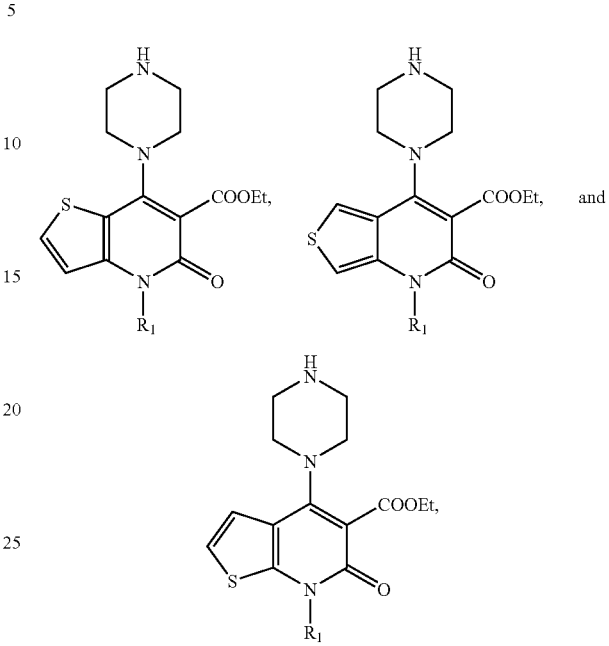

or a stereoisomer, or a pharmaceutically acceptable salt thereof, wherein $R_1$ is selected from the group consisting of hydrogen, $C_{1-8}$ alkyl, $-(CH_2)_x-(C_{6-18}$ aryl), and $-(CH_2)_x$-pyridyl, wherein x is 0 to 4, and wherein $R_1$ is unsubstituted or substituted with at least one substituent selected from the group consisting of halogen, keto, $C_{1-6}$ alkyl, $C_{1-6}$ alkoxy, $C_{1-6}$ alkylamino, and di-($C_{1-6}$ alkyl)amino.

2. The compound of claim 1, wherein $R_1$ is $-(CH_2)_x-$ ($C_{6-18}$ aryl).

3. The compound of claim 2, wherein x is 1 or 2.

4. The compound of claim 1, wherein $R_1$ is $-(CH_2)_x$-pyridyl.

5. The compound of claim 4, wherein x is 1 or 2.

6. The compound of claim 1, wherein $R_1$ is $-CH_2$(2-pyridyl).

7. The compound of claim 1, wherein $R_1$ is $-CH_2Ph$.

8. A compound having a structure selected from the group consisting of:

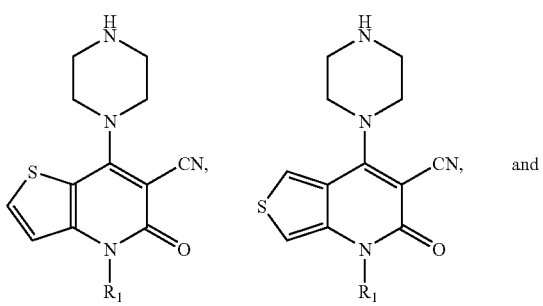

-continued

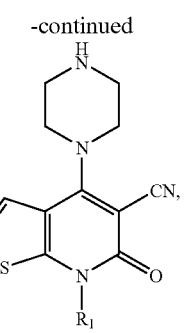

or a stereoisomer, or a pharmaceutically acceptable salt, thereof, wherein $R_1$ is selected from the group consisting of hydrogen, $C_{1-8}$ alkyl, —$(CH_2)_x$—$(C_{6-18}$ aryl), and —$(CH_2)_x$-pyridyl, wherein x is 0 to 4, and wherein $R_1$ is unsubstituted or substituted with at least one substituent selected from the group consisting of halogen, keto, $C_{1-6}$ alkyl, $C_{1-6}$ alkoxy, $C_{1-6}$ alkylamino, and di-($C_{1-6}$ alkyl)amino.

9. The compound of claim 8, wherein $R_1$ is —$(CH_2)_x$—$(C_{6-18}$ aryl).

10. The compound of claim 9, wherein x is 1 or 2.

11. The compound of claim 8, wherein $R_1$ is —$(CH_2)_x$-pyridyl.

12. The compound of claim 11, wherein x is 1 or 2.

13. The compound of claim 8, wherein $R_1$ is —$CH_2$(2-pyridyl).

14. The compound of claim 8, wherein $R_1$ is —$CH_2$Ph.

15. A compound having a structure selected from the group consisting of:

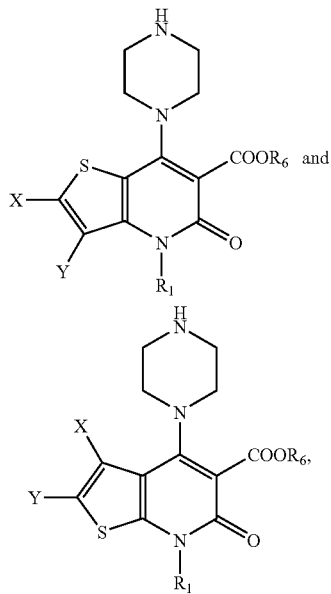

or a stereoisomer, or a pharmaceutically acceptable salt, thereof, wherein:

$R_1$ is selected from the group consisting of hydrogen, $C_{1-8}$ alkyl, —$(CH_2)_x$—$(C_{6-18}$ aryl), and —$(CH_2)_x$-pyridyl, wherein x is 0 to 4, and wherein $R_1$ is unsubstituted or substituted with at least one substituent selected from the group consisting of halogen, keto, $C_{1-6}$ alkyl, $C_{1-6}$ alkoxy, $C_{1-6}$ alkylamino, and di-($C_{1-6}$ alkyl)amino;

$R_6$ is $C_{1-6}$ alkyl;

X is selected from the group consisting of hydrogen, halogen, $C_{1-6}$ alkyl, $C_{1-6}$ alkoxy, $C_{1-6}$ alkylamino, or di-($C_{1-6}$ alkyl)amino; and Y is selected from the group consisting of hydrogen, halogen, $C_{1-6}$ alkyl, $C_{1-6}$ alkoxy, $C_{1-6}$ alkylamino, or di-($C_{1-6}$ alkyl)amino.

16. The compound of claim 15, wherein $R_1$ is —$(CH_2)_x$—$(C_{6-18}$ aryl) and x is 1 or 2.

17. The compound of claim 15, wherein $R_1$ is —$(CH_2)_x$-pyridyl and wherein x is 1 or 2.

18. The compound of claim 15, wherein X is hydrogen and Y is hydrogen.

19. The compound of claim 15, wherein X is methyl and Y is hydrogen.

20. The compound of claim 15, wherein $R_1$ is —$CH_2$(2-pyridyl).

21. The compound of claim 15, wherein $R_1$ is —$CH_2$Ph.

22. A compound having a structure:

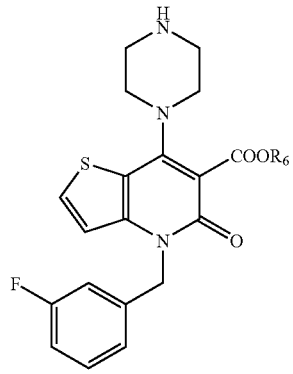

or a stereoisomer, or a pharmaceutically acceptable salt, thereof, wherein $R_6$ is selected from the group consisting of

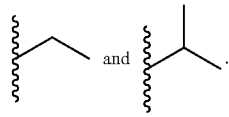

* * * * *